United States Patent [19]
Jessell et al.

[11] Patent Number: 5,279,966
[45] Date of Patent: Jan. 18, 1994

[54] CLONING, EXPRESSION AND USES OF A NOVEL SECRETED PROTEIN, F-SPONDIN

[75] Inventors: Thomas M. Jessell, New York; Avihu Klar, Bronx, both of N.Y.

[73] Assignee: The Trustees of Columbia University in the City of New York, New York, N.Y.

[21] Appl. No.: 862,021

[22] Filed: Apr. 2, 1992

[51] Int. Cl.⁵ .................. C12N 15/00; C12N 15/12; C07H 17/00
[52] U.S. Cl. .................. 435/320.1; 435/69.1; 435/252.3; 530/395; 530/399; 536/23.5
[58] Field of Search ............... 530/395, 399; 435/69.1, 435/252.3, 320.1; 536/23.5

[56] References Cited

PUBLICATIONS

O'Shea et al., Neuron, vol. 7, pp. 231–237, Aug., 1991; "Thrombospondin and a 140 kd Fragment Promote Adhesion and . . . ".

Kosfeld et al., J. Biol. Chem., vol. 266, No. 3, pp. 24257–24259, Dec. 25, 1991; "Cell Attachment Activity of the Carboxy-terminal . . . ".

Klar et al., Cell, vol. 69, Apr. 3, 1992; pp. 95–110; "F--Spondin: A Gene Expressed at High Levels in the Floor Plate . . . ".

Frazier, W. A., J. Cell Biol., vol. 105, Aug., 1987; pp. 625–632 "Thrombospondin: A Molecular Adhesive Glycoprotein . . . ".

Jacobson, M. (1991), Developmental Neurobiology, pp. 41–93 (Exhibit B).

Jessell, T. M. and Dodd, J. (1991), Neurodegenerative Disorders: Mechanisms and Prospects for Therapy, pp. 105–126 (Exhibit C).

Jessell, T. M. and Dodd, J. (1992), The Harvey Lectures, 86:87–128 (Exhibit D).

*Primary Examiner*—Robert A. Wax
*Assistant Examiner*—Andrew Granston
*Attorney, Agent, or Firm*—John P. White

[57] ABSTRACT

This invention provides an isolated vertebrate nucleic acid molecule encoding F-spondin. This invention also provides a probe comprising a nucleic acid molecule of at least 15 nucleotides capable of specifically hybridizing with a sequence included within the sequence of a nucleic acid molecule encoding a F-spondin. This invention provides a host vector system for the production of a F-spondin. This invention provides purified F-spondin and the uses of compositions containing purified F-spondin. This invention further provides a method of attaching nerve cells to a matrix using purified F-spondin. This invention also provides a method of stimulating nerve cell growth using purified F-spondin. This invention further provides a method of regenerating nerve call using purified F-spondin. Finally, this invention provides a pharmaceutical composition for stimulating nerve cell growth comprising an effective amount of purified F-spondin and a pharmaceutically acceptable carrier.

16 Claims, 22 Drawing Sheets

Floor plate induction by the notochord

Control of D-V cell pattern by the floor plate

Chemotropic guidance of commissural axons by the floor plate

Contact-dependent guidance of commissural axons by the floor plate

FIGURE 5A-1

```
CCCTCCCTCTTCGCGCTCCTTCGCCACCGCCCCCTCGCCCCCTCAGCTCCGCTCGGCTCCGC
TCAGAGCAGCGCAGCTCCGCAGCCCAAGCGAGGCGGGCAGGCGAGGCTCCCCACCGCCAGTGC
CACCCGGGCTCCTCCAGCTTTCGCCTCTGCAGCTCCGTCACTTGGAGTAAAAGTGTCCT
GACAGGGTCTGCAACATCAGCAGAAAGTTGGGAGGTCCCTCGAGAATGAGGCTATCTCCC
                                          M  R  L  S  P
GCGCCCCTGAGGCTTAGCCGGGGTCCGGCGCTGGCCCTGGCCCTGGCCCTTGGCCCCGCA
 A  P  L  R  L  S  R  G  P  A  L  L  A  L  P  L  A  A
GCGCTCGCTTTCTCGGATGAGACCCTGGACAAAGTGGCCAAGTCGGAGGGCTACTGCAGC
 A  L  A  F  S  D  E  T  L  D  K  V  A  K  S  E  G  Y  C  S
CGCATCTTGCGCGCCCAGGGCACACGGCGTGAGGGATACACAGAGTTCAGCCTCCGCGTG
 R  I  L  R  A  Q  G  T  R  R  E  G  Y  T  E  F  S  L  R  V
GAAGGCGACCCTGACTTCTATAAGCCAGGAAGCAGCTACCGAGTCACACTCTCGGCTGCC
 E  G  D  P  D  F  Y  K  P  G  S  S  Y  R  V  T  L  S  A  A
CCTCCCTCCTACTTCAGAGGCTTCACGTTAATTGCTCTCAAAGAGAACCGGAAGGCGAT
 P  P  S  Y  F  R  G  F  T  L  I  A  L  K  E  N  R  E  G  D
AAGGAAGAAGACCACGGGGCCTTCCAGATCATAGATGAAGAAACCCAGTTTATG
 K  E  E  D  H  A  G  T  F  Q  I  I  D  E  E  T  Q  F  M
AGTAACTGTCCTGTGGCAGTCACTGAAAGCACAGGACGACACGGATCCAGGTG
 S  N  C  P  V  A  V  T  E  S  T  P  R  R  R  T  R  I  Q  V
TTTTGGATAGCCGGCATTATTTCAAGACGACAGAGGGCTCCCTGACCAAGAAGCTGTGTGAACAGGAT
 F  W  I  A  P  P  T  G  C  V  I  L  K  A  S  I  V  Q
AAACGCATTATCTATTTTCAAGACGACGAGGGCTCCCTGACCAAGAAGCTGTGTGAACAGGAT
 K  R  I  I  Y  F  Q  D  E  G  S  L  T  K  K  L  C  E  Q  D
CCCACACTGATGGAGTGACGACAGACCGATCTTAGACTGCCTGCGCTGCCACGTAGCCTGCC
 P  T  L  D  G  V  T  D  R  P  I  L  D  C  C  A  C  G  T  A
AAGTACAGACTCACGTTTTATGGGAACTGGTCGGAGAAGACTCATCCAAAGGATTACCCT
 K  Y  R  L  T  F  Y  G  N  W  S  E  K  T  H  P  K  D  Y  P
```

FIGURE 5A-2

```
CGTCGGGCTAATCACTGGTCTCTGCCATCATTGGCGGATCCCACTCCAAGAACTACGTGCTG
 R  R  A  N  H  W  S  A  I  I  G  G  S  H  S  K  N  Y  V  L
TGGGAGTACGGAGGGTATGCCAGTGAAGGGTCAAGCAAGTTGCTGAACTTGGCTCACCA
 W  E  Y  G  G  Y  A  S  E  G  V  K  Q  V  A  E  L  G  S  P
GTAAAAATGGAGGAAGAAATTCGACAACAGAGTCCTCACTGTCATCAAAGCC
 V  K  M  E  E  E  I  R  Q  Q  S  D  E  V  L  T  V  I  K  A
AAAGCCCAGTGGCCATCCTGGCCAGCCCTGTGTCAATGTGAGAGCACCCTCAGCCGAATTC
 K  A  Q  W  P  S  W  Q  P  V  N  V  R  A  A  P  S  A  E  F
TCAGTGGACAGGACGCACTTGATGTCCTTCCTAACCATGATGGCCCCAGTCCTGAC
 S  V  D  R  T  R  H  L  M  S  F  L  T  M  G  P  S  P  D
TGGAACGTGGCCTATCGCAGGATCTGTGCACAAGGAGTGTGGGTCCAGAAA
 W  N  V  G  L  S  A  E  D  L  C  T  K  E  C  G  W  V  Q  K
GTGGTGCAGGACCTAATTCCCTGGGATGCTGGACACAGCCCCTGACTAGTCTGGACCATCCT
 V  V  Q  D  L  I  P  W  D  A  G  T  D  S  G  V  T  Y  E  S
CCAAACAAGCCCACAATTCCTCAGGAAAAAATCGACCCCGAAGGTCCATCACACAAGTGGCCAGAGTCGTCATC
 P  N  K  P  T  I  P  Q  E  K  I  R  P  L  T  S  L  D  H  P
CAGAGTCCTTTCTATGACCCGGAAGGTGGGTCCATCACACAAGTGGCCAGAGTCGTCATC
 Q  S  P  F  Y  D  P  E  G  G  S  I  T  Q  V  A  R  V  V  I
GAGAGAATTGCCCGGAAGGAGAACAATGCAACATTGTACCTGACAATGTGGATGATATT
 E  R  I  A  R  K  G  E  Q  C  N  I  V  P  D  N  V  D  D  I
GTAGCCGACCTGGCTCCAGAAGAGAAGATGAAGATGACACCCCTGAAACCTGCATCTAC
 V  A  D  L  A  P  E  E  K  D  E  D  D  T  P  E  T  C  I  Y
```

FIGURE 5A-3

```
TCCAACTGGTCCCCATGGTCTCGGCCCTGCAGCTCTTCCACTTGTGAAAAGGGTAAGAGGATG
 S  N  W  S  P  W  S  A  C  S  S  S  T  C  E  K  G  K  R  M
CGGCAAGCATGCTGAAGGCACAGCTGGACCTCAGTGTCCCTGTCCCAGGACCCAGGAC
 R  Q  R  M  L  K  A  Q  L  D  L  S  V  P  C  P  D  T  Q  D
TTCCAGCCCTGCATGGGCCCTGGTGCAGCGATGAAGATGGCTCCACCTGTACCATGTCG
 F  Q  P  C  M  G  P  G  C  S  D  E  D  G  S  T  C  T  M  S
GAGTGGGATCACCTGGTCTCACCTGTGTCTCGTGTGGGTATGAGGTCCCGGAG
 E  W  I  T  W  S  P  C  S  V  S  C  G  M  G  M  R  S  R  E
AGGTACGTGAAGCAGTTCCCGGAAGACGGAGTGCTGCCAGCTGCTGGTGACTGAGTGGGT
 R  Y  V  K  Q  F  P  E  D  G  S  V  C  M  L  P  T  E  E  T
GAGAAGTGCACGGTCAACGAGGAGTGTCAGCCGCCACCCTGTGGAATGGGCATGAAGAAGC
 E  K  C  T  V  N  E  E  C  S  P  S  S  C  L  V  T  E  W  G
GAGTGGGATGACTGCAGCGCCACCTGTGGAATGGGCATGTGCAAGGCCGAGACTTCG
 E  W  D  D  C  S  A  T  C  G  M  K  K  R  H  R  M  V
AAGATGAGCCCCGCGGACGGCTCCATGTGCAAGGCCGAGACTTCGCAGGCGGAGAAATGC
 K  M  S  P  A  D  G  S  M  C  K  A  E  T  S  Q  A  E  K  C
ATGATGCCTGAGTGCCATACCATCCCGTGCTTGTCCTTGCCTTGGTCCGAGTGGAGCGAC
 M  M  P  E  C  H  T  I  P  C  L  S  P  W  S  E  W  S  D
TGTAGCGTGACCTGTGGGAAGGCATGCGGATCTCAAGTGCTCAAGTCTCTGGCA
 C  S  V  T  C  G  K  G  M  R  T  R  Q  R  M  L  K  S  L  A
GAGCTGGGGACTGTAATGAGGATCTGGAACAGGCGGAGAAGTGTATGCTGCCAGAGTGC
 E  L  G  D  C  N  E  D  L  E  Q  A  E  K  C  M  L  P  E  C
```

FIGURE 5A-4

```
CCCATTGACTGCGAACTCAGTGAGTGCCAGTGGTCCCAGTGGTCTGAATGTAACAAGTCCTGTGGG
 P   I   D   C   E   L   S   E   W   S   Q   W   S   E   C   N   K   S   C   G
AAAGGTCACATGATTCGAACCCGGACAATCCAAATGGAACCTCAGTTTGGAGGTGCACCC
 K   G   H   M   I   R   T   R   T   I   Q   M   E   P   Q   F   G   G   A   P
TGCCCAGAGACTGTGCAACGCAAGAGTGCCGTGCCCGGAAATGCCTTCGCAGCCCATCG
 C   P   E   T   V   Q   R   K   C   R   A   R   K   C   L   R   S   P   S
ATCCAGAAGCTGCGCTGGAGGGAGGCCCGAGAGCAGGAGTGAGCAGCTGAGGGAA
 I   Q   K   L   R   W   R   E   A   R   E   S   R   R   S   E   Q   L   R   E
GAGTCAGATGGAGAGCAGTTCCCGGATGCGCCCGTGCAGCCTGGTCAGAG
 E   S   D   G   E   Q   F   P   G   C   R   M   R   P   W   T   A   W   S   E
TGCACCAAACTGTGCGGAGGTCAGCTGTTACCAGACTGTGAAGAAGAGTTC
 C   T   K   L   C   G   G   G   I   Q   E   R   Y   M   T   V   K   K   R   F
AAAAGCTCCCAGTTTACCAGCTGCAAGGATAAGAAGGAGATCAGAGCCGTGCAACGTGCAC
 K   S   S   Q   F   T   S   C   K   D   K   K   E   I   R   A   C   N   V   H
CCTTGTTAGTAGGGGTTCAACTCCCCCAGGGCTGCATTCCAGATTCCAGTCACCAATGGTT
 P   C
GGGTGGTGTATTGCTTGTTTAAGATGATTTAAATTGTGTCCACATGTTTCATTTTAC
CGGTGTGGTTTGCCCAATAGTCTTATGGAGGCCCGAGGACATCTTGTCTGAATACTTCTT
GGTGAGTACAGGCATGGGGCCAAGCCGGGCATTCGTGTCCCAGGCGCCATCTTCCTGCACTGAGTTG
AGTAGTGTTGGTTCACCTTGGTACTAAACTCGTGTCCCTCTGAGCATCCCTGGT
CAAGCAGGGTGGAGACTTTGGCCATTTGGCCAAAGGACAGAAGAACCAGGATGCAGCATGCGGG
AGACACAGCCATTAATTGCAAAGACAGATCCTCTCACCTTTGGCTGCTCACTC
TTACAGAAACCTGTTTGTCCGCCCTCCTTTTTATTTAGCACAACTCCAGGCATCTTGGTA
AGTCCCAGGTCATGGGTTCTTCGGTGTCTTCGGTGTCCCAGGCATCACAAGGCGGTGAGGTGGCA
TTTGTTACAAACCTCCCAATACTGCTTTACTGGCATCCAAGGTCAGGTGATGATGG
CTACTTCATTTCATTTGTGAGCCGTTGATTTCCGTGAGTTTTGATTGTGGTGTGCCATAAAT
GTCCTAGGATGCTGGACGGACACATCAGCCTTGTCAGCAGATCCTTCTTTGAGCCAATGT
```

FIGURE 5A-5

```
AGACAGTAAGCTGGGCACTGGTTCCAAAGCCAACTTAAAATCTTCCTACACATATCCAGA
CCTTTTTTAGGTTGCCCAAACTTCCTTAGAATAAAGCATTTTAGCTCTGAGAACTACTT
GATAAGTCTGCCAGGAAGCCCCAAGTCAATTCTTCAACAAATACTATCTTCCCTACT
TAATTTTTTTAAGTCATGATATTTTATAGTTAGAGGAGAGAGACAATCTATTCCCAT
GACTAAGACACAAACCTACAAGAAAGGGTTACTCAGTCAAGCCTGTGCCTGACTTCTGA
CCAGGCCCCTGATTTCATGGATAGTCCAAAGGAAGGCCAGGGGTTCCCACTGACTCCAA
GCCATCAGCAGCACCCAAACCAGGAGCAACAAATATTCAGAGAAGAGGATGTTTATCT
CAGCTATGAGCTCATTGGCAGGTTGTACTCATGCATCTGTTAAAAGCACCACCATCCT
TTTGCAAGTCTGTTTATTACCGCTTCATCCAAATACATTTTGTGGTCAAGATCGACACAG
TGCTATGAATACAGTACTTTAAGGTCTGCATTAAACACATCAGAATATTTCCTGCCACAT
CTATGTACAACCCCCTGAATATGTATTTTTCCTTAACACAAGAGAGCCTGTTCAATTAAAA
AAAAAAAA
```

FIGURE 6B

```
            1           10          20          30          40          50
            .           .           .           .           .           .
RESIDUES
 NOS.
1  440-499  ETCIYSNWSPWSACSSTC-EKGKRMRQRMLKAQLDLSVPC-PDTQDFQPCM-GPCCSDEDG
2  500-556  STCTMSEWITWSPCSVSCGMGMRSRER-YVKQFP-DG-SVQMLPTEETEKCTVNEECSP
3  557-612  SSCLVTEWGENDDCSATCGMGMKKRFHR-MVKMSPADG-SMCKAETSQAEKCMP-ECHT
4  613-666  IPCLLSPWSEWSDCSVTCGKGM--RTR-QRMLKSLAELGDQNEDLEQAEKCMLP-ECP
5  667-722  IDCELSEWSQWSECNKSCGKGHMIRTR-TIQMEPQFGGAPCPETV-QRKKCRAR-KCLR
6  753-807  PGCRMRPWTAWSPCTKLCGGGIQERYMTVKKRFKSSQFTSCKDKKE-IRACNVH-PC
```

FIGURE 6C

```
F-SPONDIN         C----W--WS-CSVTCG--G----R-R---------C--------C---C   1/6
THROMBOSPONDIN    WS-WS-WS-CSVTCG--G----R-R-C-----C--------C----C     2/3
THROMBOSPONDIN II WS-WS-WS-CSVTCG--G----R-R-C-----C--------C----C     2/3
PROPERDIN         WS-W---WS-CSVTC---G----R-R-C-----C--------C----C     1/6
COMPLEMENT COOH   W-CWS-WS-C--------------R-R-C-----C--------C         0/1
COMPLEMENT NH2    C----WS-WS-C----C-------R-R----------C--------C     0/1
PLASMODIUM cs     WS-CSVTCG--G----R-R                                   1/1
TRAP              WS-CSVTCG--G----R-R---    ----C-----    ----C        1/1
```

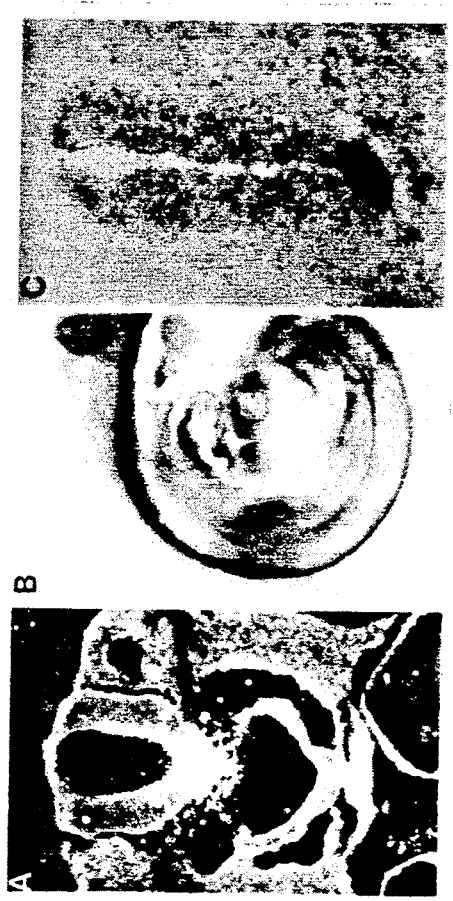

FIGURE 7D
FIGURE 7E

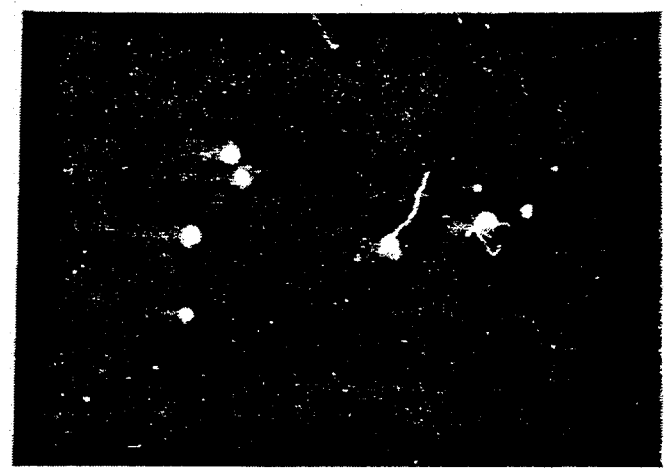
FIGURE 9B
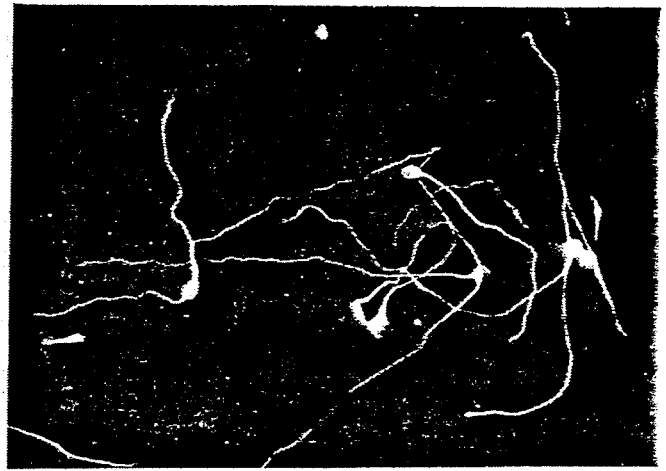
FIGURE 9C
FIGURE 9A
—180
—116
—84
—58
—48
—36
—26

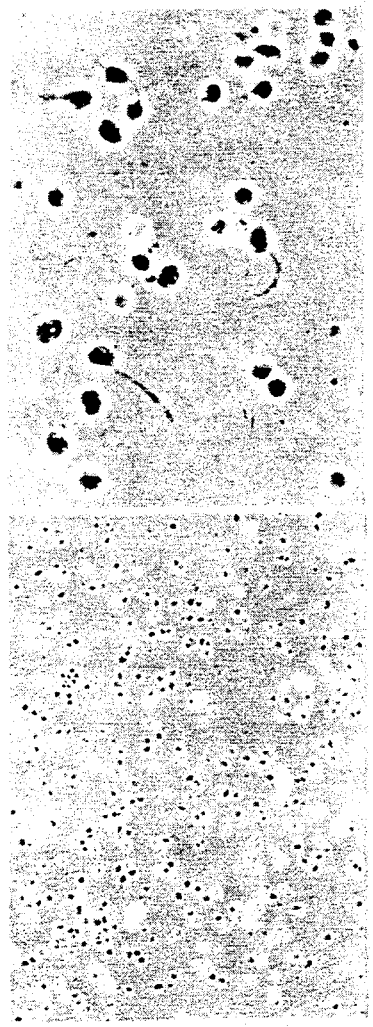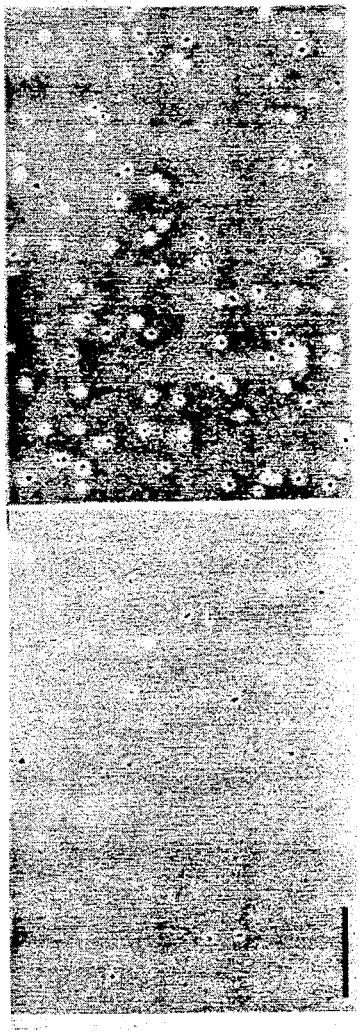

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:1:

CTAGCGAGCA GAAGCTGATC TCCGAGGAGG ACCTCA    3 6

( 2 ) INFORMATION FOR SEQ ID NO:2:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:2:

CTAGTGAGGT CCTCCTCGGA GATCAGCTTC TGCTCG    3 6

( 2 ) INFORMATION FOR SEQ ID NO:3:

( i ) SEQUENCE CHARACTERISTICS:
  ( A ) LENGTH: 10 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

Glu Gln Lys Leu Ile Ser Glu Glu Asp Leu
1               5                   10

(2) INFORMATION FOR SEQ ID NO:4:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:4:

CATGGGAGCA GAAGCTGATC TCCGAGGAGG ACCTCG     36

(2) INFORMATION FOR SEQ ID NO:5:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:5:

CATGCGAGGT CCTCCTCGGA GATCAGCTTC TGCTCC     36

(2) INFORMATION FOR SEQ ID NO:6:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:6:

Val Thr Cys Gly
1

(2) INFORMATION FOR SEQ ID NO:7:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:7:

Val Ser Cys Gly
1

(2) INFORMATION FOR SEQ ID NO:8:

(i) SEQUENCE CHARACTERISTICS:
  (A) LENGTH: 4 amino acids
  (B) TYPE: amino acid
  (C) STRANDEDNESS: single
  (D) TOPOLOGY: linear 5,279,966

-continued ( i i ) MOLECULE TYPE: protein ( x i ) SEQUENCE DESCRIPTION: SEQ ID NO:8:

Ala Thr Cys Gly
1

( 2 ) INFORMATION FOR SEQ ID NO:9:

( i ) SEQUENCE CHARACTERISTICS:
( A ) LENGTH: 4029 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 226..2647

( x i ) SEQUENCE DESCRIPTION: SEQ ID NO:9:

```
CCCTCCCTCT  TCGCGCTCCT  TCGCCACCGC  CCGCCCCTCA  GCTCCGCTGC  TCGGCTCCGC    60

TCAGAGCAGC  GCAGCTCCGC  AGCCAAAGCG  AGGCGGGCTC  GGGCTCCCCA  CCGCCAGTGC   120

CACCCGGGCT  CCTCCAGCTT  TCGCCTCTGC  AGCTCCCGTC  ACTTGGAGTA  AAAGTGTCCT   180

GACAGGGGTC  TGCAACATCA  GCAGAAAGTT  GGGAGGTCCT  CGAGA ATG AGG CTA        234
                                                      Met Arg Leu
                                                        1
```

| TCT | CCC | GCG | CCC | CTG | AGG | CTT | AGC | CGG | GGT | CCG | GCG | CTG | CTG | GCC | CTG | 282 |
|---|---|---|---|---|---|---|---|---|---|---|---|---|---|---|---|---|
| Ser | Pro | Ala | Pro | Leu | Arg | Leu | Ser | Arg | Gly | Pro | Ala | Leu | Leu | Ala | Leu | |
| | 5 | | | | 10 | | | | | 15 | | | | | | |

| GCG | CTG | CCC | CTG | GCC | GCA | GCG | CTC | GCT | TTC | TCG | GAT | GAG | ACC | CTG | GAC | 330 |
|---|---|---|---|---|---|---|---|---|---|---|---|---|---|---|---|---|
| Ala | Leu | Pro | Leu | Ala | Ala | Ala | Leu | Ala | Phe | Ser | Asp | Glu | Thr | Leu | Asp | |
| 20 | | | | | 25 | | | | | 30 | | | | | 35 | |

| AAA | GTG | GCC | AAG | TCG | GAG | GGC | TAC | TGC | AGC | CGC | ATC | TTG | CGC | GCC | CAG | 378 |
|---|---|---|---|---|---|---|---|---|---|---|---|---|---|---|---|---|
| Lys | Val | Ala | Lys | Ser | Glu | Gly | Tyr | Cys | Ser | Arg | Ile | Leu | Arg | Ala | Gln | |
| | | | | 40 | | | | | 45 | | | | | 50 | | |

| GGC | ACA | CGG | CGT | GAG | GGA | TAC | ACA | GAG | TTC | AGC | CTC | CGC | GTG | GAA | GGC | 426 |
|---|---|---|---|---|---|---|---|---|---|---|---|---|---|---|---|---|
| Gly | Thr | Arg | Arg | Glu | Gly | Tyr | Thr | Glu | Phe | Ser | Leu | Arg | Val | Glu | Gly | |
| | | | 55 | | | | | 60 | | | | | 65 | | | |

| GAC | CCT | GAC | TTC | TAT | AAG | CCA | GGA | AGC | AGC | TAC | CGA | GTG | ACA | CTC | TCG | 474 |
|---|---|---|---|---|---|---|---|---|---|---|---|---|---|---|---|---|
| Asp | Pro | Asp | Phe | Tyr | Lys | Pro | Gly | Ser | Ser | Tyr | Arg | Val | Thr | Leu | Ser | |
| | | 70 | | | | | 75 | | | | | 80 | | | | |

| GCT | GCC | CCT | CCC | TCC | TAC | TTC | AGA | GGC | TTC | ACG | TTA | ATT | GCT | CTC | AAA | 522 |
|---|---|---|---|---|---|---|---|---|---|---|---|---|---|---|---|---|
| Ala | Ala | Pro | Pro | Ser | Tyr | Phe | Arg | Gly | Phe | Thr | Leu | Ile | Ala | Leu | Lys | |
| | 85 | | | | | 90 | | | | | 95 | | | | | |

| GAG | AAC | CGC | GAA | GGC | GAT | AAG | GAA | GAA | GAC | CAC | GCG | GGC | ACC | TTC | CAG | 570 |
|---|---|---|---|---|---|---|---|---|---|---|---|---|---|---|---|---|
| Glu | Asn | Arg | Glu | Gly | Asp | Lys | Glu | Glu | Asp | His | Ala | Gly | Thr | Phe | Gln | |
| 100 | | | | | 105 | | | | | 110 | | | | | 115 | |

| ATC | ATA | GAT | GAA | GAA | GAA | ACC | CAG | TTT | ATG | AGT | AAC | TGT | CCT | GTG | GCA | 618 |
|---|---|---|---|---|---|---|---|---|---|---|---|---|---|---|---|---|
| Ile | Ile | Asp | Glu | Glu | Glu | Thr | Gln | Phe | Met | Ser | Asn | Cys | Pro | Val | Ala | |
| | | | | 120 | | | | | 125 | | | | | 130 | | |

| GTC | ACT | GAA | AGC | ACC | CCT | CGG | AGG | AGG | ACA | CGG | ATC | CAG | GTG | TTT | TGG | 666 |
|---|---|---|---|---|---|---|---|---|---|---|---|---|---|---|---|---|
| Val | Thr | Glu | Ser | Thr | Pro | Arg | Arg | Arg | Thr | Arg | Ile | Gln | Val | Phe | Trp | |
| | | | 135 | | | | | 140 | | | | | 145 | | | |

| ATA | GCG | CCA | CCC | ACA | GGG | ACA | GGC | TGT | GTG | ATT | CTG | AAG | GCC | AGC | ATT | 714 |
|---|---|---|---|---|---|---|---|---|---|---|---|---|---|---|---|---|
| Ile | Ala | Pro | Pro | Thr | Gly | Thr | Gly | Cys | Val | Ile | Leu | Lys | Ala | Ser | Ile | |
| | | | 150 | | | | | 155 | | | | | 160 | | | |

| GTA | CAG | AAA | CGC | ATT | ATC | TAT | TTT | CAA | GAC | GAG | GGC | TCC | CTG | ACC | AAG | 762 |
|---|---|---|---|---|---|---|---|---|---|---|---|---|---|---|---|---|
| Val | Gln | Lys | Arg | Ile | Ile | Tyr | Phe | Gln | Asp | Glu | Gly | Ser | Leu | Thr | Lys | |
| | 165 | | | | | 170 | | | | | 175 | | | | | |

| AAG | CTG | TGT | GAA | CAG | GAT | CCC | ACA | CTT | GAT | GGA | GTG | ACG | GAC | AGA | CCG | 810 |
|---|---|---|---|---|---|---|---|---|---|---|---|---|---|---|---|---|
| Lys | Leu | Cys | Glu | Gln | Asp | Pro | Thr | Leu | Asp | Gly | Val | Thr | Asp | Arg | Pro | |
| 180 | | | | | 185 | | | | | 190 | | | | | 195 | |

| | | | | | | | | | | | | | | | | |
|---|---|---|---|---|---|---|---|---|---|---|---|---|---|---|---|---|
| ATC | TTA | GAC | TGC | TGC | GCC | TGC | GGA | ACT | GCC | AAG | TAC | AGA | CTC | ACG | TTT | 858 |
| Ile | Leu | Asp | Cys | Cys 200 | Ala | Cys | Gly | Thr | Ala 205 | Lys | Tyr | Arg | Leu | Thr 210 | Phe | |
| TAT | GGG | AAC | TGG | TCG | GAG | AAG | ACT | CAT | CCA | AAG | GAT | TAC | CCT | CGT | CGG | 906 |
| Tyr | Gly | Asn | Trp 215 | Ser | Glu | Lys | Thr | His 220 | Pro | Lys | Asp | Tyr | Pro 225 | Arg | Arg | |
| GCT | AAT | CAC | TGG | TCT | GCC | ATC | ATT | GGC | GGA | TCC | CAC | TCC | AAG | AAC | TAC | 954 |
| Ala | Asn | His 230 | Trp | Ser | Ala | Ile | Ile 235 | Gly | Gly | Ser | His | Ser 240 | Lys | Asn | Tyr | |
| GTG | CTG | TGG | GAG | TAC | GGA | GGG | TAT | GCC | AGT | GAA | GGG | GTC | AAG | CAA | GTT | 1002 |
| Val | Leu 245 | Trp | Glu | Tyr | Gly | Gly 250 | Tyr | Ala | Ser | Glu | Gly 255 | Val | Lys | Gln | Val | |
| GCT | GAA | CTT | GGC | TCA | CCA | GTA | AAA | ATG | GAG | GAA | GAA | ATT | CGA | CAA | CAG | 1050 |
| Ala 260 | Glu | Leu | Gly | Ser | Pro 265 | Val | Lys | Met | Glu | Glu 270 | Glu | Ile | Arg | Gln | Gln 275 | |
| AGT | GAT | GAA | GTC | CTC | ACT | GTC | ATC | AAA | GCC | AAA | GCC | CAG | TGG | CCA | TCC | 1098 |
| Ser | Asp | Glu | Val | Leu 280 | Thr | Val | Ile | Lys | Ala 285 | Lys | Ala | Gln | Trp | Pro 290 | Ser | |
| TGG | CAG | CCT | GTC | AAT | GTG | AGA | GCA | GCA | CCC | TCA | GCC | GAA | TTC | TCA | GTG | 1146 |
| Trp | Gln | Pro | Val 295 | Asn | Val | Arg | Ala | Ala 300 | Pro | Ser | Ala | Glu | Phe 305 | Ser | Val | |
| GAC | AGG | ACA | CGC | CAC | TTG | ATG | TCC | TTC | CTA | ACC | ATG | ATG | GGC | CCC | AGT | 1194 |
| Asp | Arg | Thr 310 | Arg | His | Leu | Met | Ser 315 | Phe | Leu | Thr | Met | Met 320 | Gly | Pro | Ser | |
| CCT | GAC | TGG | AAC | GTG | GGC | CTA | TCT | GCA | GAG | GAT | CTG | TGC | ACC | AAG | GAG | 1242 |
| Pro | Asp | Trp | Asn 325 | Val | Gly | Leu | Ser | Ala 330 | Glu | Asp | Leu | Cys | Thr 335 | Lys | Glu | |
| TGT | GGC | TGG | GTC | CAG | AAA | GTG | GTG | CAG | GAC | CTA | ATT | CCC | TGG | GAT | GCT | 1290 |
| Cys | Gly 340 | Trp | Val | Gln | Lys | Val 345 | Val | Gln | Asp | Leu | Ile 350 | Pro | Trp | Asp | Ala 355 | |
| GGC | ACG | GAC | AGC | GGG | GTG | ACC | TAC | GAG | TCA | CCA | AAC | AAG | CCC | ACA | ATT | 1338 |
| Gly | Thr | Asp | Ser | Gly 360 | Val | Thr | Tyr | Glu | Ser 365 | Pro | Asn | Lys | Pro | Thr 370 | Ile | |
| CCT | CAG | GAA | AAA | ATC | CGA | CCC | CTG | ACT | AGT | CTG | GAC | CAT | CCT | CAG | AGT | 1386 |
| Pro | Gln | Glu | Lys 375 | Ile | Arg | Pro | Leu | Thr 380 | Ser | Leu | Asp | His | Pro 385 | Gln | Ser | |
| CCT | TTC | TAT | GAC | CCG | GAA | GGT | GGG | TCC | ATC | ACA | CAA | GTG | GCC | AGA | GTC | 1434 |
| Pro | Phe | Tyr 390 | Asp | Pro | Glu | Gly | Gly 395 | Ser | Ile | Thr | Gln | Val 400 | Ala | Arg | Val | |
| GTC | ATC | GAG | AGA | ATT | GCC | CGG | AAG | GGA | GAA | CAA | TGC | AAC | ATT | GTA | CCT | 1482 |
| Val | Ile | Glu | Arg 405 | Ile | Ala | Arg | Lys | Gly 410 | Glu | Gln | Cys | Asn | Ile 415 | Val | Pro | |
| GAC | AAT | GTG | GAT | GAT | ATT | GTA | GCC | GAC | CTG | GCT | CCA | GAA | GAG | AAA | GAT | 1530 |
| Asp | Asn | Val | Asp 420 | Asp | Ile | Val | Ala | Asp 425 | Leu | Ala | Pro | Glu | Glu 430 | Lys | Asp 435 | |
| GAA | GAT | GAC | ACC | CCT | GAA | ACC | TGC | ATC | TAC | TCC | AAC | TGG | TCC | CCA | TGG | 1578 |
| Glu | Asp | Asp | Thr | Pro 440 | Glu | Thr | Cys | Ile | Tyr 445 | Ser | Asn | Trp | Ser | Pro 450 | Trp | |
| TCG | GCC | TGC | AGC | TCT | TCC | ACT | TGT | GAA | AAG | GGT | AAG | AGG | ATG | CGG | CAA | 1626 |
| Ser | Ala | Cys | Ser 455 | Ser | Ser | Thr | Cys | Glu 460 | Lys | Gly | Lys | Arg | Met 465 | Arg | Gln | |
| CGC | ATG | CTG | AAG | GCA | CAG | CTG | GAC | CTC | AGT | GTC | CCC | TGT | CCT | GAC | ACC | 1674 |
| Arg | Met | Leu 470 | Lys | Ala | Gln | Leu | Asp 475 | Leu | Ser | Val | Pro | Cys 480 | Pro | Asp | Thr | |
| CAG | GAC | TTC | CAG | CCC | TGC | ATG | GGC | CCC | GGC | TGC | AGC | GAT | GAA | GAT | GGC | 1722 |
| Gln | Asp | Phe | Gln | Pro 485 | Cys | Met | Gly | Pro | Cys 490 | Gly | Cys | Ser | Asp | Glu 495 | Asp | Gly |
| TCC | ACC | TGT | ACC | ATG | TCG | GAG | TGG | ATC | ACC | TGG | TCA | CCC | TGC | AGT | GTC | 1770 |
| Ser | Thr | Cys | Thr | Met 500 | Ser | Glu | Trp | Ile | Thr 505 | Trp | Ser | Pro | Cys | Ser 510 | Val 515 | |
| TCG | TGT | GGC | ATG | GGT | ATG | AGG | TCC | CGG | GAG | AGG | TAC | GTG | AAG | CAG | TTC | 1818 |

-continued

| | | | | | | | | | | | | | | | |
|---|---|---|---|---|---|---|---|---|---|---|---|---|---|---|---|
| Ser | Cys | Gly | Met | Gly | Met | Arg | Ser | Arg | Glu | Arg | Tyr | Val | Lys | Gln | Phe |
| | | | 520 | | | | | 525 | | | | | 530 | | |

```
CCG GAA GAC GGC TCG GTG TGC ATG CTG CCC ACG GAA GAG ACA GAG AAG      1866
Pro Glu Asp Gly Ser Val Cys Met Leu Pro Thr Glu Glu Thr Glu Lys
            535             540             545

TGC ACG GTC AAC GAG GAG TGC TCT CCT AGC AGC TGC CTG GTG ACT GAG      1914
Cys Thr Val Asn Glu Glu Cys Ser Pro Ser Ser Cys Leu Val Thr Glu
        550             555             560

TGG GGT GAG TGG GAT GAC TGC AGC GCC ACC TGT GGA ATG GGC ATG AAG      1962
Trp Gly Glu Trp Asp Asp Cys Ser Ala Thr Cys Gly Met Gly Met Lys
565             570             575

AAG CGG CAC CGC ATG GTC AAG ATG AGC CCC GCG GAC GGC TCC ATG TGC      2010
Lys Arg His Arg Met Val Lys Met Ser Pro Ala Asp Gly Ser Met Cys
580             585             590             595

AAG GCG GAG ACT TCG CAG GCG GAG AAA TGC ATG ATG CCT GAG TGC CAT      2058
Lys Ala Glu Thr Ser Gln Ala Glu Lys Cys Met Met Pro Glu Cys His
            600             605             610

ACC ATC CCG TGC TTG CTG TCT CCT TGG TCC GAG TGG AGC GAC TGT AGC      2106
Thr Ile Pro Cys Leu Leu Ser Pro Trp Ser Glu Trp Ser Asp Cys Ser
        615             620             625

GTG ACC TGT GGG AAG GGC ATG CGG ACG CGC CAG CGG ATG CTC AAG TCT      2154
Val Thr Cys Gly Lys Gly Met Arg Thr Arg Gln Arg Met Leu Lys Ser
        630             635             640

CTG GCA GAG CTG GGG GAC TGT AAT GAG GAT CTG GAG CAG GCG GAG AAG      2202
Leu Ala Glu Leu Gly Asp Cys Asn Glu Asp Leu Glu Gln Ala Glu Lys
        645             650             655

TGT ATG CTG CCA GAG TGC CCC ATT GAC TGC GAA CTC AGT GAG TGG TCC      2250
Cys Met Leu Pro Glu Cys Pro Ile Asp Cys Glu Leu Ser Glu Trp Ser
660             665             670             675

CAG TGG TCT GAA TGT AAC AAG TCC TGT GGG AAA GGT CAC ATG ATT CGA      2298
Gln Trp Ser Glu Cys Asn Lys Ser Cys Gly Lys Gly His Met Ile Arg
            680             685             690

ACC CGG ACA ATC CAA ATG GAA CCT CAG TTT GGA GGT GCA CCC TGC CCA      2346
Thr Arg Thr Ile Gln Met Glu Pro Gln Phe Gly Gly Ala Pro Cys Pro
            695             700             705

GAG ACT GTG CAA CGC AAG AAG TGC CGT GCC CGG AAA TGC CTT CGC AGC      2394
Glu Thr Val Gln Arg Lys Lys Cys Arg Ala Arg Lys Cys Leu Arg Ser
        710             715             720

CCA TCG ATC CAG AAG CTG CGC TGG AGG GAG GCC CGA GAG AGC AGG AGG      2442
Pro Ser Ile Gln Lys Leu Arg Trp Arg Glu Ala Arg Glu Ser Arg Arg
725             730             735

AGT GAG CAG CTG AGG GAA GAG TCA GAT GGA GAG CAG TTC CCA GGC TGT      2490
Ser Glu Gln Leu Arg Glu Glu Ser Asp Gly Glu Gln Phe Pro Gly Cys
740             745             750             755

CGG ATG CGC CCG TGG ACA GCC TGG TCA GAG TGC ACC AAA CTG TGC GGA      2538
Arg Met Arg Pro Trp Thr Ala Trp Ser Glu Cys Thr Lys Leu Cys Gly
            760             765             770

GGT GGG ATC CAA GAA CGC TAC ATG ACT GTG AAG AAG AGG TTC AAA AGC      2586
Gly Gly Ile Gln Glu Arg Tyr Met Thr Val Lys Lys Arg Phe Lys Ser
            775             780             785

TCC CAG TTT ACC AGC TGC AAA GAC AAG AAG GAG ATC AGA GCG TGC AAC      2634
Ser Gln Phe Thr Ser Cys Lys Asp Lys Lys Glu Ile Arg Ala Cys Asn
        790             795             800

GTG CAC CCT TGT T AGTAGGGGTT CAACTCCCCA GGGCTGCATT CCAGATTCTA       2687
Val His Pro Cys
        805

GTCACCAATG GTTGGGTGGT GTATTTGCTT GTTAAGATG ATTTAAATTG TGTCCACATG     2747

TTTTCATTTT TACCGGTGTG GTTTGCCCAA TAGTCTTATG GAGGCCGAGG GACATCTTGT    2807

CTGAATACTT CTTGGTGAGT ACAGGCCAAG CGGGGCATCT TGTCCCCAGG CGCCATCTTC    2867

CTGCACTGAG TTGAGTAGTG TTGGTTCACC TTGGTACTAA ACTGAATCGT GTCCCTCTGG    2927
```

-continued

```
AGCATCCCCT GGTCAAGCAG GGTGGAGACT TTGGCCATCC ACAAGGAGAA GCAACCAGGA    2987
TGCAGCATGC GGGAGACACA GCCATTAATT GCAAAGGACA GATCCTCCTC TCTCACCTTT    3047
GGCCTGCTCA CTCTTACAGA AACCTGTTTG TCCGCCTCCT TTTTTATTTA GCACAACTCC    3107
AGGCATCTTG GTAAGTCTCC AGGGTCATGG GTTCTTCGGT GCCCTGAAGG AGAAGCCCTG    3167
AGGTGAGGTG GCATTTGTTA CAAACCTCCC AATACTGCTT TACTGGCATC ACAAGGTCAG    3227
CAGGTGATGA TGGCTACTTC ATTTCATTGT GAGCCGTGAT TTCCGTTGAG TTTTGATTGT    3287
TGGTGCCATA AATGTCCTAG GATGCTGGAC GGACACATCA GCCTTGTCAG CAGATCCTTC    3347
TTTGAGCCAA TGTAGACAGT AAGCTGGGCA CTGGTTCCAA AGCCAACTTA AATCTTCCT    3407
ACACATATCC AGACCTTTTT TTAGGTTGCC CAAACTTCCT TAGAATAAAG CATTTAGCT    3467
CTGAGAACTA CTTGATAAGT CTGCCAGGAA GCCCCAAGT CAATTCTTCA ACAAAAATAC    3527
TATCTTCCCT ACTTAATTTT TTTTAAGTCA TGATATTTTA TAGTTAGAGG AGAGAGAGAC    3587
AATCTATTCC CATGACTAAG ACACAAACCT ACAAGAAAGG GTTACTCAGT CAAGCCTGTG    3647
CCTGACTTCT GGACCAGGCC CCTGATTTTC ATGGATAGTC CAAAGGAAGG CCAGGGGTTC    3707
CCACTGACTC CAAGCCATCA GCAGCACCCA AACCCAGGAG CAACAAATAT TCAGAGAAAG    3767
AGGATGTTTA TCTCAGCTAT GAGCTCATTG GCAGGTTGTA CTCATGCATC TGTTAAAAGC    3827
ACCACCACAT CCTTTTGCAA GTCTGTTTAT TACCGCTTCA TCCAAATACA TTTTGTGGTC    3887
AAGATCGACA CAGTGCTATG AATACAGTAC TTTAAGGTCT GCATTAAACA CATCAGAATA    3947
TTTCCTGCCA CATCTATGTA CAACCCCTGA ATATGTATTT TTCCTTAACA CAAGAGAGCC    4007
TGTTCAATTA AAAAAAAAA AA                                              4029
```

( 2 ) INFORMATION FOR SEQ ID NO:10:

( i ) SEQUENCE CHARACTERISTICS:
      ( A ) LENGTH: 807 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

```
Met Arg Leu Ser Pro Ala Pro Leu Arg Leu Ser Arg Gly Pro Ala Leu
 1               5                  10                  15
Leu Ala Leu Ala Leu Pro Leu Ala Ala Ala Leu Ala Phe Ser Asp Glu
                20                  25                  30
Thr Leu Asp Lys Val Ala Lys Ser Glu Gly Tyr Cys Ser Arg Ile Leu
            35                  40                  45
Arg Ala Gln Gly Thr Arg Arg Glu Gly Tyr Thr Glu Phe Ser Leu Arg
        50                  55                  60
Val Glu Gly Asp Pro Asp Phe Tyr Lys Pro Gly Ser Ser Tyr Arg Val
 65                  70                  75                  80
Thr Leu Ser Ala Ala Pro Pro Ser Tyr Phe Arg Gly Phe Thr Leu Ile
                85                  90                  95
Ala Leu Lys Glu Asn Arg Glu Gly Asp Lys Glu Glu Asp His Ala Gly
            100                 105                 110
Thr Phe Gln Ile Ile Asp Glu Glu Thr Gln Phe Met Ser Asn Cys
        115                 120                 125
Pro Val Ala Val Thr Glu Ser Thr Pro Arg Arg Arg Thr Arg Ile Gln
        130                 135                 140
Val Phe Trp Ile Ala Pro Pro Thr Gly Thr Gly Cys Val Ile Leu Lys
145                 150                 155                 160
Ala Ser Ile Val Gln Lys Arg Ile Ile Tyr Phe Gln Asp Glu Gly Ser
```

|     |     |     | 165 |     |     |     |     | 170 |     |     |     |     | 175 |     |
|---|---|---|---|---|---|---|---|---|---|---|---|---|---|---|

Leu Thr Lys Lys Leu Cys Glu Gln Asp Pro Thr Leu Asp Gly Val Thr
            180                 185                 190

Asp Arg Pro Ile Leu Asp Cys Cys Ala Cys Gly Thr Ala Lys Tyr Arg
            195                 200                 205

Leu Thr Phe Tyr Gly Asn Trp Ser Glu Lys Thr His Pro Lys Asp Tyr
            210                 215                 220

Pro Arg Arg Ala Asn His Trp Ser Ala Ile Ile Gly Gly Ser His Ser
225                 230                 235                 240

Lys Asn Tyr Val Leu Trp Glu Tyr Gly Tyr Ala Ser Glu Gly Val
            245                 250                 255

Lys Gln Val Ala Glu Leu Gly Ser Pro Val Lys Met Glu Glu Ile
            260                 265                 270

Arg Gln Gln Ser Asp Glu Val Leu Thr Val Ile Lys Ala Lys Ala Gln
            275                 280                 285

Trp Pro Ser Trp Gln Pro Val Asn Val Arg Ala Ala Pro Ser Ala Glu
            290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                    325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
            355                 360                 365

Pro Thr Ile Pro Gln Glu Lys Ile Arg Pro Leu Thr Ser Leu Asp His
    370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
                405                 410                 415

Ile Val Pro Asp Asn Val Asp Asp Ile Val Ala Asp Leu Ala Pro Glu
            420                 425                 430

Glu Lys Asp Glu Asp Asp Thr Pro Glu Thr Cys Ile Tyr Ser Asn Trp
        435                 440                 445

Ser Pro Trp Ser Ala Cys Ser Ser Thr Cys Glu Lys Gly Lys Arg
    450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
            485                 490                 495

Glu Asp Gly Ser Thr Cys Thr Met Ser Glu Trp Ile Thr Trp Ser Pro
            500                 505                 510

Cys Ser Val Ser Cys Gly Met Gly Met Arg Ser Arg Glu Arg Tyr Val
        515                 520                 525

Lys Gln Phe Pro Glu Asp Gly Ser Val Cys Met Leu Pro Thr Glu Glu
    530                 535                 540

Thr Glu Lys Cys Thr Val Asn Glu Glu Cys Ser Pro Ser Ser Cys Leu
545                 550                 555                 560

Val Thr Glu Trp Gly Glu Trp Asp Asp Cys Ser Ala Thr Cys Gly Met
                565                 570                 575

Gly Met Lys Lys Arg His Arg Met Val Lys Met Ser Pro Ala Asp Gly
            580                 585                 590

Ser Met Cys Lys Ala Glu Thr Ser Gln Ala Glu Lys Cys Met Met Pro
        595                 600                 605

| | | | | | | | | | | | | | | |
|---|---|---|---|---|---|---|---|---|---|---|---|---|---|---|
| Glu | Cys | His | Thr | Ile | Pro | Cys | Leu | Leu | Ser | Pro | Trp | Ser | Glu | Trp | Ser |
| | 610 | | | | 615 | | | | | 620 | | | | | |
| Asp | Cys | Ser | Val | Thr | Cys | Gly | Lys | Gly | Met | Arg | Thr | Arg | Gln | Arg | Met |
| 625 | | | | | 630 | | | | | 635 | | | | | 640 |
| Leu | Lys | Ser | Leu | Ala | Glu | Leu | Gly | Asp | Cys | Asn | Glu | Asp | Leu | Glu | Gln |
| | | | | 645 | | | | | 650 | | | | | 655 | |
| Ala | Glu | Lys | Cys | Met | Leu | Pro | Glu | Cys | Pro | Ile | Asp | Cys | Glu | Leu | Ser |
| | | | 660 | | | | | 665 | | | | 670 | | | |
| Glu | Trp | Ser | Gln | Trp | Ser | Glu | Cys | Asn | Lys | Ser | Cys | Gly | Lys | Gly | His |
| | | 675 | | | | | 680 | | | | | 685 | | | |
| Met | Ile | Arg | Thr | Arg | Thr | Ile | Gln | Met | Glu | Pro | Gln | Phe | Gly | Gly | Ala |
| | 690 | | | | 695 | | | | | 700 | | | | | |
| Pro | Cys | Pro | Glu | Thr | Val | Gln | Arg | Lys | Lys | Cys | Arg | Ala | Arg | Lys | Cys |
| 705 | | | | | 710 | | | | | 715 | | | | | 720 |
| Leu | Arg | Ser | Pro | Ser | Ile | Gln | Lys | Leu | Arg | Trp | Arg | Glu | Ala | Arg | Glu |
| | | | | 725 | | | | | 730 | | | | | 735 | |
| Ser | Arg | Arg | Ser | Glu | Gln | Leu | Arg | Glu | Ser | Asp | Gly | Glu | Gln | Phe | |
| | | | 740 | | | | | 745 | | | | 750 | | | |
| Pro | Gly | Cys | Arg | Met | Arg | Pro | Trp | Thr | Ala | Trp | Ser | Glu | Cys | Thr | Lys |
| | | 755 | | | | | 760 | | | | | 765 | | | |
| Leu | Cys | Gly | Gly | Gly | Ile | Gln | Glu | Arg | Tyr | Met | Thr | Val | Lys | Lys | Arg |
| 770 | | | | | 775 | | | | | 780 | | | | | |
| Phe | Lys | Ser | Ser | Gln | Phe | Thr | Ser | Cys | Lys | Asp | Lys | Lys | Glu | Ile | Arg |
| 785 | | | | | 790 | | | | | 795 | | | | | 800 |
| Ala | Cys | Asn | Val | His | Pro | Cys | | | | | | | | | |
| | | | | 805 | | | | | | | | | | | |

(2) INFORMATION FOR SEQ ID NO:11:

(i) SEQUENCE CHARACTERISTICS:
        (A) LENGTH: 3226 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 136..2543

(xi) SEQUENCE DESCRIPTION: SEQ ID NO:11:

```
GTGTCCCTCC CTCCTCCCTC CCTCCCTCTC TCCCTCCCTC CCCGCCTGCC CCCTCCCCGC    60

CTCTCCCCTC CCCTCTCCCG CGCCGCAGCC TCCCCCGGGC CGCCCGGCGC TGCCCGAGCT   120

GTGCGGGCGC CGAGG ATG GCA GCG CGG CTG CGG CCC CTG GCC CTG CGG CTG   171
              Met Ala Ala Arg Leu Arg Pro Leu Ala Leu Arg Leu
                1               5                   10

CTG GCG CGC ACC TTC CCC TTG GTG GCG AGG GGC TTC TCC GAC GAG ACC   219
Leu Ala Arg Thr Phe Pro Leu Val Ala Arg Gly Phe Ser Asp Glu Thr
        15                  20                  25

CTG GAG AAA GCC GCC AAA TCC GAG GGC TAC TGC AGC CGG ATC CTG CGA   267
Leu Glu Lys Ala Ala Lys Ser Glu Gly Tyr Cys Ser Arg Ile Leu Arg
    30                  35                  40

GCC CAA GGC ACC AGG AGG GAA GGG TAC AAT GAA TTT AGC CTG AGG GTG   315
Ala Gln Gly Thr Arg Arg Glu Gly Tyr Asn Glu Phe Ser Leu Arg Val
45                  50                  55                  60

GAG GGC GAT CCG GAA TTC TAC AAG CCT GGG AAC AGT TAC CGC GTG ACG   363
Glu Gly Asp Pro Glu Phe Tyr Lys Pro Gly Asn Ser Tyr Arg Val Thr
                65                  70                  75
```

| | | | | | | | | | | | | | | | | |
|---|---|---|---|---|---|---|---|---|---|---|---|---|---|---|---|---|
| CTT | TCT | GCT | GCC | ACT | CCT | GCG | TAC | TTT | CGA | GGA | TTC | ACA | TTG | ATT | GCT | 411 |
| Leu | Ser | Ala | Ala<br>80 | Thr | Pro | Ala | Tyr | Phe<br>85 | Arg | Gly | Phe | Thr | Leu<br>90 | Ile | Ala | |
| CTG | AAG | GAA | GGA | AAA | GAA | GGT | GAT | AAA | GAG | GAA | GAC | CAT | GCG | GGA | ACT | 459 |
| Leu | Lys | Glu<br>95 | Gly | Lys | Glu | Gly | Asp | Lys<br>100 | Glu | Glu | Asp | His<br>105 | Ala | Gly | Thr | |
| TTT | CAG | ATC | ATA | GAT | GAA | GAA | GAG | ACG | CAG | TTC | ATG | AGC | AAT | TGT | CCC | 507 |
| Phe | Gln | Ile<br>110 | Ile | Asp | Glu | Glu<br>115 | Glu | Thr | Gln | Phe | Met<br>120 | Ser | Asn | Cys | Pro | |
| GTC | GCG | GTT | ACT | GAG | AGC | ACA | CCT | AGA | AGG | AGG | ACA | CGC | ATC | CAG | GTC | 555 |
| Val<br>125 | Ala | Val | Thr | Glu | Ser<br>130 | Thr | Pro | Arg | Arg<br>135 | Arg | Thr | Arg | Ile | Gln | Val<br>140 | |
| TTC | TGG | ACA | GCT | CCT | CCT | ACT | GGT | ACG | GGC | TGT | GTC | ATT | CTG | AAA | GCC | 603 |
| Phe | Trp | Thr | Ala | Pro<br>145 | Pro | Thr | Gly | Thr | Gly<br>150 | Cys | Val | Ile | Leu | Lys<br>155 | Ala | |
| AGT | ATT | GTG | CAG | AAG | CGC | ATT | ATT | TAT | TTT | CAG | GAC | GAG | GGT | TCT | CTC | 651 |
| Ser | Ile | Val | Gln<br>160 | Lys | Arg | Ile | Ile | Tyr<br>165 | Phe | Gln | Asp | Glu | Gly<br>170 | Ser | Leu | |
| ACC | AAA | AGA | ATC | TGT | GAA | CAA | GAT | TCA | GCC | TCT | GAA | GGT | GTG | ACT | GAC | 699 |
| Thr | Lys | Arg<br>175 | Ile | Cys | Glu | Gln | Asp<br>180 | Ser | Ala | Ser | Glu | Gly<br>185 | Val | Thr | Asp | |
| AAA | CCA | ACA | TTA | GAT | TGC | TGT | GCC | TGT | GGA | ACT | GCC | AAA | TAC | AGG | CTA | 747 |
| Lys | Pro<br>190 | Thr | Leu | Asp | Cys | Cys<br>195 | Ala | Cys | Gly | Thr | Ala<br>200 | Lys | Tyr | Arg | Leu | |
| ACG | TTT | TAT | GGA | AAT | TGG | TCG | GAA | AAA | ACA | CAT | CCC | AAA | GAC | TTT | CCT | 795 |
| Thr<br>205 | Phe | Tyr | Gly | Asn | Trp<br>210 | Ser | Glu | Lys | Thr | His<br>215 | Pro | Lys | Asp | Phe | Pro<br>220 | |
| CGG | CGC | ACC | AAC | CAT | TGG | TCT | GCG | ATC | ATT | GGT | AGC | TCT | CAC | TCA | AAG | 843 |
| Arg | Arg | Thr | Asn | His<br>225 | Trp | Ser | Ala | Ile | Ile<br>230 | Gly | Ser | Ser | His | Ser<br>235 | Lys | |
| AAC | TAC | ATC | CTT | TGG | GAG | TAT | GGA | GGG | TAT | GCT | AGT | GAA | GGT | GTC | AAG | 891 |
| Asn | Tyr | Ile | Leu<br>240 | Trp | Glu | Tyr | Gly | Gly<br>245 | Tyr | Ala | Ser | Glu | Gly<br>250 | Val | Lys | |
| CAG | GTT | GCA | GAG | CTG | GGA | TCC | CCA | GTC | AAG | ATG | GAA | GAA | GAA | ATT | CGA | 939 |
| Gln | Val | Ala | Glu<br>255 | Leu | Gly | Ser | Pro | Val<br>260 | Lys | Met | Glu | Glu<br>265 | Glu | Ile | Arg | |
| CAA | CAA | AGT | GAT | GAG | GTT | TTA | ACA | GTC | ATC | AAG | GCA | AAA | GCA | CAG | TGG | 987 |
| Gln | Gln | Ser<br>270 | Asp | Glu | Val | Leu | Thr<br>275 | Val | Ile | Lys | Ala | Lys<br>280 | Ala | Gln | Trp | |
| CCT | GCC | TGG | CAG | CCT | CTG | AAT | GTG | AGA | GCT | GCT | CCC | TCT | GCT | GAG | TTT | 1035 |
| Pro<br>285 | Ala | Trp | Gln | Pro | Leu<br>290 | Asn | Val | Arg | Ala | Ala<br>295 | Pro | Ser | Ala | Glu | Phe<br>300 | |
| TCT | GTT | GAT | CGC | CAC | CGG | CAC | CTG | ATG | TCC | TTC | CTC | ACC | ATG | CTG | GGG | 1083 |
| Ser | Val | Asp | Arg | His<br>305 | Arg | His | Leu | Met | Ser<br>310 | Phe | Leu | Thr | Met | Leu<br>315 | Gly | |
| CCC | AGT | CCC | GAC | TGG | AAT | GTG | GGC | CTG | TCT | GCT | GAG | GAC | CTC | TGC | ACC | 1131 |
| Pro | Ser | Pro | Asp<br>320 | Trp | Asn | Val | Gly | Leu<br>325 | Ser | Ala | Glu | Asp | Leu<br>330 | Cys | Thr | |
| AAG | GAC | TGT | GGC | TGG | GTT | CAG | AAA | GTC | GTG | CAG | GAT | TTA | ATC | CCC | TGG | 1179 |
| Lys | Asp | Cys<br>335 | Gly | Trp | Val | Gln | Lys<br>340 | Val | Val | Gln | Asp | Leu<br>345 | Ile | Pro | Trp | |
| GAT | GCC | GGC | ACA | GAC | AGT | GGC | GTC | ACC | TAT | GAG | TCA | CCC | AAC | AAA | CCT | 1227 |
| Asp | Ala | Gly<br>350 | Thr | Asp | Ser | Gly<br>355 | Val | Thr | Tyr | Glu | Ser<br>360 | Pro | Asn | Lys | Pro | |
| ACA | GTT | CCT | CAA | GAG | AAG | ATT | AGA | CCA | CTT | ACA | AGC | TTA | GAT | CAC | CCT | 1275 |
| Thr<br>365 | Val | Pro | Gln | Glu | Lys<br>370 | Ile | Arg | Pro | Leu | Thr<br>375 | Ser | Leu | Asp | His | Pro<br>380 | |
| CAG | AGT | CCA | TTT | TAT | GAT | CCA | GAA | GGA | GGA | TCT | ATC | AAG | CTT | GTA | GCC | 1323 |
| Gln | Ser | Pro | Phe | Tyr<br>385 | Asp | Pro | Glu | Gly | Gly<br>390 | Ser | Ile | Lys | Leu | Val | Ala<br>395 | |
| AGA | GTC | GTG | CTT | GAA | AGA | ATT | GCA | CGC | AAG | GGG | GAG | CAG | TGC | AAC | TTC | 1371 |
| Arg | Val | Val | Leu | Glu | Arg | Ile | Ala | Arg | Lys | Gly | Glu | Gln | Cys | Asn | Phe | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GTA | CCT | GAT | AAC | ATA | GAT | GAT | ATT | GTG | GCA | GAC | CTA | GCA | CCA | GAA | GAA | 1419 |
| Val | Pro | Asp<br>415 | Asn | Ile | Asp | Asp | Ile<br>420 | Val | Ala | Asp | Leu | Ala<br>425 | Pro | Glu | Glu |  |
| AAA | GAA | GAA | GAT | GAT | ACC | CCT | GAG | ACC | TGC | ATA | TAT | TCA | AAC | TGG | TCC | 1467 |
| Lys | Glu<br>430 | Glu | Asp | Asp | Thr | Pro<br>435 | Glu | Thr | Cys | Ile | Tyr<br>440 | Ser | Asn | Trp | Ser |  |
| CCC | TGG | TCA | GCC | TGC | AGC | TCC | TCT | ACC | TGT | GAG | AAG | GGC | AAG | AGG | ATG | 1515 |
| Pro<br>445 | Trp | Ser | Ala | Cys | Ser<br>450 | Ser | Ser | Thr | Cys | Glu<br>455 | Lys | Gly | Lys | Arg | Met<br>460 |  |
| AGG | CAG | AGA | ATG | CTT | AAA | GCT | CAG | CTG | GAC | CTC | AGT | GTG | CCC | TGT | CCT | 1563 |
| Arg | Gln | Arg | Met | Leu<br>465 | Lys | Ala | Gln | Leu | Asp<br>470 | Leu | Ser | Val | Pro | Cys<br>475 | Pro |  |
| GAT | ACC | CAA | GAT | TTT | CAG | CCA | TGC | ATG | GGT | CCA | GGC | TGC | AGT | GAT | GAA | 1611 |
| Asp | Thr | Gln | Asp<br>480 | Phe | Gln | Pro | Cys | Met<br>485 | Gly | Pro | Gly | Cys | Ser<br>490 | Asp | Glu |  |
| GAT | GGT | TCA | ACT | TGC | ATG | ATG | TCT | GAC | TGG | ATT | ACA | TGG | TCC | CCC | TGT | 1659 |
| Asp | Gly | Ser<br>495 | Thr | Cys | Met | Met | Ser<br>500 | Asp | Trp | Ile | Thr | Trp<br>505 | Ser | Pro | Cys |  |
| AGT | GTT | TCC | TGT | GGA | ATG | GGA | ACG | CGA | TCT | AGA | GAG | AGA | TAT | GTA | AAG | 1707 |
| Ser | Val | Ser<br>510 | Cys | Gly | Met | Gly<br>515 | Thr | Arg | Ser | Arg | Glu<br>520 | Arg | Tyr | Val | Lys |  |
| CAA | TTC | CCC | GAA | GAT | GGC | TCT | ATG | TGC | AAA | GTG | CCT | ACT | GAA | GAA | ACT | 1755 |
| Gln<br>525 | Phe | Pro | Glu | Asp | Gly<br>530 | Ser | Met | Cys | Lys | Val<br>535 | Pro | Thr | Glu | Glu | Thr<br>540 |  |
| GAG | AAA | TGT | ATT | GTA | AAT | GAG | GAA | TGC | TCC | CCT | AGC | AGC | TGC | CTT | GTC | 1803 |
| Glu | Lys | Cys | Ile | Val<br>545 | Asn | Glu | Glu | Cys | Ser<br>550 | Pro | Ser | Ser | Cys | Leu<br>555 | Val |  |
| ACC | GAA | TGG | GGA | GAG | TGG | GAT | GAA | TGC | AGT | GCT | AGC | TGT | GGC | ACA | GGA | 1851 |
| Thr | Glu | Trp | Gly<br>560 | Glu | Trp | Asp | Glu | Cys<br>565 | Ser | Ala | Ser | Cys | Gly<br>570 | Thr | Gly |  |
| ATG | AAA | AGG | CGA | CAC | AGA | ATG | ATC | AAG | ATG | ACT | CCT | GCT | GAT | GGA | TCT | 1899 |
| Met | Lys | Arg<br>575 | Arg | His | Arg | Met | Ile<br>580 | Lys | Met | Thr | Pro | Ala<br>585 | Asp | Gly | Ser |  |
| ATG | TGC | AAG | GCA | GAA | ACT | ACA | GAG | GCA | GAG | AAA | TGC | ATG | ATG | CCC | GAA | 1947 |
| Met | Cys<br>590 | Lys | Ala | Glu | Thr | Thr<br>595 | Glu | Ala | Glu | Lys | Cys<br>600 | Met | Met | Pro | Glu |  |
| TGC | CAT | ACT | ATT | CCC | TGC | CTT | CTA | TCC | CCA | TGG | TCT | GAA | TGG | AGC | GAC | 1995 |
| Cys<br>605 | His | Thr | Ile | Pro | Cys<br>610 | Leu | Leu | Ser | Pro | Trp<br>615 | Ser | Glu | Trp | Ser | Asp<br>620 |  |
| TGC | AGC | GTG | ACA | TGT | GGG | AAG | GGA | ATG | CGA | ACC | CGG | CAA | AGG | ATG | CTG | 2043 |
| Cys | Ser | Val | Thr | Cys<br>625 | Gly | Lys | Gly | Met | Arg<br>630 | Thr | Arg | Gln | Arg | Met<br>635 | Leu |  |
| AAA | TCT | GCA | GCT | GAG | CTT | GGA | GAC | TGC | AAT | GAG | GAA | CTG | GAG | CAA | GCA | 2091 |
| Lys | Ser | Ala | Ala<br>640 | Glu | Leu | Gly | Asp | Cys<br>.645 | Asn | Glu | Glu | Leu | Glu<br>650 | Gln | Ala |  |
| GAG | AAA | TGC | ATG | CTA | CCT | GAA | TGC | CCC | ATT | GAC | TGT | GAG | CTA | ACG | GAG | 2139 |
| Glu | Lys<br>655 | Cys | Met | Leu | Pro | Glu<br>660 | Cys | Pro | Ile | Asp | Cys<br>665 | Glu | Leu | Thr | Glu |  |
| TGG | TCC | CAG | TGG | TCC | GAG | TGC | AAT | ACC | TCC | TGT | GGG | AAG | GGC | CAC | ATG | 2187 |
| Trp | Ser<br>670 | Gln | Trp | Ser | Glu | Cys<br>675 | Asn | Thr | Ser | Cys | Gly<br>680 | Lys | Gly | His | Met |  |
| ATC | AGA | ACA | AGA | ATG | ATC | AAA | ATA | GAA | CCA | CAG | TTT | GGA | GGA | ACA | GCA | 2235 |
| Ile<br>685 | Arg | Thr | Arg | Met | Ile<br>690 | Lys | Ile | Glu | Pro | Gln<br>695 | Phe | Gly | Gly | Thr | Ala<br>700 |  |
| TGC | CCA | GAA | ACT | GTC | CAA | CGT | ACT | AAA | TGT | CGA | GTA | AGG | AAA | TGC | CTG | 2283 |
| Cys | Pro | Glu | Thr | Val<br>705 | Gln | Arg | Thr | Lys | Cys<br>710 | Arg | Val | Arg | Lys | Cys<br>715 | Leu |  |
| AGA | GGC | CCA | GGT | ATG | GAA | AAG | AGG | CGT | TGG | AAG | GAG | GCC | CGG | GAG | AAA | 2331 |
| Arg | Gly | Pro | Gly | Met<br>720 | Glu | Lys | Arg | Arg | Trp<br>725 | Lys | Glu | Ala | Arg | Glu<br>730 | Lys |  |

-continued

| | | | | | | | | | | | | | | | |
|---|---|---|---|---|---|---|---|---|---|---|---|---|---|---|---|
| AGA | AGA | AGT | GAA | CAA | GCA | AAA | AAA | AAT | ATT | GAT | AAT | GAG | CAA | TAT | CCA | 2379
| Arg | Arg | Ser | Glu | Gln | Ala | Lys | Lys | Asn | Ile | Asp | Asn | Glu | Gln | Tyr | Pro |
| | | 735 | | | | 740 | | | | | 745 | | | | |
| GTT | TGT | AGG | CTG | AAA | CCA | TGG | ACT | GCT | TGG | ACA | GAA | TGT | TCT | ACA | CTC | 2427
| Val | Cys | Arg | Leu | Lys | Pro | Trp | Thr | Ala | Trp | Thr | Glu | Cys | Ser | Thr | Leu |
| | 750 | | | | 755 | | | | | 760 | | | | | |
| TGT | GGA | GGT | GGA | ATT | CAG | GAG | CGC | TAC | ATG | ATG | GTA | AAG | AAG | AGG | TCC | 2475
| Cys | Gly | Gly | Gly | Ile | Gln | Glu | Arg | Tyr | Met | Met | Val | Lys | Lys | Arg | Ser |
| 765 | | | | | 770 | | | | 775 | | | | | | 780 |
| AAA | AGC | ACT | CAG | TTT | ACT | AGC | TGC | AAA | GAC | AAA | AAG | GAG | CTA | AGA | GCA | 2523
| Lys | Ser | Thr | Gln | Phe | Thr | Ser | Cys | Lys | Asp | Lys | Lys | Glu | Leu | Arg | Ala |
| | | | | 785 | | | | | 790 | | | | | 795 | |
| TGT | AAC | GTT | CAT | CCT | TGT | TA | GGAAAACACA | AGGCTTCCAA | GTGATGCACT | | | | | | | 2573
| Cys | Asn | Val | His | Pro | Cys | | | | | | | | | | |
| | | | 800 | | | | | | | | | | | | |

CTGAGCTATA AGGAAAGTCA ACCTTGGTTT GGTTTTTAAA ACAAACAAAA GTATAAAGTG 2633

TATATTAGTT TTCATTTTTG CAGTGTGGTT TGCTTTTAGT CTTGCTGGTG CAAGAAATAT 2693

ATTTTATAAA TATTTCCTCC GATTAATCTA GGTAAACTTT GATGCTCCAG CTAGCCCTTA 2753

CTGCATAAAA ATAGTAGGTC ATTGTGAGTC ATTAACTGA AGTACAGACA TATCTGTGGA 2813

CATGGAATAG CCATATAGAA ATACTACTTG TAAAGACATG GGATGCATGC ATATTAACAT 2873

AACTAATTTG AAGTGACATG TTTCATATGT GGGAGGATTT CTCTCTTGAT TTGATTTAAA 2933

AATCCAAAGC AGTGCCTATG TGATTATACA ACTATGCCAA GGAGAAATTT CAGTAATGCT 2993

GGTTCAATAA TATTAAAGGT GCATGTTTAT CTTTTTACAA TATTGGGTTA AGCGATAGTT 3053

GAAATAATTA CCCTACATAC TTTTGTTCAC ATGGATGCTG CGTTCCATGC AAAATCATCT 3113

TTGTTTCTCA AATAGCAACT TACTTAAATA ATCTGTGCAG CTCAATAGTG ATGTCAGCCC 3173

ATAACACAGT CACAACACAC AAAGACATGT GGCTATCACA GTACCTGTCA CTG 3226

( 2 ) INFORMATION FOR SEQ ID NO:12:

( i ) SEQUENCE CHARACTERISTICS:
        ( A ) LENGTH: 802 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Ala | Ala | Arg | Leu | Arg | Pro | Leu | Ala | Leu | Arg | Leu | Leu | Ala | Arg | Thr |
| 1 | | | | 5 | | | | | 10 | | | | | 15 |
| Phe | Pro | Leu | Val | Ala | Arg | Gly | Phe | Ser | Asp | Glu | Thr | Leu | Glu | Lys | Ala |
| | | | 20 | | | | | 25 | | | | | 30 | |
| Ala | Lys | Ser | Glu | Gly | Tyr | Cys | Ser | Arg | Ile | Leu | Arg | Ala | Gln | Gly | Thr |
| | | 35 | | | | | 40 | | | | | 45 | | |
| Arg | Arg | Glu | Gly | Tyr | Asn | Glu | Phe | Ser | Leu | Arg | Val | Glu | Gly | Asp | Pro |
| | 50 | | | | | 55 | | | | | 60 | | | | |
| Glu | Phe | Tyr | Lys | Pro | Gly | Asn | Ser | Tyr | Arg | Val | Thr | Leu | Ser | Ala | Ala |
| 65 | | | | | 70 | | | | | 75 | | | | | 80 |
| Thr | Pro | Ala | Tyr | Phe | Arg | Gly | Phe | Thr | Leu | Ile | Ala | Leu | Lys | Glu | Gly |
| | | | | 85 | | | | | 90 | | | | | 95 | |
| Lys | Glu | Gly | Asp | Lys | Glu | Glu | Asp | His | Ala | Gly | Thr | Phe | Gln | Ile | Ile |
| | | | 100 | | | | | 105 | | | | | 110 | | |
| Asp | Glu | Glu | Glu | Thr | Gln | Phe | Met | Ser | Asn | Cys | Pro | Val | Ala | Val | Thr |
| | | 115 | | | | | 120 | | | | | 125 | | | |
| Glu | Ser | Thr | Pro | Arg | Arg | Arg | Thr | Arg | Ile | Gln | Val | Phe | Trp | Thr | Ala |
| | 130 | | | | | 135 | | | | | 140 | | | | |
| Pro | Pro | Thr | Gly | Thr | Gly | Cys | Val | Ile | Leu | Lys | Ala | Ser | Ile | Val | Gln |

|     |     |     |     |     |     |     |     |     |     |     |     |     |     |     |
| --- | --- | --- | --- | --- | --- | --- | --- | --- | --- | --- | --- | --- | --- | --- |
| 145 | | | | 150 | | | | | 155 | | | | 160 | |
| Lys | Arg | Ile | Ile | Tyr | Phe | Gln | Asp | Glu | Gly | Ser | Leu | Thr | Lys | Arg | Ile |
| | | | | 165 | | | | | 170 | | | | | 175 | |
| Cys | Glu | Gln | Asp | Ser | Ala | Ser | Glu | Gly | Val | Thr | Asp | Lys | Pro | Thr | Leu |
| | | | 180 | | | | | 185 | | | | | 190 | | |
| Asp | Cys | Cys | Ala | Cys | Gly | Thr | Ala | Lys | Tyr | Arg | Leu | Thr | Phe | Tyr | Gly |
| | | 195 | | | | | 200 | | | | | 205 | | | |
| Asn | Trp | Ser | Glu | Lys | Thr | His | Pro | Lys | Asp | Phe | Pro | Arg | Arg | Thr | Asn |
| | 210 | | | | | 215 | | | | | 220 | | | | |
| His | Trp | Ser | Ala | Ile | Ile | Gly | Ser | Ser | His | Ser | Lys | Asn | Tyr | Ile | Leu |
| 225 | | | | | 230 | | | | | 235 | | | | | 240 |
| Trp | Glu | Tyr | Gly | Gly | Tyr | Ala | Ser | Glu | Gly | Val | Lys | Gln | Val | Ala | Glu |
| | | | | 245 | | | | | 250 | | | | | 255 | |
| Leu | Gly | Ser | Pro | Val | Lys | Met | Glu | Glu | Ile | Arg | Gln | Gln | Ser | Asp | |
| | | | 260 | | | | | 265 | | | | | 270 | | |
| Glu | Val | Leu | Thr | Val | Ile | Lys | Ala | Lys | Ala | Gln | Trp | Pro | Ala | Trp | Gln |
| | | 275 | | | | | 280 | | | | | 285 | | | |
| Pro | Leu | Asn | Val | Arg | Ala | Ala | Pro | Ser | Ala | Glu | Phe | Ser | Val | Asp | Arg |
| | 290 | | | | | 295 | | | | | 300 | | | | |
| His | Arg | His | Leu | Met | Ser | Phe | Leu | Thr | Met | Leu | Gly | Pro | Ser | Pro | Asp |
| 305 | | | | | 310 | | | | | 315 | | | | | 320 |
| Trp | Asn | Val | Gly | Leu | Ser | Ala | Glu | Asp | Leu | Cys | Thr | Lys | Asp | Cys | Gly |
| | | | | 325 | | | | | 330 | | | | | 335 | |
| Trp | Val | Gln | Lys | Val | Val | Gln | Asp | Leu | Ile | Pro | Trp | Asp | Ala | Gly | Thr |
| | | | 340 | | | | | 345 | | | | | 350 | | |
| Asp | Ser | Gly | Val | Thr | Tyr | Glu | Ser | Pro | Asn | Lys | Pro | Thr | Val | Pro | Gln |
| | | 355 | | | | | 360 | | | | | 365 | | | |
| Glu | Lys | Ile | Arg | Pro | Leu | Thr | Ser | Leu | Asp | His | Pro | Gln | Ser | Pro | Phe |
| | 370 | | | | | 375 | | | | | 380 | | | | |
| Tyr | Asp | Pro | Glu | Gly | Gly | Ser | Ile | Lys | Leu | Val | Ala | Arg | Val | Val | Leu |
| 385 | | | | | 390 | | | | | 395 | | | | | 400 |
| Glu | Arg | Ile | Ala | Arg | Lys | Gly | Glu | Gln | Cys | Asn | Phe | Val | Pro | Asp | Asn |
| | | | | 405 | | | | | 410 | | | | | 415 | |
| Ile | Asp | Asp | Ile | Val | Ala | Asp | Leu | Ala | Pro | Glu | Glu | Lys | Glu | Glu | Asp |
| | | | 420 | | | | | 425 | | | | | 430 | | |
| Asp | Thr | Pro | Glu | Thr | Cys | Ile | Tyr | Ser | Asn | Trp | Ser | Pro | Trp | Ser | Ala |
| | | 435 | | | | | 440 | | | | | 445 | | | |
| Cys | Ser | Ser | Ser | Thr | Cys | Glu | Lys | Gly | Lys | Arg | Met | Arg | Gln | Arg | Met |
| | 450 | | | | | 455 | | | | | 460 | | | | |
| Leu | Lys | Ala | Gln | Leu | Asp | Leu | Ser | Val | Pro | Cys | Pro | Asp | Thr | Gln | Asp |
| 465 | | | | | 470 | | | | | 475 | | | | | 480 |
| Phe | Gln | Pro | Cys | Met | Gly | Pro | Gly | Cys | Ser | Asp | Glu | Asp | Gly | Ser | Thr |
| | | | | 485 | | | | | 490 | | | | | 495 | |
| Cys | Met | Met | Ser | Asp | Trp | Ile | Thr | Trp | Ser | Pro | Cys | Ser | Val | Ser | Cys |
| | | | 500 | | | | | 505 | | | | | 510 | | |
| Gly | Met | Gly | Thr | Arg | Ser | Arg | Glu | Arg | Tyr | Val | Lys | Gln | Phe | Pro | Glu |
| | | 515 | | | | | 520 | | | | | 525 | | | |
| Asp | Gly | Ser | Met | Cys | Lys | Val | Pro | Thr | Glu | Glu | Thr | Glu | Lys | Cys | Ile |
| | 530 | | | | | 535 | | | | | 540 | | | | |
| Val | Asn | Glu | Glu | Cys | Ser | Pro | Ser | Ser | Cys | Leu | Val | Thr | Glu | Trp | Gly |
| 545 | | | | | 550 | | | | | 555 | | | | | 560 |
| Glu | Trp | Asp | Glu | Cys | Ser | Ala | Ser | Cys | Gly | Thr | Gly | Met | Lys | Arg | Arg |
| | | | | 565 | | | | | 570 | | | | | 575 | |
| His | Arg | Met | Ile | Lys | Met | Thr | Pro | Ala | Asp | Gly | Ser | Met | Cys | Lys | Ala |
| | | | 580 | | | | | 585 | | | | | 590 | | |

```
Glu  Thr  Thr  Glu  Ala  Glu  Lys  Cys  Met  Met  Pro  Glu  Cys  His  Thr  Ile
          595                      600                     605

Pro  Cys  Leu  Leu  Ser  Pro  Trp  Ser  Glu  Trp  Ser  Asp  Cys  Ser  Val  Thr
     610                      615                     620

Cys  Gly  Lys  Gly  Met  Arg  Thr  Arg  Gln  Arg  Met  Leu  Lys  Ser  Ala  Ala
625                      630                     635                          640

Glu  Leu  Gly  Asp  Cys  Asn  Glu  Glu  Leu  Glu  Gln  Ala  Glu  Lys  Cys  Met
                    645                     650                     655

Leu  Pro  Glu  Cys  Pro  Ile  Asp  Cys  Glu  Leu  Thr  Glu  Trp  Ser  Gln  Trp
               660                     665                     670

Ser  Glu  Cys  Asn  Thr  Ser  Cys  Gly  Lys  Gly  His  Met  Ile  Arg  Thr  Arg
          675                     680                     685

Met  Ile  Lys  Ile  Glu  Pro  Gln  Phe  Gly  Gly  Thr  Ala  Cys  Pro  Glu  Thr
     690                      695                     700

Val  Gln  Arg  Thr  Lys  Cys  Arg  Val  Arg  Lys  Cys  Leu  Arg  Gly  Pro  Gly
705                      710                     715                          720

Met  Glu  Lys  Arg  Arg  Trp  Lys  Glu  Ala  Arg  Glu  Lys  Arg  Arg  Ser  Glu
                    725                     730                     735

Gln  Ala  Lys  Lys  Asn  Ile  Asp  Asn  Glu  Gln  Tyr  Pro  Val  Cys  Arg  Leu
               740                     745                     750

Lys  Pro  Trp  Thr  Ala  Trp  Thr  Glu  Cys  Ser  Thr  Leu  Cys  Gly  Gly  Gly
          755                     760                     765

Ile  Gln  Glu  Arg  Tyr  Met  Met  Val  Lys  Lys  Arg  Ser  Lys  Ser  Thr  Gln
     770                      775                     780

Phe  Thr  Ser  Cys  Lys  Asp  Lys  Lys  Glu  Leu  Arg  Ala  Cys  Asn  Val  His
785                      790                     795                          800

Pro  Cys ( 2 ) INFORMATION FOR SEQ ID NO:13:

( i ) SEQUENCE CHARACTERISTICS:
             ( A ) LENGTH: 1816 base pairs
             ( B ) TYPE: nucleic acid
             ( C ) STRANDEDNESS: single
             ( D ) TOPOLOGY: linear ( i i ) MOLECULE TYPE: cDNA ( i x ) FEATURE:
             ( A ) NAME/KEY: CDS
             ( B ) LOCATION: 2..1705

( x i ) SEQUENCE DESCRIPTION: SEQ ID NO:13:

T  TCA  GGT  GAA  TAT  GTT  CTT  TGG  AGT  ATG  AGA  CAA  GCC  AGT  GAT  GGT          46
   Ser  Gly  Glu  Tyr  Val  Leu  Trp  Ser  Met  Arg  Gln  Ala  Ser  Asp  Gly
   1              5                        10                      15

GTC  AAA  CAA  GTA  GCT  GAG  TTG  GGT  TCT  CCA  GTC  AAA  ATG  GAA  GAA  GAA       94
Val  Lys  Gln  Val  Ala  Glu  Leu  Gly  Ser  Pro  Val  Lys  Met  Glu  Glu  Glu
                    20                      25                      30

ATT  CGA  CAG  AAG  GGA  GAT  GAA  GTT  CTA  ACA  GTA  ATC  AAA  GCC  AAA  GCT      142
Ile  Arg  Gln  Lys  Gly  Asp  Glu  Val  Leu  Thr  Val  Ile  Lys  Ala  Lys  Ala
               35                      40                      45

CAG  TGG  CCG  GCC  TGG  CAG  CCC  CTC  AAT  GTG  AGG  GCC  GCC  CCT  TCA  GCT      190
Gln  Trp  Pro  Ala  Trp  Gln  Pro  Leu  Asn  Val  Arg  Ala  Ala  Pro  Ser  Ala
          50                      55                      60

GAG  TTC  TCT  GTG  GAC  AGA  AGC  CGT  CAC  CTG  ATG  TCA  TTT  CTG  GCC  ATG      238
Glu  Phe  Ser  Val  Asp  Arg  Ser  Arg  His  Leu  Met  Ser  Phe  Leu  Ala  Met
     65                      70                      75

ATG  GGT  CCT  AGC  CCA  GAC  TGG  AAT  GTA  GGA  CTC  ACC  TCC  GAG  GAT  CTC      286
Met  Gly  Pro  Ser  Pro  Asp  Trp  Asn  Val  Gly  Leu  Thr  Ser  Glu  Asp  Leu
```

-continued

| | | | | | | | | | | | | | | | | |
|---|---|---|---|---|---|---|---|---|---|---|---|---|---|---|---|---|
| | | 80 | | | | 85 | | | | | 90 | | | | 95 | |
| TGT | ACC | AAA | GAG | TGT | GGC | TGG | GTT | CAG | AAG | GTG | GTC | CAG | GAT | TTG | ATT | 334 |
| Cys | Thr | Lys | Glu<br>100 | Cys | Gly | Trp | Val | Gln | Lys<br>105 | Val | Val | Gln | Asp | Leu<br>110 | Ile | |
| CCA | TGG | GAT | GCA | GGC | ACT | GAC | AGT | GGG | GTA | ACC | TAC | GAG | TCT | CCA | AAC | 382 |
| Pro | Trp | Asp | Ala<br>115 | Gly | Thr | Asp | Ser | Gly<br>120 | Val | Thr | Tyr | Glu | Ser<br>125 | Pro | Asn | |
| AAG | CCC | ACC | ATT | CCC | CAG | GAT | AAA | ATC | CGA | CCT | CTG | ACA | AGT | CTG | GAT | 430 |
| Lys | Pro | Thr<br>130 | Ile | Pro | Gln | Asp | Lys<br>135 | Ile | Arg | Pro | Leu | Thr<br>140 | Ser | Leu | Asp | |
| CAC | CCA | CAA | AGC | CCT | TCT | ATG | ACC | AGA | GGT | GGG | CCA | ATC | ATA | CCT | ATA | 478 |
| His | Pro | Gln | Ser<br>145 | Pro | Ser | Met | Thr<br>150 | Arg | Gly | Gly | Pro | Ile<br>155 | Ile | Pro | Ile | |
| GCT | CGA | GTT | GTG | ATT | GAA | AGG | ATT | GCC | AGG | AAG | GGA | GAA | CAG | TGC | AAT | 526 |
| Ala<br>160 | Arg | Val | Val | Ile | Glu<br>165 | Arg | Ile | Ala | Arg | Lys<br>170 | Gly | Glu | Gln | Cys | Asn<br>175 | |
| ATT | ATA | CCC | GAC | AAC | GTG | GAT | GAC | ATA | GTA | GCA | GAT | CTG | GTA | ACG | GAA | 574 |
| Ile | Ile | Pro | Asp | Asn<br>180 | Val | Asp | Asp | Ile | Val<br>185 | Ala | Asp | Leu | Val | Thr<br>190 | Glu | |
| GAG | AAA | GAC | GAA | GAT | GAT | ACC | CCG | GAG | ACC | TGC | ATA | TAT | TCC | AAC | TGG | 622 |
| Glu | Lys | Asp | Glu<br>195 | Asp | Asp | Thr | Pro | Glu<br>200 | Thr | Cys | Ile | Tyr | Ser<br>205 | Asn | Trp | |
| TCC | CCC | TGG | TCG | GCC | TGC | AGC | TCG | GCC | ACC | TGC | GAC | AAG | GGC | AAG | CGG | 670 |
| Ser | Pro | Trp<br>210 | Ser | Ala | Cys | Ser | Ser<br>215 | Ala | Thr | Cys | Asp | Lys<br>220 | Gly | Lys | Arg | |
| ATG | AGA | CAG | CGC | ATG | TTA | AAG | GCT | CAG | TTA | GAT | CTC | AGT | GTT | CCC | TGC | 718 |
| Met | Arg | Gln | Arg | Met<br>225 | Leu | Lys | Ala | Gln | Leu<br>230 | Asp | Leu | Ser | Val<br>235 | Pro | Cys | |
| CCA | GAC | ACT | CAG | GAC | TTT | GAA | CCC | TGC | ATG | GGG | CCC | GGC | TGC | AGC | GAT | 766 |
| Pro<br>240 | Asp | Thr | Gln | Asp | Phe<br>245 | Glu | Pro | Cys | Met | Gly<br>250 | Pro | Gly | Cys | Ser | Asp<br>255 | |
| GAC | GAA | GCC | TCT | ACC | TGC | ATG | ATG | TCA | GAA | TGG | ATC | ACC | TGG | TCG | CCG | 814 |
| Asp | Glu | Ala | Ser | Thr<br>260 | Cys | Met | Met | Ser | Glu<br>265 | Trp | Ile | Thr | Trp | Ser<br>270 | Pro | |
| TGC | AGC | GCC | TCC | TGC | GGG | ATG | GGA | ATT | GAG | GTC | AGG | GAG | AGA | TAC | GTC | 862 |
| Cys | Ser | Ala | Ser<br>275 | Cys | Gly | Met | Gly | Ile<br>280 | Glu | Val | Arg | Glu | Arg<br>285 | Tyr | Val | |
| AAG | CAG | TTC | CCA | GAA | GAC | GGT | TCC | TTG | TGT | AAA | GTC | CCA | ACG | GAA | GAA | 910 |
| Lys | Gln | Phe<br>290 | Pro | Glu | Asp | Gly | Ser<br>295 | Leu | Cys | Lys | Val | Pro<br>300 | Thr | Glu | Glu | |
| ACT | GAG | AAA | TGC | ATT | GTC | AAT | GAG | GAG | TGT | GAG | CCA | AGC | AGC | TGT | ATA | 958 |
| Thr | Glu | Lys<br>305 | Cys | Ile | Val | Asn | Glu<br>310 | Glu | Cys | Glu | Pro | Ser<br>315 | Ser | Cys | Ile | |
| GTC | ACG | GAA | TGG | GCA | GAG | TGG | GAG | GAG | TGC | AGC | GCT | ACA | TGC | CGG | ATG | 1006 |
| Val | Thr<br>320 | Glu | Trp | Ala | Glu | Trp<br>325 | Glu | Glu | Cys | Ser | Ala<br>330 | Thr | Cys | Arg | Met<br>335 | |
| GGT | ATG | AAG | AAG | CGG | CAC | AGG | ATG | ATA | AAG | ATG | ACT | CCA | GCG | GAT | GGA | 1054 |
| Gly | Met | Lys | Lys | Arg<br>340 | His | Arg | Met | Ile | Lys<br>345 | Met | Thr | Pro | Ala | Asp<br>350 | Gly | |
| TCT | ATG | TGC | AAA | GCC | GAC | ACA | ACA | GAG | GTT | GAG | AAA | TGC | ATG | ATG | CCC | 1102 |
| Ser | Met | Cys<br>355 | Lys | Ala | Asp | Thr | Thr<br>360 | Glu | Val | Glu | Lys | Cys<br>365 | Met | Met | Pro | |
| GAA | TGT | CAT | ACC | ATC | CCG | TGC | GTG | TTG | TCC | CCT | TGG | TCT | GAA | TGG | AGT | 1150 |
| Glu | Cys | His<br>370 | Thr | Ile | Pro | Cys | Val<br>375 | Leu | Ser | Pro | Trp | Ser<br>380 | Glu | Trp | Ser | |
| GAT | TGC | AGC | GTT | ACC | TGT | GGC | AAA | GGC | ACC | AGA | ACC | AGA | CAG | AGA | ATG | 1198 |
| Asp | Cys<br>385 | Ser | Val | Thr | Cys | Gly<br>390 | Lys | Gly | Thr | Arg | Thr<br>395 | Arg | Gln | Arg | Met | |
| TTG | AAG | TCC | CCG | TCT | GAA | CTT | GGA | GAT | TGC | AAT | GAG | GAA | CTG | GAA | CTG | 1246 |
| Leu<br>400 | Lys | Ser | Pro | Ser | Glu<br>405 | Leu | Gly | Asp | Cys | Asn<br>410 | Glu | Glu | Leu | Glu<br>415 | Leu | |

| | | | | | | | | | | | | | | | | |
|---|---|---|---|---|---|---|---|---|---|---|---|---|---|---|---|---|
| AAA | CAA | GTG | GAA | AAG | TGC | ATG | CTT | CCT | GAA | TGC | CCT | ATA | AGC | TGT | GAA | 1294 |
| Lys | Gln | Val | Glu | Lys | Cys | Met | Leu | Pro | Glu | Cys | Pro | Ile | Ser | Cys | Glu | |
| | | | 420 | | | | | 425 | | | | | | 430 | | |
| TTG | ACA | GAG | TGG | TCT | TAC | TGG | TCT | GAG | TGT | AAC | AAA | TGC | TCG | GGC | AAG | 1342 |
| Leu | Thr | Glu | Trp | Ser | Tyr | Trp | Ser | Glu | Cys | Asn | Lys | Cys | Ser | Gly | Lys | |
| | | | 435 | | | | | 440 | | | | | 445 | | | |
| GGT | CAC | ATG | ATT | CGT | ACC | CGA | ATG | ATC | ACA | ATG | GAA | CCA | CAG | TTT | GGA | 1390 |
| Gly | His | Met | Ile | Arg | Thr | Arg | Met | Ile | Thr | Met | Glu | Pro | Gln | Phe | Gly | |
| | | 450 | | | | | 455 | | | | | 460 | | | | |
| GGA | GCC | GTC | TGT | CCG | GAA | ACC | GTG | CAA | CGC | AAA | AAA | TGC | CGA | TTA | CGT | 1438 |
| Gly | Ala | Val | Cys | Pro | Glu | Thr | Val | Gln | Arg | Lys | Lys | Cys | Arg | Leu | Arg | |
| | 465 | | | | | 470 | | | | | 475 | | | | | |
| AAA | TGT | CAA | AAA | AGT | TCC | GGG | AAT | GAG | CGA | AGG | CAT | TTA | AAG | GAT | GCC | 1486 |
| Lys | Cys | Gln | Lys | Ser | Ser | Gly | Asn | Glu | Arg | Arg | His | Leu | Lys | Asp | Ala | |
| 480 | | | | 485 | | | | | 490 | | | | | | 495 | |
| CGA | GAG | AAG | AGA | AGG | AGT | GAA | AAA | ATA | AAG | GAA | GAT | TCA | GAT | GGA | GAA | 1534 |
| Arg | Glu | Lys | Arg | Arg | Ser | Glu | Lys | Ile | Lys | Glu | Asp | Ser | Asp | Gly | Glu | |
| | | | | 500 | | | | | 505 | | | | | 510 | | |
| CAG | TAC | CCT | GTA | TGT | AAA | ATG | AAA | CCA | TGG | ACT | GCA | TGG | ACG | GAA | TGT | 1582 |
| Gln | Tyr | Pro | Val | Cys | Lys | Met | Lys | Pro | Trp | Thr | Ala | Trp | Thr | Glu | Cys | |
| | | | 515 | | | | | 520 | | | | | 525 | | | |
| ACC | AAA | TTC | TGC | GGT | GGC | GGG | ATA | CAA | GAG | CGG | TTC | ATG | ACT | GTG | AAG | 1630 |
| Thr | Lys | Phe | Cys | Gly | Gly | Gly | Ile | Gln | Glu | Arg | Phe | Met | Thr | Val | Lys | |
| | | 530 | | | | | 535 | | | | | 540 | | | | |
| AAG | AGA | TTC | AAA | AGT | TCT | CAG | TTC | ACC | AGC | TGC | AAG | GAC | AAG | AAG | GAG | 1678 |
| Lys | Arg | Phe | Lys | Ser | Ser | Gln | Phe | Thr | Ser | Cys | Lys | Asp | Lys | Lys | Glu | |
| | | 545 | | | | 550 | | | | | 555 | | | | | |
| ATC | CGG | GCT | TGC | AAT | GTC | CAT | CCA | TGT | TAACCTGCCT | | GAAAAGAGGG | | | | | 1725 |
| Ile | Arg | Ala | Cys | Asn | Val | His | Pro | Cys | | | | | | | | |
| 560 | | | | | 565 | | | | | | | | | | | |

ATTGACACTA CAATCGCAAC AGAAGTCAAT CTTTATTAGA TATTTTTTAT CATAGAATAT 1785

ATACATGTGC TTTCATTTTG CATGTACTTT T 1816

( 2 ) INFORMATION FOR SEQ ID NO:14:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Ser | Gly | Glu | Tyr | Val | Leu | Trp | Ser | Met | Arg | Gln | Ala | Ser | Asp | Gly | Val |
| 1 | | | | 5 | | | | | 10 | | | | | 15 |
| Lys | Gln | Val | Ala | Glu | Leu | Gly | Ser | Pro | Val | Lys | Met | Glu | Glu | Glu | Ile |
| | | | 20 | | | | | 25 | | | | | 30 | |
| Arg | Gln | Lys | Gly | Asp | Glu | Val | Leu | Thr | Val | Ile | Lys | Ala | Lys | Ala | Gln |
| | | 35 | | | | | 40 | | | | | 45 | | |
| Trp | Pro | Ala | Trp | Gln | Pro | Leu | Asn | Val | Arg | Ala | Ala | Pro | Ser | Ala | Glu |
| | 50 | | | | | 55 | | | | | 60 | | | |
| Phe | Ser | Val | Asp | Arg | Ser | Arg | His | Leu | Met | Ser | Phe | Leu | Ala | Met | Met |
| 65 | | | | | 70 | | | | 75 | | | | | 80 |
| Gly | Pro | Ser | Pro | Asp | Trp | Asn | Val | Gly | Leu | Thr | Ser | Glu | Asp | Leu | Cys |
| | | | 85 | | | | | 90 | | | | | 95 | |
| Thr | Lys | Glu | Cys | Gly | Trp | Val | Gln | Lys | Val | Val | Gln | Asp | Leu | Ile | Pro |
| | | | 100 | | | | | 105 | | | | | 110 | |
| Trp | Asp | Ala | Gly | Thr | Asp | Ser | Gly | Val | Thr | Tyr | Glu | Ser | Pro | Asn | Lys |
| | | | 115 | | | | | 120 | | | | | 125 | |
| Pro | Thr | Ile | Pro | Gln | Asp | Lys | Ile | Arg | Pro | Leu | Thr | Ser | Leu | Asp | His |
| | | 130 | | | | | 135 | | | | | 140 | | |

```
Pro Gln Ser Pro Ser Met Thr Arg Gly Gly Pro Ile Ile Pro Ile Ala
145                 150                 155                 160
Arg Val Val Ile Glu Arg Ile Ala Arg Lys Gly Glu Gln Cys Asn Ile
                165                 170                 175
Ile Pro Asp Asn Val Asp Asp Ile Val Ala Asp Leu Val Thr Glu Glu
            180                 185                 190
Lys Asp Glu Asp Asp Thr Pro Glu Thr Cys Ile Tyr Ser Asn Trp Ser
        195                 200                 205
Pro Trp Ser Ala Cys Ser Ser Ala Thr Cys Asp Lys Gly Lys Arg Met
    210                 215                 220
Arg Gln Arg Met Leu Lys Ala Gln Leu Asp Leu Ser Val Pro Cys Pro
225                 230                 235                 240
Asp Thr Gln Asp Phe Glu Pro Cys Met Gly Pro Gly Cys Ser Asp Asp
                245                 250                 255
Glu Ala Ser Thr Cys Met Met Ser Glu Trp Ile Thr Trp Ser Pro Cys
            260                 265                 270
Ser Ala Ser Cys Gly Met Gly Ile Glu Val Arg Glu Arg Tyr Val Lys
        275                 280                 285
Gln Phe Pro Glu Asp Gly Ser Leu Cys Lys Val Pro Thr Glu Glu Thr
290                 295                 300
Glu Lys Cys Ile Val Asn Glu Glu Cys Glu Pro Ser Ser Cys Ile Val
305                 310                 315                 320
Thr Glu Trp Ala Glu Trp Glu Glu Cys Ser Ala Thr Cys Arg Met Gly
                325                 330                 335
Met Lys Lys Arg His Arg Met Ile Lys Met Thr Pro Ala Asp Gly Ser
            340                 345                 350
Met Cys Lys Ala Asp Thr Thr Glu Val Glu Lys Cys Met Met Pro Glu
        355                 360                 365
Cys His Thr Ile Pro Cys Val Leu Ser Pro Trp Ser Glu Trp Ser Asp
    370                 375                 380
Cys Ser Val Thr Cys Gly Lys Gly Thr Arg Thr Arg Gln Arg Met Leu
385                 390                 395                 400
Lys Ser Pro Ser Glu Leu Gly Asp Cys Asn Glu Glu Leu Glu Leu Lys
                405                 410                 415
Gln Val Glu Lys Cys Met Leu Pro Glu Cys Pro Ile Ser Cys Glu Leu
            420                 425                 430
Thr Glu Trp Ser Tyr Trp Ser Glu Cys Asn Lys Cys Ser Gly Lys Gly
        435                 440                 445
His Met Ile Arg Thr Arg Met Ile Thr Met Glu Pro Gln Phe Gly Gly
    450                 455                 460
Ala Val Cys Pro Glu Thr Val Gln Arg Lys Lys Cys Arg Leu Arg Lys
465                 470                 475                 480
Cys Gln Lys Ser Ser Gly Asn Glu Arg Arg His Leu Lys Asp Ala Arg
                485                 490                 495
Glu Lys Arg Arg Ser Glu Lys Ile Lys Glu Asp Ser Asp Gly Glu Gln
            500                 505                 510
Tyr Pro Val Cys Lys Met Lys Pro Trp Thr Ala Trp Thr Glu Cys Thr
        515                 520                 525
Lys Phe Cys Gly Gly Gly Ile Gln Glu Arg Phe Met Thr Val Lys Lys
    530                 535                 540
Arg Phe Lys Ser Ser Gln Phe Thr Ser Cys Lys Asp Lys Lys Glu Ile
545                 550                 555                 560
Arg Ala Cys Asn Val His Pro Cys
                565
```

( 2 ) INFORMATION FOR SEQ ID NO:15:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Glu Thr Cys Ile Tyr Ser Asn Trp Ser Pro Trp Ser Ala Cys Ser Ser
 1               5                  10                  15
Ser Thr Cys Glu Lys Gly Lys Arg Met Arg Gln Arg Met Leu Lys Ala
            20                  25                  30
Gln Leu Asp Leu Ser Val Pro Cys Pro Asp Thr Gln Asp Phe Gln Pro
            35                  40                  45
    Cys Met Gly Pro Gly Cys Ser Asp Glu Asp Gly
        50                  55
```

( 2 ) INFORMATION FOR SEQ ID NO:16:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Ser Thr Cys Thr Met Ser Glu Trp Ile Thr Trp Ser Pro Cys Ser Val
 1               5                  10                  15
Ser Cys Gly Met Gly Met Arg Ser Arg Glu Arg Tyr Val Lys Gln Phe
            20                  25                  30
Pro Asp Gly Ser Val Cys Met Leu Pro Thr Glu Glu Thr Glu Lys Cys
            35                  40                  45
    Thr Val Asn Glu Glu Cys Ser Pro
        50                  55
```

( 2 ) INFORMATION FOR SEQ ID NO:17:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
Ser Ser Cys Leu Val Thr Glu Trp Gly Glu Trp Asp Asp Cys Ser Ala
 1               5                  10                  15
Thr Cys Gly Met Gly Met Lys Lys Arg His Arg Met Val Lys Met Ser
            20                  25                  30
Pro Ala Asp Gly Ser Met Cys Lys Ala Glu Thr Ser Gln Ala Glu Lys
            35                  40                  45
    Cys Met Met Pro Glu Cys His Thr
        50                  55
```

( 2 ) INFORMATION FOR SEQ ID NO:18:

( i ) SEQUENCE CHARACTERISTICS:
        ( A ) LENGTH: 53 amino acids
        ( B ) TYPE: amino acid
        ( C ) STRANDEDNESS: single (D) TOPOLOGY: linear (ii) MOLECULE TYPE: protein (xi) SEQUENCE DESCRIPTION: SEQ ID NO:18:

Ile Pro Cys Leu Leu Ser Pro Trp Glu Trp Ser Asp Cys Ser Val Thr
1               5                   10                  15
Cys Gly Lys Gly Met Arg Thr Arg Gln Arg Met Leu Lys Ser Leu Ala
        20                  25                  30
Glu Leu Gly Asp Cys Asn Glu Asp Leu Glu Gln Ala Glu Lys Cys Met
            35                  40                  45
    Leu Pro Glu Cys Pro
        50

(2) INFORMATION FOR SEQ ID NO:19:

(i) SEQUENCE CHARACTERISTICS:
    (A) LENGTH: 56 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:19:

Ile Asp Cys Glu Leu Ser Glu Trp Ser Gln Trp Ser Glu Cys Asn Lys
1               5                   10                  15
Ser Cys Gly Lys Gly His Met Ile Arg Thr Arg Thr Ile Gln Met Glu
        20                  25                  30
Pro Gln Phe Gly Gly Ala Pro Cys Pro Glu Thr Val Gln Arg Lys Lys
            35                  40                  45
    Cys Arg Ala Arg Lys Cys Leu Arg
        50                  55

(2) INFORMATION FOR SEQ ID NO:20:

(i) SEQUENCE CHARACTERISTICS:
    (A) LENGTH: 55 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:20:

Pro Gln Cys Arg Met Arg Pro Trp Thr Ala Trp Ser Glu Cys Thr Lys
1               5                   10                  15
Leu Cys Gly Gly Gly Ile Gln Glu Arg Tyr Met Thr Val Lys Lys Arg
        20                  25                  30
Phe Lys Ser Ser Gln Phe Thr Ser Cys Lys Asp Lys Lys Glu Ile Arg
            35                  40                  45
    Ala Cys Asn Val His Pro Cys
        50                  55

CLONING, EXPRESSION AND USES OF A NOVEL SECRETED PROTEIN, F-SPONDIN

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

The early development of the vertebrate nervous system is controlled by local cell interactions that determine the identity of specific neural cell types and the pathways of growing axons. One of the first cell types to differentiate within the embryonic nervous system is the floor plate, a small group of epithelial cells located at the ventral midline of the neural tube (Schoenwolf and Smith, 1990). The differentiation of the floor plate is induced by local, possibly contact-dependent signals from the notochord (FIG. 1) (van Straaten et al., 1988; Placzek et al., 1990c; Hatta et al., 1991). Signals that derive from the floor plate have been implicated in the control of cell identity in the neural tube and in the guidance of axons (FIG. 1) (Jessell and Dodd, 1991).

Evidence that the floor plate is a source of polarizing signals that control cell identity and pattern in the neural tube has come from experiments in chick embryos in which floor plate cells grafted next to the neural tube of host embryos give rise to additional ectopic motor neurons and to other ventral neuronal types defined by cell specific antigenic markers (Yamada et al., 1991; Placzek et al., 1991). Inversely, preventing floor plate differentiation by removing the notochord leads to the formation of a spinal cord that is devoid of motor neurons and other ventral neurons. These grafting experiments suggest that the floor plate has a central role in establishing the identity and pattern of neuronal cell types present in the ventral spinal cord. The floor plate also has limb polarizing activity when grafted into the chick wing bud, possibly through the release of morphogenically active retinoids (Wagner et al., 1990).

After the identity of spinal cord neurons has been established, the floor plate appears to provide both long-range and local guidance cues that promote the growth of axons to and across the ventral midline of the spinal cord. First, the floor plate secretes a diffusible chemoattractant which can orient the growth of axons of commissural neuron in vitro (FIG. 1) (Tessier-Lavigne et al., 1988; Placzek et al., 1990a; Tessier-Lavigne and Placzek, 1991) and may account for the homing of these axons to the floor plate in vitro (Weber, 1938; Placzek et al., 1990b; Bovolenta and Dodd, 1991; Yaginuma and Oppenheim, 1991). Second, the floor plate may contribute to the change in trajectory of commissural axons from the transverse to the longitudinal plane that occurs immediately after crossing the ventral midline (FIG. 1) (Holley and Silver, 1987; Dodd et al., 1988; Bovolenta and Dodd, 1990). In support of this proposal, genetic mutations in mice and zebrafish that result in the absence of the floor plate during embryonic development lead to errors in the pathfinding of commissural axons at the midline of the spinal cord (Bovolenta and Dodd, 1991; Bernhardt and Kuwada, 1990). Third, the floor plate may promote the fasciculation of commissural axons that occurs after they cross the midline of the spinal cord (Holley and Silver, 1987) by regulating the expression of glycoproteins of the immunoglobulin superfamily (Dodd et al., 1988; Schachner et al., 1990; Furley et al., 1990). The specialized role of the floor plate in vertebrate neural development has parallels in invertebrate organisms in that cells at the midline of the embryonic drosophila and C. elegans central nervous systems have been implicated in neural patterning and axon guidance (Klambt et al., 1991; Nambu et al., 1991; Hedgecock and Hall, 1990).

To identify molecules that may mediate the diverse functions of the floor plate during early neural development we have used subtractive hybridization techniques to isolate cDNA clones expressed selectively by the floor plate. We describe here the characterization of cDNA clones encoding a novel secreted protein, F-spondin, that is expressed at high levels by the rat floor plate during embryonic development. The predicted amino acid sequence of F-spondin reveals that the protein contains domains similar to those present in the thrombospondin and other proteins implicated in cell adhesion and neurite outgrowth. In vitro assays show that F-spondin promotes neural cell adhesion and neurite outgrowth suggesting that the secretion of this protein by the floor plate contributes to the growth and guidance of axons in the developing CNS.

The floor plate is a transient neural cell group implicated in the control of cell pattern and axonal growth in the developing vertebrate nervous system. To identify molecules that might mediate the functions of the floor plate we have used subtractive hybridization techniques to isolated and characterize floor plate-enriched cDNA clones. One such clone encodes a novel secreted protein, F-spondin, which is expressed selectively and at very high levels in the floor plate during early spinal cord development. The F-spondin gene necodes a protein of 90,000 molecular weight. The carboxyl terminal hal of the protein contains 6 repeats identified previously in thrombospondin and other proteins that have been implicated in cell adhesion and neurite outgrowth. F-spondin is expressed in the floor plate at the time that spinal axons first extend and at a lower levels in peripheral nerve. F-spondin is secreted from transfected cos cells and is also associated with the cell surface possibly by binding to the extracellular matrix. Recombinant F-spondin promotes the attachment of spinal cord and dorsal root ganglion cells and the outgrowth of neuritis form sensory neurons in vitro. These results suggest that F-spondin may contribute to the growth and guidance of axons in both the spinal cord and the peripheral nervous system.

SUMMARY OF THE INVENTION

This invention provides isolated vertebrate nucleic acid sequences encoding F-spondin. The isolated nucleic acid may be cDNA or RNA. The isolated vertebrate nucleic acid may be derived from human, rat, chicken or Xenopus.

This invention also provides a nucleic acid probe comprising a nucleic acid molecule of at least 15 nucleotides capable of specifically hybridizing with a sequence included within the sequence of a nucleic acid molecule encoding a F-spondin. The nucleic acid probe may be DNA or RNA.

This invention provides the method to obtain F-spondin nucleic acid sequence. In an embodiment, a rat F-spondin gene is isolated by substractive hybridization.

In another embodiment, a chicken F-spondin gene is isolated by screening a chicken cDNA library using a rat F-spondin probe. In a further embodiment, a Xenopus F-spondin is also isolated.

This invention further provides a host vector system for the production of a polypeptide having the biological activity of F-spondin. The isolated vertebrate F-spondin nucleic acid sequence is linked to a promoter of RNA transcription and then to a plasmid. The suitable host is a bacterial cell, insect cell, or animal cell, depending on the type of promoter and plasmid used. This invention also provides a method of producing a polypeptide having the biological activity of F-spondin, which comprises growing the selected host vector system under suitable conditions permitting production of the polypeptide and recovering the polypeptide so produced.

This invention further provides purified vertebrate F-spondin. Such purified F-spondin will be useful for adhesion and outgrowth of axons. This invention provides a method of attaching nerve cells to a matrix comprising administering effective concentration of F-spondin in the culturing medium. This invention also provides a method of stimulating growth of nerve cells comprising appropriate concentration of F-spondin in the culturing medium. This invention further provides a method of regenerating nerve cells comprising administering effective concentration of F-spondin to recipients. Finally, this invention provides a pharmaceutical composition to stimulate growth of nerve cells comprising an effective amount of purified F-spondin and a pharmaceutically acceptable carrier.

A. Preferential expression of F-spondin mRNA in E13 floor plate compared with E13 dorsal spinal cord and adult spleen. Two transcripts of 4.5 and 4.7 kb are detected in floor plate RNA.

B. NCAM, Neural Cell Adhesion Molecule, mRNA is expressed at approximately equivalent levels in E13, Embryonic Day 13, floor plate and dorsal spinal cord and PO, postnatal, (day zero) brain.

C. F-spondin mRNA is detected in blots of total RNA from adult kidney and brain but not in RNA from adult liver or sciatic nerve.

Figure 4:
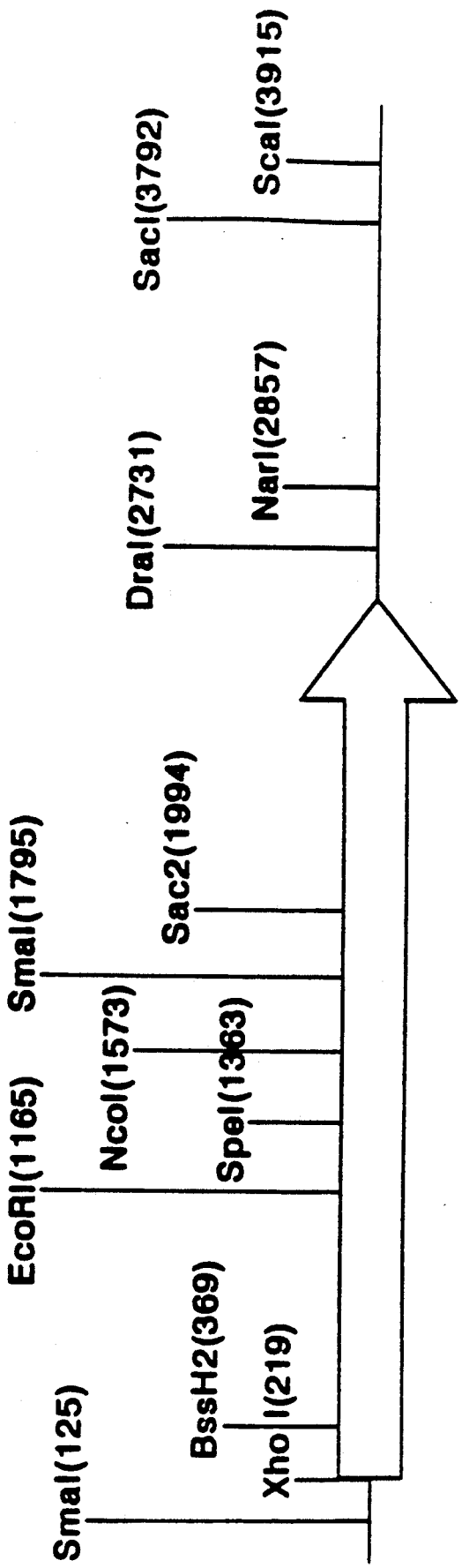

FIG. 4. Restriction map of the F-spondin cDNA. The arrow indicates the direction of translation. The restriction sites are indicated above the cDNA.

FIG. 5. cDNA and predicted amino acid sequence of F-spondin.

A1-5. Nucleotide and amino acid sequence of rat F-spondin determined from cDNA clones. The numbering of amino acids starts at the first methionine. Underlined NH$_2$ terminal residues indicate the putative signal sequence. Potential sites of N-linked glycosylation are indicated by double lines.

B. Analysis of the hydrophobicity of the predicted F-spondin amino acid sequence. The plot was generated using the parameters given in Kyte and Doolittle (1982), by a computer software MacVector, provided by IBI. The NH$_2$ terminus of the protein is to the left. Negative values indicate hydrophobic residues.

FIG. 6. Alignment of the carboxy terminal domain of F-spondin and homology to thrombospondin type one repeats in other proteins.

A. Schematic representation of the domain structure of F-spondin. The black box represents the signal sequence. The hatched box represents the thrombospondin type 1 repeats (TSRs).

B. Alignment of the six repeats in F-spondin which occupy residues 440-807 of the protein. The position of the first and last amino acids of each repeat is shown on the left. Numbers over each repeat refer to the position of residues. Positions in which there are four or more identical residues are enclosed in boxes.

C. Comparison of the conserved F-spondin motif with the conserved TSRs found in thrombospondin I, thrombospondin II, region II of the plasmodial circumsporooite (cs) proteins thrombospondin-related nonymous protein (TRAP), properdin and in the N- and C-terminal regions of the complement proteins C6, C7, C8a, C8b and C9. The number at the right of the figure indicates the number of TSR domains that contain VTCG sequence as a proportion of the total number of TSR domains.

Figure 7H:
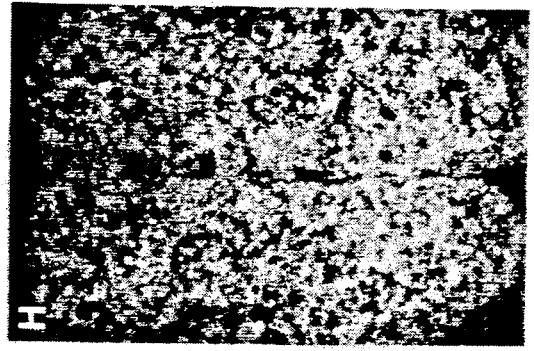
Figure 7G:

FIG. 7. Localization of F-spondin mRNA in the developing spinal cord.

A. Autoradiographic localization of F-spondin mRNA in the hindbrain of a day 10 rat embryo by in situ hybridization using an antisense RNA probe. Intense hybridization is detected at the ventral midline of the neural tube and possibly also in the axial mesoderm underlying the neural tube.

B. Localization of whole mount in situ F-spondin mRNA in E11 rat embryos by hybridization histochemistry using digoxigenin-labelled antisense probe. Hybridization is detected in the floor plate of the midbrain, hindbrain and spinal cord (arrow heads).

C. Bright field micrograph showing localization of F-spondin mRNA in E12, Emboryonic Day 12, rat spinal cord. The floor plate is intensely labelled.

D. Dark field micrograph of a similar section showing that a low level of hybridization is in the ventral horn in addition to intense labelling in the floor plate. Hybridization is also detected in the ventral root.

E. Dark field micrograph showing the floor plate and the ventral ventricular zone of E13, Embryonic Day 13, spinal cord express high levels of F-spondin mRNA.

F. Bright field micrograph of E16 spinal cord showing that F-spondin mRNA levels are still high in the floor plate and the ventral ventricular zone.

G. Dark field micrograph showing that by E16, Embryonic Day 16, significant hybridization is also detected in ventral and intermediate regions of the spinal cord.

H. Dark field micrographs showing a uniform distribution of F-spondin MRNA.

Scale bar: A=100 μm; B=350 μm; C=80 μm; E=100 μm; F=170 μm; G=170 μm; H=120μm.

FIG. 8. F-Spondin$^{myc}$ is secreted by cos cells and associated with the cell surface.

A. Position of insertion of an oligonucleotide encoding for a 10 amino acid region of the c-myc oncogene ligated into unique NcoI site or SpeI sites within the F-spondin cDNA.

B. Immunoprecipitation of conditioned media obtained by exposure for 40 h to cos cells transfected with pFp5myS, pFP5myN and to mock transfected cells. Both constructs generated a single protein band at 116 kDa.

C. Phase contact micrograph showing a small group of transfected cos cells.

D. Immunofluorescence micrograph showing the localization of F-spondin$^{myc}$ on the cell surface. Immunoreactivity is detectable at much higher levels at cell-cell rather than at cell-substrate contacts.

Scale bar in C, D=20μm

FIG. 9A-D. F-spondin$^{myc}$ promotes the extension of neurites from DRG neurons in vitro. F-spondin$^{myc}$ protein obtained from transfected cos cells supernatants was affinity purified and analyzed by SDS-PAGE(-8-25%) and silver staining. (A) Two stained bands are observed, which may reflect differences in the glycosylation of F-spondin. Neural cells isolated from E14 rat dorsal root ganglia were plated on F-spondin (B) or on cos cell-conditioned media (C) or BSA (not shown) substrates for 14 h and then fixed and labelled with MAb 3A10 and visualized by indirect immunofluorescence. (D) The length of the longest neurite of each 3A10-positive neurons was measured (or recorded as 0 mm if no neurite was seen). The percentage of neurons (ordinate) with neurites longer than a given length in μm (abscissa) is plotted. Similar results were obtained in 5 experiments. Only non-fasciculated neurites were included in the plots shown in D.

Scale bar in B and C=100 μm.

FIG. 10A-D. F-spondin promotes the adhesion of dorsal spinal cord cells. A single cell suspension of E13 dorsal spinal cord cells (10$^6$ cells/35 mm disk) was plated on, F-spondin$^{myc}$ (A, B), on BSA (C) and on F-spondin$^{myc}$ substrate in the presence of heparin (1 mg/ml)(D), for 1 h. Cells were then washed in PBS, fixed and counted.

E. Box plot showing dose-dependent adhesion of E13 dorsal spinal cord cells to different amounts of F-spondin$^{myc}$ substrate. Each box represents cell counts from 10 different fields. Similar results were obtained in 3 separate experiments.

F. Box plot showing inhibition of the adhesion of E13 dorsal spinal cord cells to F-spondin$^{myc}$ in the presence of different concentrations of heparin and chondroitin sulfate. The inhibition at all concentrations of chondroitin sulfate and heparin is significant ($p<0.001$; Ttest).

Scale bar in A, C, D=200 μm, B=50 μm.

Box plot: The box enclosed 50% of the population with the median marked as a bold line and the mean as a dot. The range of the data is indicated by the extent of the lines. Each plot represents 10 determinations from one of three similar experiments.

DETAILED DESCRIPTION OF THE INVENTION

This invention provides isolated vertebrate nucleic acid sequences which encode F-spondin. As used herein, the term F-spondin encompasses any amino acid sequence, polypeptide or protein having the biological activities provided by the F-spondin.

In one embodiment of this invention, the isolated nucleic acid sequences described hereinabove are DNA. In other embodiments of this invention, the isolated nucleic acid sequences described hereinabove are cDNA, or RNA. In preferred embodiments of this invention, the isolated nucleic sequences are cDNA as shown in sequence ID numbers (SEQ. ID Nos. 9, 11 and 13).

This invention also encompasses DNAs and cDNAs which encode amino acid sequences which differ from those of F-spondin, but which should not produce phenotypic changes. Alternatively, this invention also encompasses DNAs and cDNAS which hybridize to the DNA and cDNA of the subject invention. Hybridization methods are well known to those of skill in the art.

The DNA sequences of the subject invention also include DNA sequences coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These sequences include: the incorporation of codons "preferred" for expression by selected non-mammalian host; the provision of sites for cleavage by restriction endonuclease enzymes; and the provision of additional initial, terminal or intermediate DNA sequences that facilitate construction of readily expressed vectors.

The DNA sequence described and claimed herein are useful for the information which they provide concerning the amino acid sequence of the polypeptide and as products for the large scale synthesis of the polypeptide by a variety of recombinant techniques. The sequence is useful for generating new cloning and expression vectors, transforming and transfecting procaryotic and eucaryotic host cells, and new and useful methods for cultured growth of such host cells capable of expression of the polypeptide and related products.

Moreover, the isolated nucleic acid sequences are useful for the development of probes to study neurodevelopment.

F-spondin may be produced by a variety of vertebrates. In an embodiment, a rat F-spondin nucleic acid is isolated. A restriction map of the cDNA of rat F-spondin is shown in FIG. 4. The XhoI-DraI fragment of rat F-spondin was excised from the F-spondin cDNA. The XhoI site was blunt-ended with T4 DNA polymerase, and BglII liners (12 mers) was ligated. The fragment was subcloned into BamHl site of pBluescript SK (Strategene). The 5' of the gene is located near the T3 promoter. The resulting plasmid, pFP5/KS, encoding the rat F-spondin was deposited with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pFP5/KS was accorded ATCC designation number 75215.

In another embodiment, a chicken F-spondin cDNA was isolated (Seq. ID No. 11). The translation initiates at nucleotide position 136. In a further embodiment, a partial Xenopus F-spondin was isolated (Seq. ID No. ).

Throughout this application, references to specific nucleotides are to nucleotides present on the coding strand of the nucleic acid. The following standard abbreviations are used throughout the specification to indicate specific nucleotides:

| | |
|---|---|
| C = cytosine | A = adenosine |
| T = thymidine | G = guanosine |

For the purpose of illustration only, applicants used a substractive hybridization technique to isolate and characterize F-spondin cDNA clones in rats. Similar substractive hybridization techniques are applicable to isolate and characterize the F-spondin genes in different vertebrates.

Alternatively, the F-spondin genes may be isolated using the probe generated from the rat F-spondin gene. The chicken and Xenopus homologous F-spondin genes have recently been cloned by applicants. These genes are extremely conserved and share 90% homology at the amino acid level and about 70% homology at the nucleic acid level. The chicken gene was isolated by low stringency screening of embryonic spinal cord cDNA library whereas the Xenopus F-spondin gene was isolated by low stringency screening of the whole embryo cDNA library, both using probes from the coding region of rat F-spondin.

For the human F-spondin gene, it is conceivable that the degree of homology between rat and human would be even greater since both rats and humans are mammals. A human embryonic brain cDNA library, available from Clontech, and a human genomic library may be used for such screening. Duplicated filters of human libraries may be screened with radiolabelled probe derived from the rat F-spondin. The probe may encompass the coding region, since the homology of F-spondin across species is through the whole coding region. The filters containing the human libraries will be hybridized with the probes at low stringency (Sambrook et al. 1989) and positive clones will be further analyzed by DNA sequencing techniques which are well known to an ordinary person skilled in the art.

This invention provides a nucleic probe comprising a nucleic acid molecule of at least 15 nucleotides capable of specifically hybridizing with a sequence included within the sequence of a nucleic acid molecule encoding a F-spondin, for example, with a coding sequence included within the sequence shown in FIG. 5 and Sequence ID number 9. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes F-spondin into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

The probes are useful for 'in situ' hybridization or in order to locate tissues which express this gene, or for other hybridization assays for the presence of this gene or its mRNA in various biological tissues.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of F-spondin.

This invention further provides an isolated DNA or cDNA molecule described hereinabove wherein the host cell is selected from the group consisting of bacterial cells (such as E.coli), yeast cells, fungal cells, insect cells and animal cells. Suitable animal cells include, but are not limited to Vero cells, HeLa cells, Cos cells, CV1 cells and various primary mammalian cells.

This invention provides a method to identify and purify expressed F-spondin proteins. A myc-epitope was first introduced into the F-spondin protein. This F-spondin carrying myc-spondin may be linked to an expression vector. Such a vector may be used to transfect cells and the distribution of F-spondin in the cell can be detected by reacting myc antibodies known to be reactive to the introduced myc-epitope with the transfected cells which is expressing the F-spondin carrying myc-epitope. Taking advantage of this myc-epitope, F-spondin may be purified by an antibody affinity column which binds with this myc-epitope.

In one embodiment, a myc-epitope is introduced in the NcoI site of the rat F-spondin. After that the SmaI (125), DraI (2731) fragment of the rat F-spondin was isolated. BglII linkers were added, and the fragment was subcloned into the BamHI site of pcDNA neo (InVitrogene). The 5' end of the gene is located near the T7 RNA promoter. The resulting plasmid, pcFP5.myn, was deposited with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pcFP5.myn was accorded ATCC designation number 75216.

The above uses of the myc-epitope for identification and purification of F-spondin should not be considered limiting only to the myc-epitope. Other epitopes with specific antibodies against them which are well known to an ordinary skilled in the art could be similarly used.

Also provided by this invention are F-spondin complete protein sequences (seq. ID Nos. 10, 12). In an embodiment a complete rat F-spondin protein sequence is disclosed (Seq. ID No. 10). In another embodiment a complete chicken F-spondin protein sequence is provided (Seq. ID No. 12). In a further embodiment a partial Xenopus F-spondin protein sequence is also provided (Seq. ID No. 14). Further provided by this invention is a purified, F-spondin polypeptide. As used herein, the term "purified F-spondin" shall mean isolated naturally-occuring F-spondin or protein (purified from nature or manufactured such that the primary, secondary and tertiary conformation, and posttranslational modifications are identical to naturally-occuring material) as well as non-naturally occuring polypeptides having a primary structural conformation (i.e. continuous sequence of amino acid residues). Such polypeptides include derivatives and analogs.

Such F-spondin will be useful for adhesion and outgrowth of axon. This invention therefore provides a method of attaching nerve cells to a matrix comprising administering effective concentration of F-spondin in the culturing medium. This invention also provides a method of stimulating growth of nerve cells comprising appropriate concentration of F-spondin in the culturing medium. This invention further provides a method of regenerating nerve cells comprising administering effective concentration of F-spondin to recipients. Finally, this invention provides a pharmaceutical composition to stimulate growth of nerve cells comprising an effective amount of purified F-spondin and a pharmaceutically acceptable carrier.

This invention will be better understood from the Experimental Details which follow. However, one skilled in the art will readily appreciate that the specific methods and results discussed are merely illustrative of the invention as described more fully in the claims which follow thereafter.

Experimental Details

Experimental Procedures

Library Construction and Screening

Directional cDNA libraries were constructed in Lambda ZAP II (Stratagene) from embryonic day (E) 13 floor plate and dorsal spinal cord poly (A)+-selected RNA. The 5' ends of the cDNA inserts were located downstream of the T3 RNA polymerase promotor, and the 3' ends downstream of the T7 RNA polymerase promotor. DNA was prepared from the library using the plate lysate method (Sambrook et al., 1989). The DNA was linearised with XhoI and RNA was transcribed with T3 RNA polymerase (Stratagene). RNA from the dorsal spinal cord library was transcribed in the presence of UTP-biotin (Clontec) diluted 1:10 with UTP. First-strand cDNA was transcribed from the T3 floor plate RNA using an oligo dT XhoI linker (Stratagene).

Solution hybridization of first strand floor plate cDNA and the dorsal T3 biotinylated RNA was performed as described by Sive and St. John (1988). Approximately 1 μg of cDNA was hybridized with a 30-fold molar excess of RNA. The nucleic acids were dissolved in 10 μl of hybridization buffer containing 50 mM HEPES (pH 7.6), 0.2% SDS, 2 mM EDTA, 500 mM NaCl, and incubated at 68° C. Under these conditions, CoT values greater than 100 were obtained. The hybridization mixture was diluted to 60 μl with hybridization buffer without SDS, and 10 μg streptavidin was added. The cDNA/biotin RNA hybrids were removed by phenol-chloroform extraction. The remaining single strand cDNA was isolated and hybridized with a 300 fold excess of biotinylated RNA as described above. About 10% of the starting cDNA was recovered in the first hybridization and about 15-20% from the second hybridization.

The subtracted cDNAs were subjected to 20 cycles of a PCR reaction using oligo dT XhoI linker primer and SK primers (Stratagene). The products of the PCR reaction were cut with EcoRI and XhoI, the primers and the flanking sequences were removed with sephacryl S-300 spin columns (Pharmacia). The inserts were cloned into Lambda ZAP II arms.

Duplicate filters of the subtracted floor plate library were screened with radiolabelled first strand cDNA derived from floor plate and dorsal spinal cord. 100 ng of mRNA was incubated in 20 μl of 50 mM Tris pH 8.3, 10 mM MgCl$_2$, 150 mM KCl, 1.0 mM dGTP, 1.0 mM dTTP, 100 μCi[32p]dATP (3000 Ci/mmol), 100 μCi[$^{32}$P]dCTP (3000 Ci/mmol), 100 mg/ml oligo dT, 10 mM DTT, 10 U of RNasin (Promega), 20 U of MulV reverse transcriptase (BRL), for 30 min in 37° C. 4×10$^3$ recombinant phages were plated and screened. Hybridization and washes were performed at high stringency (Sambrook et al., 1989). The floor plate cDNA probe hybridized selectively with 24 phages. Cross hybridization analysis, revealed that these corresponded to three different cDNAs designated FP2, FP5 and FP24. The pattern of expression in the spinal cord was determined by in situ hybridization. FP2 and FP5 are expressed selectively in the floor plate while FP24 is expressed in the floor plate, roofplate and in the ventricular zone of the spinal cord. The degree of enrichment as determined by screening the floor plate enriched library and floor plate library with FP2, FP5 and FP35, which is expressed selectively in the floor plate (McKanna & Cohen, 1989) is about 50-fold.

RNA Transfer Analysis

Total RNA was prepared from various tissues using the RNA Azol method (Biotex Laboratories) and then enriched for poly (A)+ containing transcripts by passage over an oligo (dT) cellulose matrix. RNA transfer was performed as described by Thomas (1980). Probes were labelled by random priming (Feinberg and Vogelstein, 1984) and hybridized under standard conditions.

DNA Sequencing and Analysis cDNA inserts were excised directly as Bluescript plasmids (Stratagene). The nucleotide sequence of the inserts were determined by the dideoxy chain-termination method (Sanger et al., 1977) using both double-stranded and single-stranded DNA as template for T7 DNA polymerase (Sequenase, United States Biochemicals). The nucleotide sequence of the entire coding region was determined by sequencing both strands. Sequences were assembled on an Apple Macintosh computer using MacVector (IBI) program.

In Situ Hybridization

In situ hybridization was preformed as described previously (Wilkinson et al., 1987) using a T3 or T7 RNA polymerase-derived [$^{35}$S]UTP-labelled single stranded antisense RNA probe which encompasses a region of the 3' untranslated region of F-spondin (nt 3359-4029), or the TSRs (nt 1545-2626). Exposure times ranged from four to fourteen days. Sense probes were used as controls.

For whole mount in situ hybridization, E11 rat embryos were fixed in 0.1M MOPS, 2 mM EGTA, 1 mM Mg SO4, 3.7% formaldehyde for 2 hours. In situ hybridization was preformed essentially as described by Harland (1991), with a few modifications: anti-digoxygenin antibody (Boehringer Mannheim), was preabsorbed to E14 rat acetone powder (1%) (Harlow and Lane, 1988) before addition to the hybridization mixture. The chromogenic reaction was carried out for 1-2 h.

DNA Constructs

The myc epitope was introduced as follows: Two partially complementary oligonucleotides with the sequence: 5'-CTAGCGAGCAGAAGCTGATCTC-CGAGGAGGACCTCA-3' (Seq. ID No. 1) and 5'-CTAGTGAGGTCCTCCTCGGAGAT-CAGCTTCTGCTCG-3' (Seq. ID No. 2) were annealed to obtain a double-stranded DNA fragment coding for the c-myc proto-oncogene epitope EQK-LISEEDL (Seq. ID No. 3) flanked by a SpeI site. the fragment was cloned into a unique SpeI site (nt 1365) in F-spondin. The same epitope was also introduced into a NcoI site (nt 1575) using the oligonucleotides: 5'-CATGGGAGCAGAAGCTGATCTCCGAGGAG-GACCTCG-3' (Seq. ID No. 4) and 5'-CATG-CGAGGTCCTCCTCGGAGAT-CAGCTTCTGCTCC-3' (Seq. ID No. 5). The tagged F-spondin DNA was subcloned into the expression vector pMT21 (provided by Genetics Institute), or pcDNA-I (InVitrogen).

Cos Cells Transfection

Cos cells were transfected by the DEAE-Dextran method as follows: 80% confluent overnight cultures were transfected with 5 µg DNA, per 100 mm dish, in 250 µg/ml DEAE Dextran (Pharmacia), 100 mM Tris pH 7.3, in DMEM. After 6 h cells were washed and incubated in DMEM 10% calf serum, 0.1 mM choloroquine (Sigma) for 2.5 h, followed by incubation in DMEM 10% calf serum overnight. For isolation of F-spondin the medium was changed to OPTI-MEM BRL), and the cells were incubated for 48 h.

Metabolic Labeling of Cos Cells and Immunoprecipitation

Transfected cos cells were preincubated in methionine-free DMEM (BRL-GIBCO). After 1 h at 37° C., 250 µCi/ml[$^{35}$S] methionine (NEN) was added, and the cells were incubated for an additional 3 h. The medium was collected and incubated with anti-myc antibody (MAb 9E10) for 1 h. The immune complex was precipitated with fixed Staphylococcus aureus (BRL) for 1 h. Pellets were washed three times with PBS, before resuspension in 1 x sample buffer. $^{35}$S-labelled immunoprecipitated proteins were visualized after electrophoresis on 10% SDS-polyacrylamide gels.

Immunocytochemistry

F-spondin tagged with the c-myc epitope was detected with MAb 9E10 (Evan et al., 1985). Fluoresceinated isotype-specific second antibody (Boehringer Mannheim; goat antimouse IgG) was used at a dilution of 1:100. For Immunofluorescence labelling (Dodd and Jessell, 1985), cultures were washed once at 22° C. with L15 and then incubated with primary antibody for 30 min at 22° C. Cultures were then washed twice in L15-1% normal goat serum (NGS) and incubated with secondary FITC conjugated isotype-specific antibody diluted in L15-1% NGS for 30 min at 22° C. Cultures were washed twice and fixed in 4% paraformaldehyde in 0.2M phosphate buffer (PB) for 20 min, rinsed in 0.12M PB and coverslipped in 0.05% paraphenylenediamine (Sigma) in 0.2M sodium carbonate (pH 9.0); glycerol (1:1). Cultures were viewed on a Zeiss Axioplan microscope under epifluorescence optics.

Cell Culture

Spinal cords were dissected from embryonic day (E) 13 rats and placed into L15 medium at 4° C. The dorsal region of the spinal cord were dissected and incubated with 0.05 trypsin (Gibco) for 20 min in a Ca$^{2+}$/Mg$^{2+}$-free modified essential medium (S-MEM) (Gibco) supplemented with 8 mg ml$^{-1}$ glucose. The tissue was then washed with S-MEM and triturated to give a single cell suspension. Spinal cord cells were plated in 35 mm tissue culture dishes on appropriate substrates and grown in Ham's E12 medium (Gibco) supplemented with N3 additive (F12-N3) (Romijin et al., 1982) at a density of 10$^6$ cells/dish in a 5% CO2 humidified incubator at 37° C. Dorsal root ganglia were dissected from E14 rats and treated as described above. Cells were incubated with 0.1 trypsin, and plated with F12-N3 supplemented with 100 ng NGF, Neural Growth Factor, at a density of 4×10$^4$/dish.

Neurite Outgrowth Assays

5×10$^{10}$ cos cells were transfected with pFP5myN and conditioned medium was collected. F-spondin$^{myc}$, was affinity purified on a monoclonal anti-myc (9E10) affinity column. Affinity purified F-spondin$^{myc}$ (20 µl/ml) was absorbed onto nitrocellulose (Lemmon et al., 1989). For controls, parental cos cell conditioned medium was purified on the same column and used as a substrate on nitrocellulose. The nitrocellulose was then blocked with bovine serum albumin (10 mg/ml) which provided a further control for background neurite outgrowth. E14 dorsal root ganglion (DRG) neurons were plated on immobilized protein substrates at a density of 2–10×10$^4$ cells/35 mm tissue culture dish (Nunc, 35 mm diameter) and grown for 14 h. Cultures were then fixed in 4% paraformaldehyde, permeabilized with 0.1% Triton X-100 and stained using MAb 3A10 (Furley et al., 1990; available from Developmental Studies Hybridoma Bank), which recognizes a neuronal filament-associated protein and serves as a marker for fine neurites. Neuronal cell bodies and neurites were visualized by indirect immunofluorescence on a Zeiss Axioplan microscope. Neurite lengths were measured as the distance from the edge of the soma (sharply defined by 3A10 fluorescence) to the tip of its longest neurite. Neurite lengths were only measured if the entire length to the neurite could be unambiguously identified. About 25 neurites were measurable within each protein-coated area (3–4 mm$^2$).

Adhesion Assay

Dissociated E13 dorsal spinal cord cells were plated on immobilized protein substrate at a density of 10$^6$ cells/35 mm tissue culture dish (Nunc, 35 mm diameter). After one hour the cultures were washed twice with PBS and fixed in 4% paraformaldehyde. Cells were counted on a Zeiss Axioplan microscope at 400× magnification. Ten independent counts were taken from each experiment.

Experimental Results

Identification and Sequence of a Floor Plate-Enriched cDNA Clone

Figure 1A:
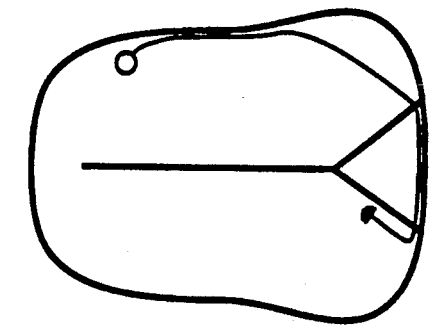
FIGS. 1A-D. Diagram showing the induction and proposed functions of the floor plate during early spinal cord development. For details see text.
Figure 1B:
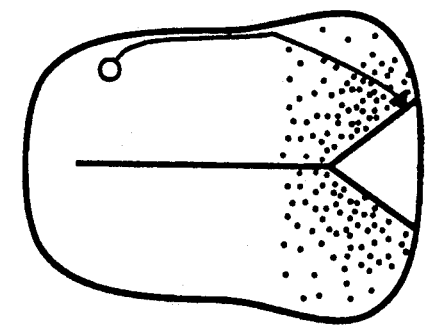
Figure 1C:
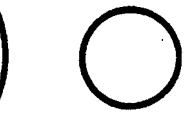
Figure 1C:
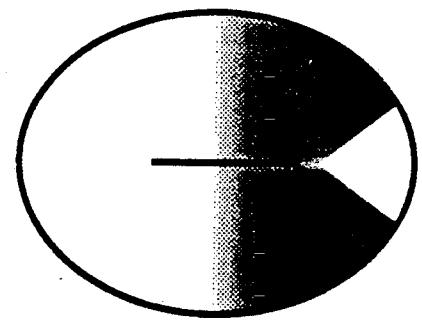
Figure 1D:
Figure 1D:
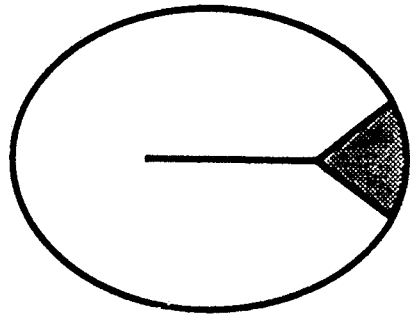
Figure 2:
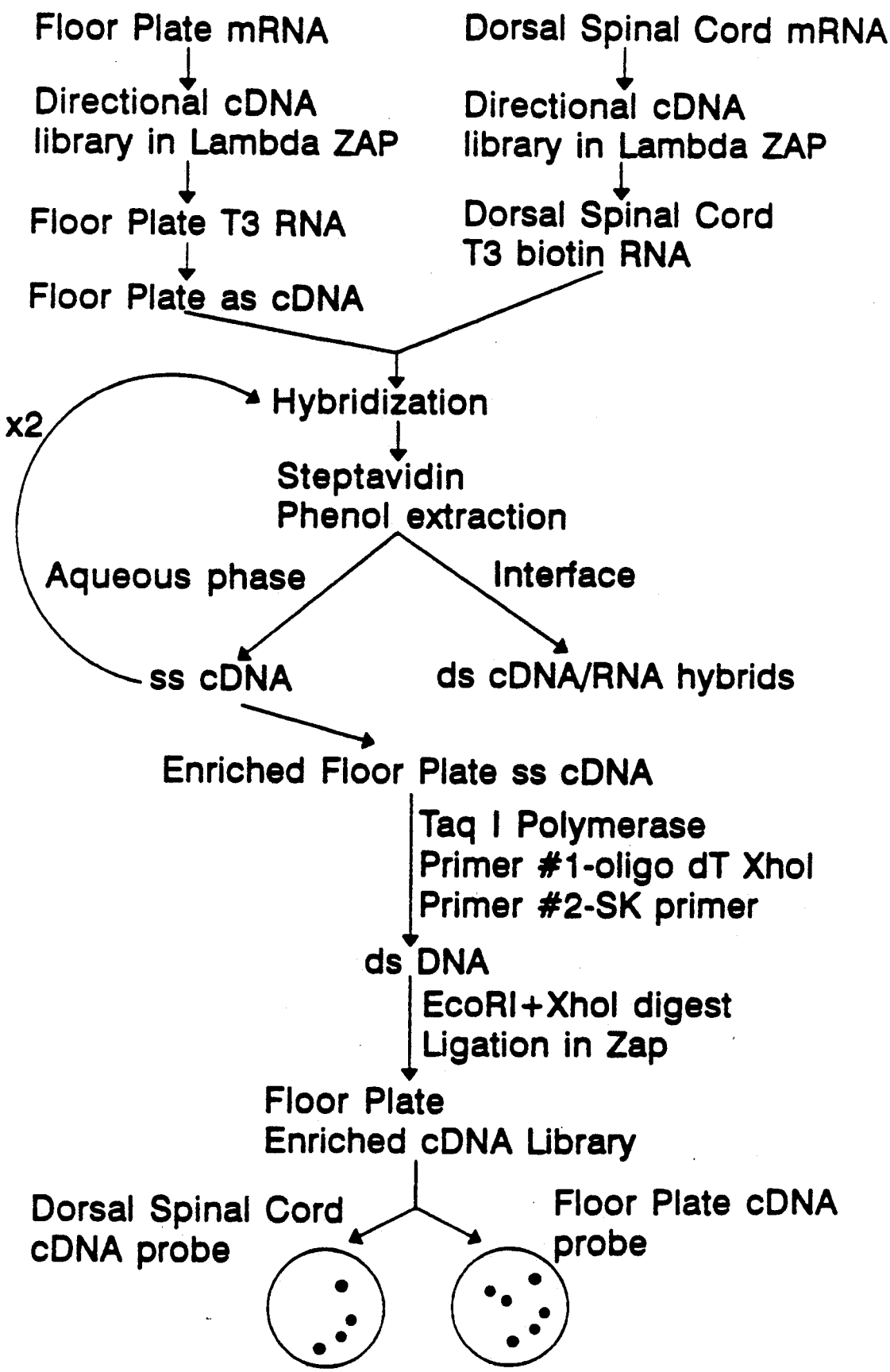
FIG. 2. Schematic diagram of the subtractive hybridization protocol used to identify floor plate specific cDNA clones. For details see text.
Figures 3A, 3B, 3C:
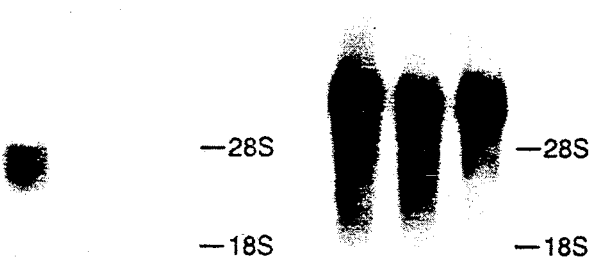
FIG. 3. Expression of F-spondin mRNA. Total cellular RNA or poly (A) RNA was isolated from different tissues and separated on 1% agarose-formaldehyde gels and blotted to nylon membranes. The blot was analyzed with cDNA probes derived from the F-spondin 3' non-coding region labelled by random priming.

Cellular assays have revealed that the floor plate has several specialized signalling functions during the embryonic development of the spinal cord. Floor plate-derived signals are likely to be encoded by proteins whose mRNAs are restricted to or are highly enriched in the floor plate. In order to identify such molecules we have used subtractive hybridization techniques to isolate cDNA clones that are expressed by the floor plate but not by the dorsal spinal cord in embryonic day (E) 13 rat embryos (see FIG. 2 and Experimental Procedures). One cDNA clone identified in this screen, designated FP5, contained a 0.5 kb insert which hybridized to two major transcripts of 4.5 and 4.7 kb in poly (A)+-selected RNA derived from E13 rat floor plate (FIG. 3A). Very faint hybridization to the same two transcripts was detected in RNA derived from E13 dorsal spinal cord (FIG. 3A) and post-natal day (P) 0 brain (FIG. 3C), whereas no hybridization was detected to RNA derived from adult liver and spleen (FIGS. 3A, C). The specificity of expression of FP5 transcripts within E13 rat spinal cord was confirmed by in situ hybridization histochemistry which showed that FP5 mRNA is expressed at very high levels in the floor plate but is undetectable in the dorsal region of E13 rat spinal cord (see below). These studies indicate that FP5 transcripts are highly enriched in the floor plate.

Screening of an E13 rat floor plate cDNA library with the 0.5 kb cDNA insert from the FP5 clone identified several additional cDNA clones of which clone FP5-9 contained a 4 kb insert. The FP5-9 cDNA contains a single long open reading frame that starts with a methionine codon at nucleotide 226 associated with a conventional translation initiation sequence (Kozak, 1984) and ends with a TGA stop codon at nucleotide 2646 (FIG. 5A). No in-frame methionine codons were found upstream of the putative translation initiation site and sequences 5' of the initiation site contain stop codons in all three reading frames. Sequencing of several other independently isolated FP5 cDNA subclones spanning the entire coding region did not reveal any differences in the nucleotide sequence of the open reading frame.

Figure 5B:
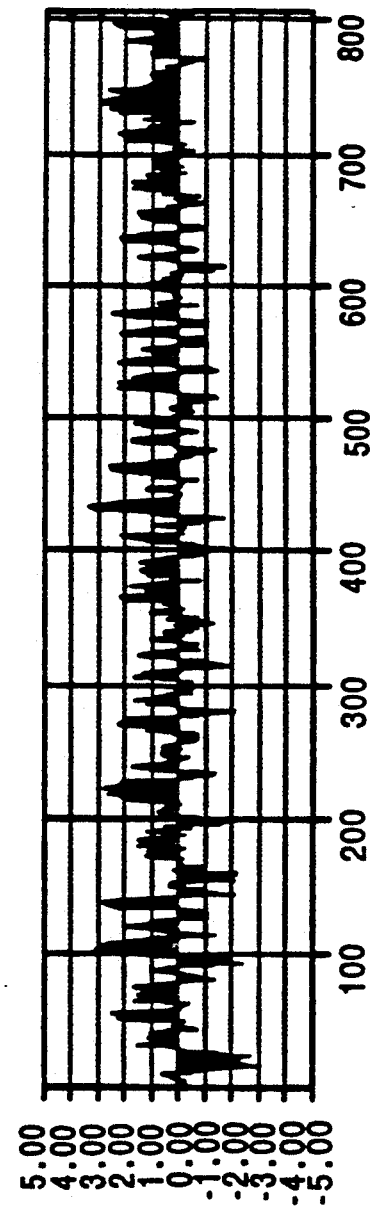

Translation of the open reading frame FP5-9 predicts a protein 807 amino acids with a molecular mass of 90,766 daltons, and N-terminal hydrophobic leader sequence (FIG. 5A; Seq. ID No. 9) with a consensus signal peptide cleavage site (von Heijne, 1985). No other long stretches of hydrophobic residues were observed (FIG. 5B) suggesting that the protein does not possess a transmembrane spanning domain. The amino terminal domain of FP5-9 contains a region of clustered basic residues (residues 138-142) which could represent a site for proteolytic processing by mammalian subtilisin-like cleavage enzymes (Steiner, 1991). In addition, the predicted protein contains three N-linked glycosylation sites (FIG. 5A). Collectively, these features suggest that the FP5-9 cDNA encodes a secreted protein.

Figure 6A:

The Protein Encoded by the FP5-9 cDNA has Structural Features of Cell and Substrate Adhesion Molecules Analysis of the predicted amino acid sequence of the FP5-9 encoded protein reveals that it is separable into two major domains (FIG. 6A). The NH2-terminal domain of 440 residues contains 10 cysteine residues and exhibits no sequence homology to other proteins in the Genbank database. The COOH terminal of the protein extends from residues 441-807 and contains six repeats of a domain 55-59 amino acids in length which can be aligned on the basis of conserved cysteine, tryptophan and arginine residues (FIGS. 6B, C).

Similar domains are present in a small number of proteins (Patthy, 1988; Smith et al., 1991). In particular, the adhesive glycoprotein encoded by the thrombospondin I and II genes (Lawler and Hynes, 1986; Bornstein et al., 1991) each possess 3 of these domains which have been designated thrombospondin type 1 repeats (TSRs) (Lawler and Hynes, 1986) (FIG. 6C). Two TSRs are found in protein C6-C9 of the alternative complement cascade, one at the NH2-terminal and one at the COOH-terminal of each protein (Haefliger et al., 1989; Smith et al., 1991). Moreover, the complement-binding protein properdin contains 6 TSRs which comprise 80% of the protein (Goundis and Reid, 1988). In addition to these vertebrate proteins, the central core of the TSR is similar to region II of malarial circumsporozoite (CS) and other plasmodial proteins (FIG. 6C) (Rich et al., 1990; Robson et al., 1988) which appear to mediate the binding of malarial sporozoites to host cells in the early stages of parasitic infection (Dame et al., 1984). Finally, two TSRs are present in the C.elegans gene Unc-5, which appears to regulate axonal pathfinding in a subset of neurons (Hedgecock et al., 1990; Culotti et al., 1991). The organization of cysteine and tryptophan residues in the TSRs of the FP5-9 encoded protein is not similar to that of the NH2-terminal TSRs of the C6-C9 complement proteins (FIG. 6B). However, the core region of the TSRs in FP5-9 (residues 14-19) is most similar to that of thrombospondin, properdin and the malarial CS proteins (FIG. 6B). We have named the FP5-9 gene F-spondin to reflect its high level of expression in the floor plate (see below) and the presence of the TSRs.

The TSRs in thrombospondin promote the adhesion of a variety of different cell types (Prater et al., 1991). Similarly, the TSR core region of the plasmodium vivax CS protein promotes the attachment of human hematopoietic cell lines in vitro (Rich et al., 1990). The amino acid sequence VTCG which is contained within this common motif appears to be critical to the cell adhesive properties of the CS proteins. A VTCG sequence (Seq. ID No. 6) is also present in the two TSRs of thrombospondin that promote cell adhesion (Prater et al., 1991). Strikingly, there is a VTCG in the fourth TSR of F-spondin and the second and third TSRs of F-spondin contain sequences (VSCG, Seq. ID No. 7; ATCG, Seq. ID No. 8) that vary by a single conservative substitution (FIG. 6B). These observations raise the possibility that the TSRs in F-spondin mediate cell adhesion. A search of the Genbank database for other proteins implicated in cell adhesion and recognition that contain a VTCG sequence identified V-CAM1 (Hession et al., 1991) and the VLA4 integrin α subunit (Takada et al., 1989).

Analysis of the predicted amino acid sequence of F-spondin reveals several other structural features that may contribute to the functional properties of the protein. The charged region that is interposed between the fifth and sixth TSRs contains the sequence LRE that has been shown to function as a neuronal cell attachment site in the extracellular matrix glycoprotein S-laminin (Hunter et al., 1989a, b). The first, third, fifth and sixth TSR's of F-spondin contain clusters of basic residues that have been implicated in the binding of proteins to heparin and other sulfated glycosaminoglycans (Cardin and Weintraub, 1989). The first, fourth and fifth TSRs of F-spondin also contain a WSXWS sequence (FIG. 6B) which is present in the variant fibronectin type III repeats found in the receptors for several growth and differentiation factors, including ciliary neurotrophic factor (CNTF), leukemia inhibitory factor (LIF) and the interleukins (ILs) 2-7 (Bazan, 1990; Davis, et al., 1991; Patthy, 1990). The function of the WSXWS motif is unclear although a mutation at this site in the IL2 receptor blocks transmembrane signalling (Miyazaki et al., 1991).

Expression Pattern of F-Spondin mRNA

Northern blot analyses of E13 embryos indicate that F-spondin is expressed at much higher levels in the floor plate than in the dorsal spinal cord. To provide more detailed information on the distribution of F-spondin we localized its mRNA in developing rat embryos by in situ hybridization. F-spondin mRNA was first detected at E10.5 in cells located at the ventral midline of the neural tube at the level of the prospective midbrain, hindbrain and spinal cord (FIG. 7A). At this stage, cells at the ventral midline of the neural tube have acquired floor plate-derived chemoattractant activity (Placzek, et al., 1990c) although no antigenic markers of floor plate differentiation can be detected. The expression of F-spondin mRNA therefore provides an early molecular marker of floor plate differentiation.

Figure 7F:
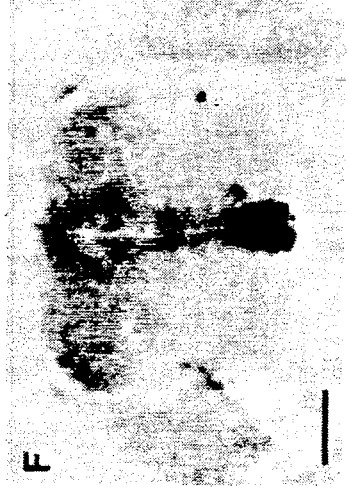

The expression of F-spondin mRNA is maintained at high levels in E11-E12 floor plate (FIG. 7B) whereas other regions of the spinal cord and hindbrain exhibit undetectable levels of hybridization at this stage. By E12-E13 low levels of mRNA are detected in the ventral horn although there is still no detectable mRNA in the dorsal horn (FIGS. 7C, D). In addition, the ventral ventricular zone immediately above the floor plate begins to express high levels of F-spondin mRNA (FIG. 7) whereas hybridization to cells in the ventricular zone in the dorsal half of the spinal cord is not detectable (FIG. 7E). Thus, expression of F-spondin mRNA reveals a molecular difference between ventricular zone cells in the dorsal and ventral spinal cord. Recent studies have suggested that the ventral ventricular zone is the site of origin of oligodendrocyte and astrocyte precursors that subsequently migrate laterally and dorsally to populate the remainder of the spinal cord (Miller, 1991). F-spondin mRNA levels remain high in the floor plate and ventral ventricular zone at E16 and by this stage significant hybridization is also detected in cells in the ventral and intermediate regions of the spinal cord (FIGS. 7F, G). By P0, the levels of F-spondin mRNA in the floor plate have decreased and there is an increase in hybridization to other cells in the spinal cord, resulting in an uniform expression of F-spondin mRNA (FIG. 7H). F-spondin mRNA is also preferentially expressed in the floor plate of the E11-E16 hindbrain and midbrain and becomes more widely expressed in the brain at later embryonic stages (not shown).

In addition to the expression of F-spondin in the embryonic CNS, from E11-E12 onwards hybridization is also detected in association with sensory and motor nerve branches that project into the periphery (FIG. 7D). The association with peripheral nerve branches suggests that F-spondin mRNA is expressed in Schwann cells. The expression of F-spondin mRNA in association with peripheral nerves persists till E16, but appears to decrease at later stages, and by P0, little or no hybridization is detected in peripheral nerve (FIG. 3C). These results provide evidence that over the period of initial outgrowth of central and peripheral axons, F-spondin mRNA is expressed predominantly by the floor plate with lower levels of expression in cells of the peripheral nerves, probably Schwann cells.

F-spondin mRNA is also expressed outside the nervous system. In particular, mesodermal cells underlying the ventral midline of the spinal cord express low levels of F-spondin mRNA from E11 (FIG. 7D). In addition, embryonic and P0 kidney (FIG. 3C), lung and condensing cartilage (not shown) expresses F-spondin mRNA. Expression of mRNA in the CNS, lung and kidney persists post-natally and in the adult (not shown).

Secretion and Cell Surface Association of F-Spondin

Figure 8A:
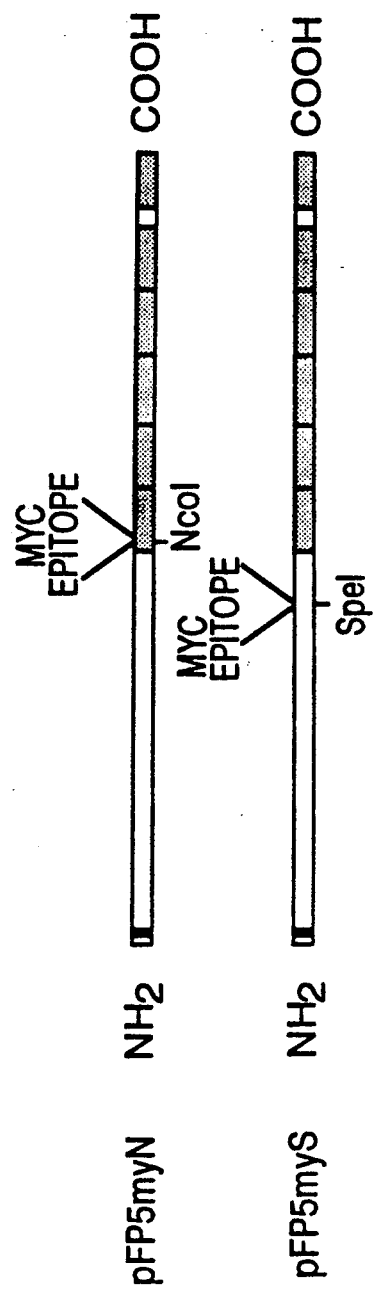
Figure 8C:
Figure 8D:
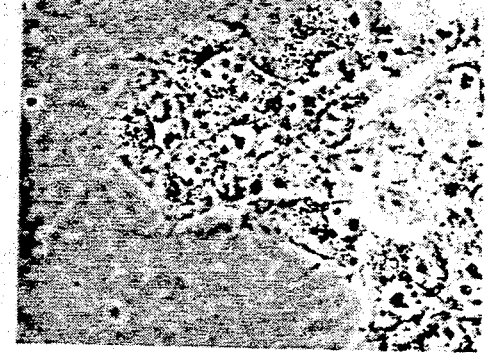
Figure 8B:
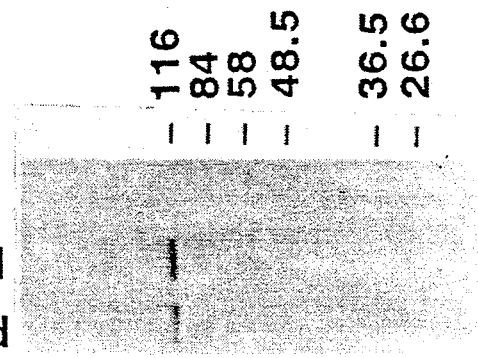
Figure 9D:
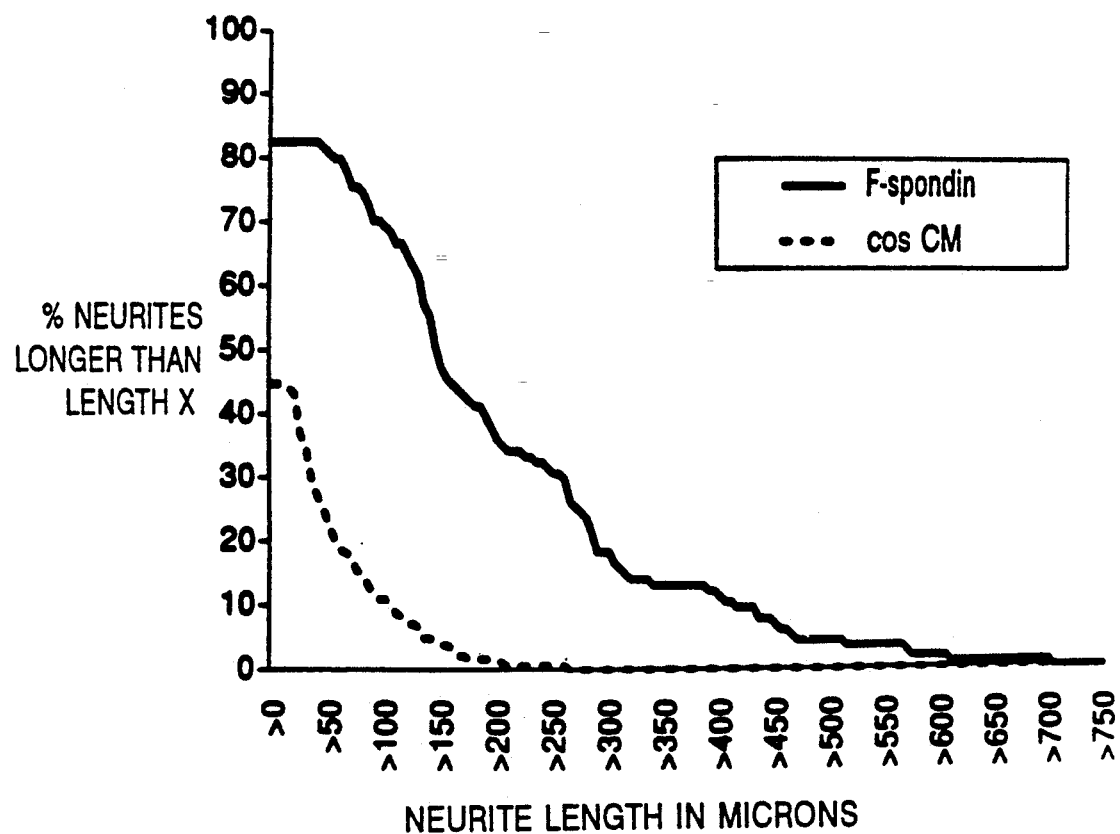

To determine the cellular localization of the F-spondin protein when expressed in mammalian cells were generated two epitope-tagged derivatives, F-spondin-$^{myc}$, each of which contain a 10 amino acid insert derived from the human c-myc proto-oncogene that can be detected by MAb 9E10 (Evan et al., 1985) (FIG. 8A). The cDNAs encoding F-spondin$^{myc}$ were cloned into a mammalian expression vector and transfected into cos cells. To examine whether F-spondin$^{myc}$ is present in medium conditioned by transfected cells we labelled cos cells with $^{35}$S-methionine for 3-4 h and immunoprecipitated released proteins with MAb 9E10. Immunoprecipitates from cos cells transfected with two different F-spondin$^{myc}$ constructs revealed a single major band of -116 kDa that was absent from mock-transfected cells (FIG. 8B). Immunoprecipitation of proteins extracted from the cos cells indicated that the amount of F-spondin recovered from the medium was similar to that associated with the cells (not shown). Thus cos cells release a significant fraction of synthesized F-spondin$^{myc}$. Other myc epitope-tagged proteins, for example the drosophila wingless protein, are synthesized by cos cells but are not detected in the medium (K. Basler, Personal communication) suggesting that the presence of F-spondin$^{myc}$ in the medium does not result from leakage from damaged cells. Thus, under these in vitro conditions F-spondin$^{myc}$ is secreted from cells. The apparent molecular weight of F-spondin determined by SDS-PAGE (-116kDa) is significantly greater than that predicted from the amino acid sequence (-90kDa). This difference in molecular weight may derive, in part, from glycoslyation of the core protein.

The cellular localization of F-spondin$^{myc}$ in transfected cos cells was also determined by immunocytochemistry. High levels of immunoreactivity were associated with the cell surface (FIGS. 8C, D) with both F-spondin$^{myc}$ constructs (FIG. 8A). No immunoreactivity was detected on the surface of untransfected cos cells (not shown). The absence of a membrane spanning region and the presence of multiple heparin attachment sites in F-spondin suggests that the cell surface association of F-spondin$^{myc}$ involves the binding of the secreted protein to the cell surface or extracellular matrix. In support of this, F-spondin$^{myc}$ present in the medium removed from transfected cos cells was found to bind to the surface of untransfected cos cells in vitro (not shown).

F-Spondin Promotes Neural Cell Adhesion and Neurite Outgrowth in vitro

The structural features of F-spondin combined with its secretion and association with the cell surface raise the possibility that F-spondin can promote the adhesion of neural cells and the outgrowth of axons. Since F-spondin is expressed at highest levels in the floor plate, we examined the effect of F-spondin on the adhesion and outgrowth of dorsal spinal cord cells to include the population of commissural neurons that project to and across the floor plate. In addition, the expression of F-spondin mRNA in peripheral nerve led us to examine whether dorsal root ganglion (DRG) neurons adhere to and extend neurites on F-spondin.

The F-spondin$^{myc}$ protein was purified on a MAb 9E10 affinity column from medium exposed to transfected cos cells (FIG. 9A) and immobilized onto a nitrocellulose substrate (Lemmon et al., 1989). The ability of F-spondin$^{myc}$ to promote the outgrowth of E14 DRG neurons was compared with that of MAb 9E10 affinity-purified proteins secreted from untransfected cos cells and BSA. Outgrowth of DRG neurons on EHS laminin was used as a positive control. Over 80% of DRG neurons extended neurites on F-spondin (FIGS. 9B, D) and the length of DRG neurites that extended on F-spondin was similar to that on laminin (not shown) and significantly greater than that on parental cos cell proteins and on BSA (FIGS. 9C, D). Similar results were obtained with both versions of F-spondin$^{myc}$ (not shown) In addition, the number of DRG neurons that adhered to a substrate of F-spondin$^{myc}$ after 18 h was about 3 fold greater than that to BSA and parental cos cell proteins, and similar to that on laminin (not shown). These observations provide evidence that F-spondin can promote the adhesion of DRG neurons and the extension of neurites in vitro. The expression of F-spondin by peripheral nerve cells in vivo occurs before many sensory neurons have extended peripheral projections and could therefore contribute to the growth of developing sensory axons in the peripheral nervous system.

Figure 10E:
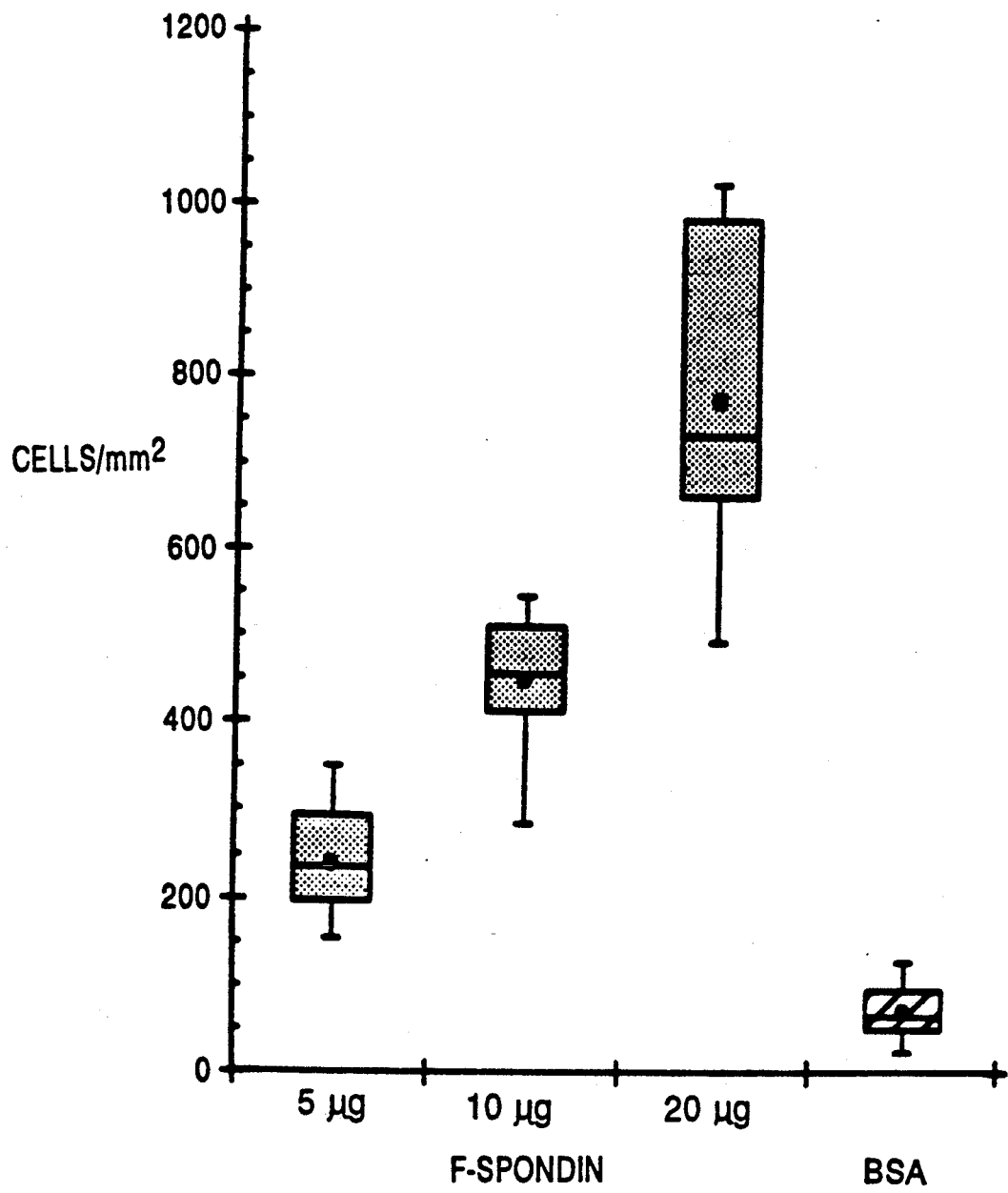
Figure 10F:
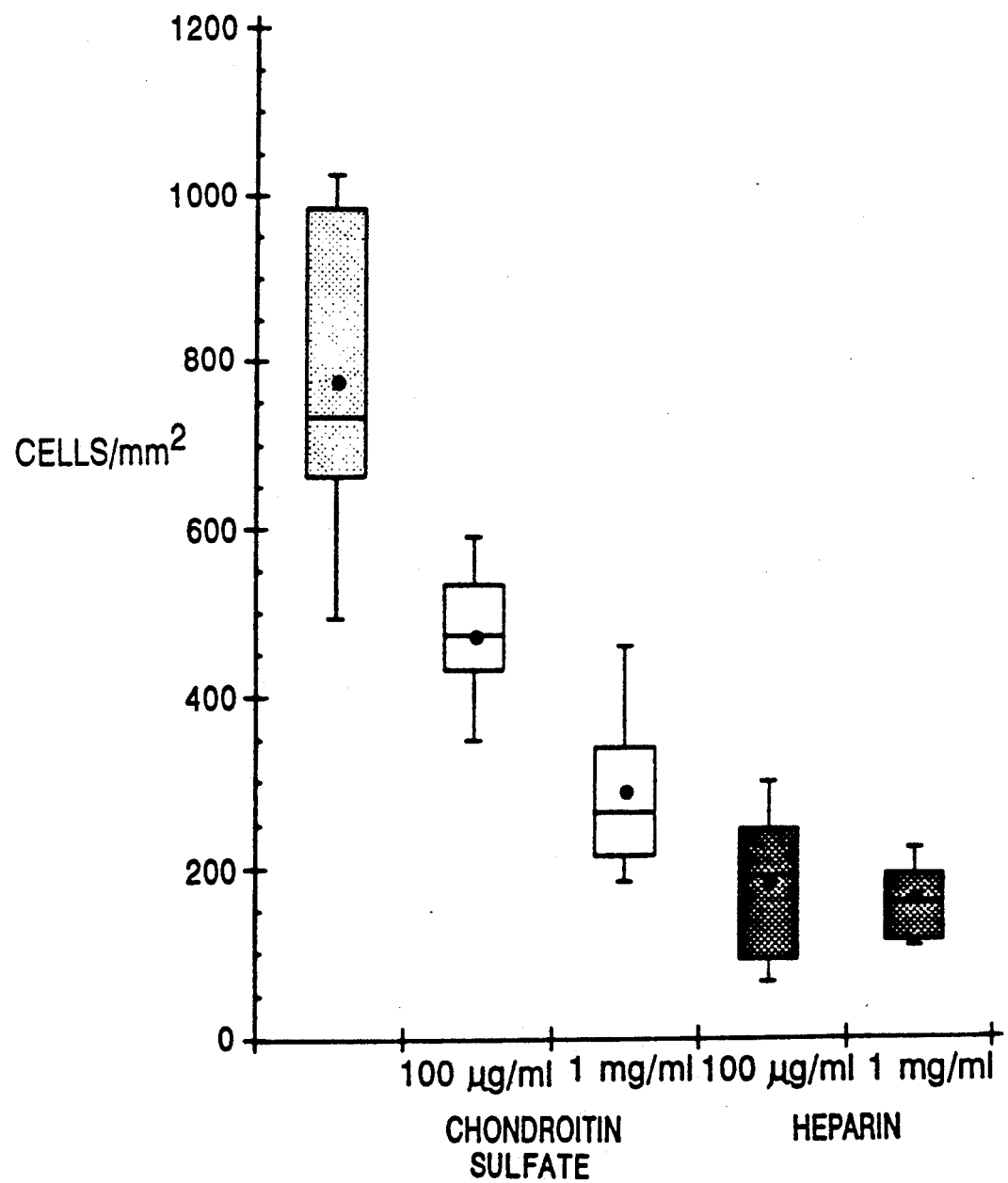

The ability of F-spondin$^{myc}$ to promote the adhesion and outgrowth of dorsal spinal cord cells was also examined. We found that dorsal spinal cord cells adhered well to F-spondin$^{myc}$. Within 60 min (FIGS. 10A, E) the number of cells adhering to F-spondin was 10–15 fold greater than that to MAb 9E10 affinity-purified proteins secreted from untransfected cos cells or to BSA (FIGS. 10C, E). The majority (>60%) of the adherent cells are neurons as determined by detection of the polysialic acid side chain of NCAM with MAb 5A5 (not shown; see Dodd et al., 1988; Karagogeos et al., 1991). Moreover, many adherent spinal cord neurons extended short neurites during this time period (FIG. 10B). To examine further whether F-spondin promotes the outgrowth of spinal cord neurites we determined the neurite length of adherent spinal cord neurons after 18 h in vitro. Thus it remains unclear whether F-spondin promotes extensive neurite outgrowth as well as the adhesion of spinal cord neurons.

The adhesion of a variety of cell lines to TSRs or to peptide derived from these repeats has been shown to be inhibited by glycosaminoglycans and other sulfated glycoconjugates (Roberts, 1988; Bernfield and Sanderson, 1990; Prater et al., 1991). Moreover, heparin sulfate proteoglycans have been suggested to function as cell surface receptors for thrombospondin (Holt et al., 1984; Sun et al., 1989; Bernfield and Sanderson, 1990). It is possible therefore that the interactions of neural cells with F-spondin may be inhibitable by addition of soluble glycosaminoglycans. We found that adhesion of dorsal spinal cord neurons to F-spondin was markedly inhibited by heparin, dextran sulfate (not shown) and to a lesser extent by chondroitin sulfate (FIGS. 10D, F). To control for non-specific inhibition of the interactions of spinal cord cells with all adhesive substrates, we determined that spinal cord neurons adhere well to fibronectin and that their adhesion is not significantly affected by concentrations of heparin that block adhesion to F-spondin (not shown). Heparin also reduced to near background levels the adhesion of DRG neurons to F-spondin (not shown). We were not able to determine whether the outgrowth of neurites from DRG neurons is also blocked by addition of glycosaminoglycans because heparin caused the detachment of virtually all neurons from the F-spondin substrate, even when added to DRG neurons that had been permitted to settle on F-spondin for 2–3 h.

Experimental Discussion

Floor plate cells are located at the ventral midline of the developing nervous system and have been implicated in the control of neural cell identity and in the guidance of developing axons (Jessell and Dodd, 1991). In order to identify genes that might contribute to the functions of the floor plate we have used subtractive hybridization techniques to isolate cDNA clones encoding a novel protein, F-spondin. F-spondin mRNA is expressed at high levels by the developing floor plate and at low or undetectable levels in other regions of the embryonic spinal cord over the period that axons first extend. The predicted structure of F-spondin together with its biochemical properties indicates that it is a secreted glycoprotein with homology to other proteins that mediate cell adhesion and neurite outgrowth. F-spondin promotes the adhesion and outgrowth of axons from embryonic neurons in vitro suggesting that it may contribute to the growth and guidance of commissural axons at the ventral midline of the spinal cord and of sensory axons in the periphery.

Localization of F-Spondin

Several lines of evidence suggest that the F-spondin protein may be associated with the extracellular matrix. First, F-spondin has several clusters of basic residues that function as glycosaminoglycan binding domains in other secreted proteins. Second, F-spondin is associated with the surface of cos cell transfectants. Third, the complement binding protein properdin which consists almost entirely of 6 TSRs has been shown to bind sulfated glycoconjugates (Holt et al., 1990).

The restricted distribution of F-spondin mRNA in the embryonic nervous system contrasts with that of other secreted glycoproteins which promote neural cell adhesion and neurite outgrowth For example, the expression of F-spondin mRNA is more restricted than that of thrombospondin I (O'Shea and Dixit, 1988; O'Shea et al., 1990) and of tenascin/cytotactin (Wehrle and Chiqet, 1990) which appears to be widely expressed in the embryonic central nervous system. Similarly, laminin and fibronectin are expressed in many regions of the developing peripheral nervous system (Sanes et al., 1990). One glycoprotein which has a restricted distribution during nervous system development is S-laminin, an isoform of the laminin B chain (Hunter et al., 1989a).

The TSRs of F-Spondin may be Responsible For Neural Cell Adhesion and Axon Extension The domains of F-spondin that mediate neural cell adhesion and neurite extension have not been mapped although several indirect lines of evidence suggest that the TSRs may be involved. First, proteolytic fragments of thrombospondin which contain the TSRs promote the adhesion of melanoma cells and antibodies directed against the TSRs domain block cell adhesion (Prater et al., 1991). Second, both native thrombospondin and a 140 kDa proteolytic fragment which includes the TSR domains promote the outgrowth of neurites from central and peripheral neurons in vitro (Osterhout and Higgins, 1990; Osterhout et al., 1992; Neugebauer et al., 1991; O'Shea et al., 1991). In addition, antibodies directed against the TSR domains block neurite outgrowth on thrombospondin (Osterhout and Higgins, 1990; Osterhout et al., 1992). Third, the plasmodial CS proteins, which contain the core domain of the TSRs also promote the adhesion of a wide variety of mammalian cells (Rich et al., 1990).

The adhesive properties of the CS proteins have been mapped to the VTCG sequence (Rich et al , 1990). In addition, the two peptides derived from the TSRs in thrombospondin that are potent attachment factors for melanoma cells also contain the VTCG sequence whereas the peptide derived from the third TSR which does not contain this sequence is not adhesive (Prater et al., 1991). Thus, the presence of a VTCG in the fourth TSR of F-spondin suggests that this domain could be involved in the adhesive properties of F-spondin. Nevertheless, other domains within F-spondin may be involved in neural cell adhesion or neurite outgrowth. For example, the region interposed between the fifth and sixth TSP-1 repeats of F-spondin contains an LRE sequence that mediates the neuronal attachment properties of S-laminin (Hunter et al., 1989b).

The ability of neural cells to adhere to and extend neurites on F-spondin suggests that there are neural receptors for this protein. The inhibition by heparin of the adhesion of dorsal spinal cord cells and DRG neurons to F-spondin suggests that proteoglycans may constitute neuronal F-spondin receptors or may regulate receptor function.

The conservation of TSRs in F-spondin and thrombospondin also raises the possibility that receptors for the TSR domains of thrombospondin may interact with the related domains of F-spondin. There is evidence that the TSRs of thrombospondin can interact with 3 distinct classes of cellular receptors (Frazier, 1991). First, thrombospondin and a VTCG-containing peptide from the TSR core region can bind to an 88 kDa membrane glycoprotein, GPIV, or CD36, which is present on many cell types (Asch et al., 1990, 1991). Second, thrombospondin can bind to sulfated glycoconjugates including the heparin sulfate proteoglycan syndecan (Roberts, 1988; Sun et al., 1989; Holt et al , 1989; Bernfied and Sanderson, 1990). In addition, the adhesion of cells to VTCG-containing peptides derived from the TSR domains of thrombospondin and plasmodial CS proteins can be inhibited by heparin and other glycosaminoglycans (Holt et al., 1990; Prater et al., 1991; Rich et al., 1991). Third, antibodies against integrins block neurite outgrowth on thrombospondin (Neugebauer et al., 1991). Since antibodies to the TSR domains of thrombospondin block the outgrowth of neurites on thrombospondin (Osterhout and Higgins, 1990; Osterhout et al., 1992) it is possible that sequences within the TSRs interact with neuronal integrins.

Possible Functions of F-Spondin in Neural Development

The most prominent expression of F-spondin in the embryonic nervous system is in the floor plate, an epithelial cell group that has been implicated in several aspects of spinal cord development. Midline neural plate cells that give rise to the floor plate undergo marked cell shape changes during the closure of the neural tube. Thus, one possible function of F-spondin could be to mediate adhesive interactions between floor plate cells that maintain the integrity of the floor plate during the formation of the embryonic spinal cord. The expression of F-spondin mRNA in floor plate cells is highest at the time that the floor plate has been suggested to have roles in the chemotropic (Tessier-Lavigne et al., 1988; Placzek et al., 1990a) and contact (Dodd et al., 1988) guidance of commissural axons. We have found that recombinant F-spondin$^{myc}$ secreted from cos cells does not mimic the ability of the floor plate derived chemoattractant to promote the outgrowth of commissural axons from dorsal spinal cord explants (Klar, Placzek, Tessier-Lavigne, Dodd and Jessell, unpublished observations). This suggests that F-spondin may not be involved in the long-range guidance of commissural axons to the floor plate, at least through chemotropism.

F-spondin could be involved in the contact-dependent guidance of commissural axons once they reach the ventral midline of the spinal cord under the influence of chemotropic guidance cues. The growth cones of commissural neurons cross the midline by growing between the basal surface of floor plate cells and the underlying basal lamina (Kuwada et al., 1990; Yaginuma et al., 1991). F-spondin secreted by the floor plate may accumulate at high levels in association with the basal surface of floor plate cells or with the underlying basal lamina thus generating a difference in adhesive properties of the floor plate and the lateral neuroepithelium. The growth cones of commissural neurons may adhere preferentially to F-spondin, prompting them to change trajectory at the boundary of the floor plate and lateral neuroepithelium. It is also possible that F-spondin has a more active signalling role which induces changes in the properties of commissural growth cones that permits them to respond to other midline guidance cues. Several proteins are expressed selectively on the surface of floor plate cells at this stage of spinal cord development (Dodd and Jessell, 1988; Chuang and Lagenaur, 1990) and could provide cues that contribute to the guidance of commissural axons at the midline.

F-spondin mRNA is also expressed by cells in the peripheral nerve, presumably Schwann cells, from E11 to E16 over the period that motor and sensory axons project to their peripheral targets. Non-neuronal cells in peripheral nerve are known to secrete a variety of extracellular matrix glycoprotein, including laminin and fibronectin that can promote the growth of developing axons. Antibody inhibition studies have provided evidence for the existence of additional molecules that mediate neuronal outgrowth on peripheral nerve substrates (Tuttle et al., 1989). The ability of recombinant F-spondin to promote the outgrowth of embryonic sensory neurons in vitro suggests that the protein may be released by non-neuronal cells in the peripheral nerve and could contribute to the initial outgrowth of sensory axons in vivo.

Taken together, the present studies identify F-spondin as a novel secreted protein with potential roles in neural cell adhesion and neurite outgrowth in vivo. The development of antibodies that recognize native F-spondin will be important in determining the localization of the protein within the nervous system and in assessing its function in more detail.

References

1. Asch, A. S., Heimer, E. and Nachman, R. L. (1990) An amino acid sequence motif in thrombospondin is responsible for CD36 binding. Blood 76:445a, Suppl 1.
2. Asch, A. S., Tepler, J., Silbiger, S. and Nachman, R. L. (1991) Cellular attachment to thrombospondin Cooperative interactions between receptor systems. J. Biol. Chem. 226:1740-1745.
3. Bazan, J. F. (1990) Structural design and molecular evolution of cytokine receptor superfamily. Proc Natl Acad. Sci. 87:6934-6938.
4. Bernfield, M. and Sanderson, R. D. (1990) Syndean, a developmentally regulated cell surface proteoglycan that binds extracellular matrix and growth factors. Philos. Trans. R. Soc. Lond. 327:171-186.

5. Bernhardt, R. R. and Kuwada, J. Y. (1990) Floor plate ablations induces axonal pathfindings errors by spinal commissural cells in the zebrafish embryo. Soc. Neurosci. Abst. 16:139.2.
6. Bornstein, P., O'Rourke, K., Wikstrom, K., Wolff, F. W., Katz, R., Li, P. and Dixit, V. M. (1991) A second, expressed thrombospondin gene (Thbs2) exists in the mouse genome. J. Biol. Chem 266:12821-12824.
7. Bovolenta, P. and Dodd, J. (199) Guidance of Commissural growth cones at the floor plate in the embryonic rat spinal cord. Developmentl 109:435-447.
8. Bovolenta, P. and Dodd, J. (1991) Perturbation of neuronal differentiation and axon guidance in the spinal cord of mouse embryos lacking a floor plate: Analysis of Danforth's short-tail mutation Development 113:625-639.
9. Cardin, A. D. and Weintraub, H. J. R. (1989) Molecular modeling of protein-glycosaminoglycan interactions. Arteriosclerosis 9:21-32.
10. Chuang, W. and Lagenaur, C. F. (1990) Central nervous system antigen P84 can serve as a substrate for neurite outgrowth. Dev. Biol. 137:219-232.
11. Culotti, J. G., Spence, A., Zhou, Y., Scott, I., Leugn-Hagesteijn, C., Stern, B. and Hedgecock, E. (1991) The unc-5 axon guidance gene of C.elegans has features of a cell adhesion receptor. J. Cell Biol. 115:122a.
12. Dame, J. B., Williams, J. L., McCutchan, T. F., Weber, J. L., Writz, R. A., Hockmeyer, W. T., Maloy, W. L., Haynes, J. D., Schneider, I., Roberts, D., Sanders, G. S., Reddy, E. P., Diggs, C. L. and Miller, L. H. (1984) Structure of the gene encoding the immunodominant surface antigen on the sporozoite of the human malaria parasite plasmodium falciparum. Science 225:593-599.
13. Davis, S., Aldrich, T. H., Valenzuela, D. M., Wong, V. V., Furth, M. E., Squinto, S. P. and Yancopoulos, G. D. (1991) The receptor for ciliary neurotrophic factor. Science 253:59-63.
14. Dodd, J. and Jessell, T. M (1985) Lactoseries carbohydrates specify subsets of dorsal root ganglion neurons and projecting to the superficial dorsal horn of rat spinal cord. J. Neurosci. 6:3278-3294.
15. Dodd, J. and Jessell, T. M (1988) Axon guidance and the patterning of neuronal projections in vertebrates Science 242:692-699.
16. Dodd, J , Morton, S. B., Karagogoes, D., Yamamoto, M. and Jessell, T. M. (1988) Spatial regulation of axonal glycoprotein expression on subsets of embryonic spinal neurons. Neuron 1:105-116.
17. Evan, G. I , Lewis, G. K., Ramsay, G , Bishop, J. M. (1985) Isolation of monoclonal antibodies specific for human c-myc proto-oncogene product Mol. Cell. Biol. 5:3610-3616.
18. Feinberg, A. P. and Volgelsten, B. (1983) A technique for radiolabelling DNA restriction endonuclease fragments to high specific activity. Anal. Biochem. 132:6-13.
19. Frazier, W. A. (1991). Thrombospondins. Current Opinions in Cell Biology 3:792-799.
20. Furley, A. J., Morton, S. B., Manalo, D., Karagogeos, D., Dodd, J. and Jessell T. M. (1990) The axonal glycoprotein TAG-1 is an immunoglobulin superfamily member with neurite outgrowth-promoting activity. Cell 61:157-170.
21. Goundis, D. and Reid, K. B. M. (1988) Properdin, the terminal complement components, thrombospondin and the circumsporozoite protein of malaria parasites contain similar sequence motifs. Nature 335:62-65.
22. Haefliger, J-A., Tschopp, J., Vial, N. and Jennet, D. E. (1989) Complete primary structure and functional characterization of the sixth component of the human complement system. J. Biol. Chem. 264:18041-18051.
23. Harland, R. M. (1991) In situ hybridization: an improved whole mount method for Xenopus embryos. Methods in Cell Biology 36:675-685.
24. Harlow, E. and Lane, D. (1988) Antibodies: A Laboratory Manual. Cold Spring Harbor Laboratory.
25. Hatta, K., Kimmel, C. B., Ho, R. K. and Walker, C. (1991) The cyclops mutation blocks specification of the floor plate of the zebrafish central nervous system. Nature 350:339-341.
26. Hedgecock, E. M., Culotti, J. G. and Hall, D. H. (1990) The unc-5, unc-6 and unc-40 genes guide circumferential migrations of pioneer axons and mesodermal cells on the epidermis in C. Elegans. Neuron 2:61-85.
27. Hedgecock, E. M. and Hall, D. H. (1990) Homologies in the neurogenesis of nematodes, arthropods and chordates. Seminar in Neurosci. 2:159-172.
28. Hession, C., Tizard, R., Vassallo, C., Schiffer, S. B., Goff, D., Moy, P., Chi-Rosso, G., Luhowskyj, S., Lobb, R. and Osborn, L. (1991) Cloning of an alternate form of vascular cell adhesion molecule-1 (VCAM1). J. Biol. Chem. 266:6682-6685.
29. Holley, J. and Silver, J. (1987) Growth pattern of pioneering chick spinal cord axons. Devl. Biol. 123:375-388.
30. Holdt, G. D., Kaesberg, P. R., Ershler, W. B., Esko, J. D. and Mosher, D. F. (1989) Chinese hamster ovary cell adhesion to human platelet thrombospondin is dependent on cell surface heparan sulfate proteoglycan. 83:994-1001.
31. Holt, G. D., Pangburn, M. K. and Ginsburg, V. (1990) Properdin binds to sulfatide [Gal(3-$SO_4$)$\beta$1-1Cer] and has a sequence homology with other proteins that bind sulfated glycoconjugates. J. Biol. Chem. 265:2852-2855.
32. Hunter, D. D., Shah, V., Merlie, J. P. and Sanes, J. R. (1989b) A laminin-like adhesive protein concentrated in the synaptic cleft of the neuromuscular junction. Nature 338:229-233.
33. Hunter, D. D., Porter, B. E., Bulock, J. W., Adams, S. P., Merlie, J. P. and Sanes, J. R. (1989) Primary sequence of a motor neuron-selective adhesive site in the synaptic basal lamina protein S-laminin. Cell 59:90-913.
34. T. M. and Dodd, J. (1991) Floor plate-derived signals and the control of neural cell pattern in vertebrates. Harvey Lecture Series (In Pres).
35. Karagogeos, D., Morton, S. B., Casano, F., Dodd, J. and Jessell, T. M. (1991) Developmental expression of the axonal glycoprotein TAG-1: Differential regulation by central and peripheral neurons in vitro. Development 112:61-67.
36. Klambt, C., Jacobs, J. R. and Goodman, C. S. (1991) The midline of the drosophila central nervous system: a model for the genetic analysis of cell fate, cell migration and growth cone guidance. Cell 64:801-815.
37. Kozak, M. (1984) Compilation and analysis of sequences upstream from the translational start site in eukaryotic mRNA. Nucl. Acids Res. 12:857-872.
38. Kuwada, J. Y., Bernhardt, R. R. and Nguyen, N. (1990) Development of spinal neurons and tracts in the zebrafish embryo. J. Comp. Neurol. 302:617-628.

39. Kyte, J. and Doolittle, R. F. (1982) A simple method for displaying the hydropathic character of a protein. J. Mol. Biol. 157:105–132.

40. Lawler, J. and Hynes, R. O. (1986) The structure of human thrombospondin, an adhesive glycoprotein with multiple calcium-binding sites and homologies with several different proteins. J. Cell. Biol. 103:1635–1648.

41. Lemmon, V., Farr, K. L. and Lagenaur, C. (1989) L1-mediated axon outgrowth occurs via a homophilic binding mechanism. Neuron 2:1597–1603.

42. McKanna, J. A. and Cohen, S. (1989) The EGF receptor kinase substrate p35 in the floor plate of the embryonic rat CNS. Science 243:1477–1479.

43. Miller, R. H. (1991) Ventral origin of A2B5-immunoreactive glial precursor cells in the developing rat spinal cord. Soc. Neuro. Sci. Abst. 17:235.

44. Miyazaki, T., Maruyama, M., Yamada, G., Hatakeyama, M. and Taniguchi, T. (1991) The integrity of the conserved 'WS motif' common to IL-2 and other cytokine receptors is essential for ligand binding and signal transduction. The EMBO Journal 10:3191–3197.

45. Nambu, J. R., Lewis, J. O., Wharton, K. A. and Crews, S. T. (1991) The drosophila single-minded gene encodes a helix-loop-helix protein that acts as a master regulator of CNS midline development. Cell 67:1157–1167.

46. Neugebauer, K. M., Emmett, C. J., Venstrom, K. A. and Reichardt, L. F. (1991) Vitronectin and thrombospondin promote retinal neurite outgrowth: Developmental regulation and role of integrins. Neuron 6:345–358.

47. O'Shea, K. S. and Dixit, V. M. (1988) Unique distribution of the extracellular matrix component thrombospondin in the developing mouse embryo. J. Cell Biol. 107:2737–2748.

48. O'Shea, K. S. and Rheinheimer, J. S. T. and Dixit, V. M. (1990) Deposition and role of thrombospondin in the histogenesis of the cerebellar cortex. J. Cell Biol. 110:1275–1283.

49. O'Shea, K. S., Liu, L-H. J. and Dixit, V. M. (1991) Thrombospondin and a 140 kd fragment promote adhesion and neurite outgrowth from embryonic central and peripheral neurons and from PC12 cells. Neuron 7:231–237.

50. Osterhout, D. J. and Higgins, D. (1990) Thrombospondin promotes axonal growth in sympathetic neurons Soc. Neurosci Abst. 16:312.

51. Osterhout, D. J., Frazier, W. A. and Higgin, D. (1992) Thrombospondin promotes process outgrowth in neurons from the peripheral and central nervous systems. Dev. Biol. In Press.

52. Patthy, L. (1990) Homology of a domain of the growth hormon/prolactin receptor family with type III modules of fibronectin. Cell 61:13–14.

53. Patthy, L. (1988) Detecting distant homologies of mosaic proteins. Analysis of the sequences of thrombomodulin, thrombospondin complement components C9, C8 alpha and C8 beta, vitronectin and plasma cell membrane glycoprotein PC-1. J. Mol. Biol. 202:689–696.

54. Perkins, S. J., Nealis, A. S., Haris, P. I., Chapman, D., Goundis, D. and Reid, K. B. M. (1989) Secondary structure in properdin of the complement cascades and related proteins: A study by fourier transforms infrared spectroscopy. Biochemistry 28:7176–7182.

55. Placzek, M., Tessier-Lavigne, M., Jessell, T. M. and Dodd, J. (1990a) Orientation of Commissural axons in vitro in response to a floor plate derived chemoattractant. Development 110:19–30.

56. Placzek, M , Tessier-Lavigne, M., Yamada, T., Jessell, T. M. and Dodd, J.(1990b) The guidance of developing axons by diffusible chemoattractants. Cold Spring Harbor Symp 55:279–988.

57. Placzek, M., Tessier-Lavigne, M., Yamada, T., Jessell, T. M. and Dodd, J. (1990c) Mesodermal control of neural cell identity: floor plate induction by the notochord. Science 250:985–988.

58. Placzek, M., Yamada, T., Tessier-Lavigne, M., Jessell, T. M., Dodd, J. (1991) Control of dorso ventral pattern in vertebrate neural development: induction and polarizing properties of the floor plate. Development (In Press).

59. Prater, C. A., Plotkin, J., Jaye, D. and Frazier, W. A. (1991) The properdin-like type I repeats of a human thrombospondin contain a cell attachment site. Cell Biol. 112:1031–1040.

60. Rich, K. A., George, F. W., Law, J. L. and Martin, W. J. (1990) Cell-adhesive motif in region II of malarial circumsporozoite protein. Science 249:1574–1577.

61. Rich, K. A., Hinton, D. R. and Blanks, J. B. (1991) Attachment of developing mouse retinal and lens cells to a sequence common to thrombospondin and malarial proteins. J. Cell Biol. 115:441a.

62. Roberts, D. D. (1988) Interactions of thrombospondin with sulfated glycolipids and proteoglycans of human melanoma cells. Cancer Research 48:6785–6793.

63. Robson, K. J. H., Hall, J. R. S., Jennings, M. W., Harris, T. J. R., Marsh, K., Newbold, C. I., Tate, V. E., Weatherall, D. J. (1988) A highly conserved amino-acid sequence in thrombospondin, properdin and in proteins from sporozoites and blood stages of a human malaria parasite. Nature 335:79–82.

64. Romijin, H. J., Gabets, A. M. M. C., Mud, M. T. and Walter, P. S. (1982) Nerve outgrowth, synaptogenesis and bioelectric activating in rate cerebral cortex tissue cultured in serum-free, chemically defined medium. Devl. Brain. Res. 2:583–589.

65. Sambrook, J., Fritsch, E. F. and Maniatis, T. (1989) Molecular Cloning. Cold Spring Harbor Laboratory Press.

66. Sanes, J.r., Engvall, E., Butkowski, R. and Hunter, D. D. 91990) Molecular heterogeneity of basal laminae: Isoforms of laminin and collagen IV at the neuromuscular junction and elsewhere. J. Cell Biol. 111:1685–1699.

67. Sanger, F., Nicklen, S. and Coulson, A. R. (1988) DNA sequencing with chain-terminating inhibitors. Proc. Natl. Acad. Sci. 74:5463.

68. Schachner, M., Antonicek, H., Fahrig, T. et al. (1990) Families of neural cell adhesion molecules. In Morphoregulatory Molecules (eds. G. M. Edelman, B. A. Cunningham and J. P. Thiery) John Wiley and Sons, New York, pp. 443–468.

69. Sive, H. L. and John, T. S. (1988) A simple subtractive hybridization technique employing photoactivatable blotin and phenol extraction. Nucl. Acids. Res. 16:10937.

70. Smith, K. F., Nolan, K. F., Reid, K. B. M. and Perkins, S. J. (1991) Neutron and X-ray scattering studies of the human complement protein properdin provide an analysis of the thrombospondin repeat. Biochemistry 30:8000-80008.
71. Steiner, D. F. (1991) Prohormone convertases revealed at last. Current Biology 1:375-377.
72. Sun, X., Mosher, D. F. and Rapraeger, A. (1989) Heparan sulfate-mediated binding of epithelial cell surface proteoglycan to thrombospondin. J. Biol. Chem 264:2885-2889.
73. Takada, Y., Elices, M. J., Crouse, C., Hemler, M. E. (1989) The primary structure of the α subunit of VLA-4: homology to other integrins and a possible cell-cell adhesion function. EMBO J. 8:1361-1368.
74. Tessier-Lavigne, M. and Paczek, M. (1991) Target attraction: are developing axons guided by chemotropism? Trends in Neuroscience 14:303-310.
75. Tessier-Lavigne, M., Placzek, M., Lumsden, A. G. S., Dodd, J. and Jessell, T. M. (1988) Chemotropic guidance of developing axons in the mammalian central nervous system. Nature 335:775-778.
76. Thomas, P. (1983) Hybridization of denatured RNA transferred or dotted onto nitrocellulose paper. Meth. Enzymol. 100:255-266.
77. Tuttle, R., Sandrock, A. W. and Matthew, W. D. (1989) Analysis of complex matrices functional in neuronal process extension using monoclonal antibodies in vitro and in vivo. Dev. Neurosci. 11:289-299.
78. van Straaten, H. W. M., Hekking, J. W. M., Wiertz-Hoessels, E. L., Thors, F. and Drukker, J. (1988) Effect of the notochord on the differentiation of a floor plate area in the neural tube of the chick embryo. Anat. Embryol. 177:317-324.
79. von Heijine, G. (1985) Signal sequences: the limits of variation. J. Mol. Biol. 184:99-105.
80. Wagner, M., Thaller, C., Jessell, T. M. and Eichele, G. (1990) Polarizing activity and retinoid synthesis by the floor plate of the neural tube. Nature 345:819-822.
81. Weber, A. (1938) Croissance de fibres nerveuses commissurales lors de lesion de la moelle epiniere chez de jeunes embryons de poulet. Biomorphosis 1:30-35.
82. Wehrle, B. and Chiqet M. (1990) Tenascin is accumulated along developing peripheral nerves and allows neurite outgrowth in vitro. Development 110:401-415.
83. Wilkinson, D. G., Bailes, J. A., Champion, J. E. and McMahon, A. P. (1987) A molecular analysis of mouse development from 8 to 10 days post coitum detects changes only in embryonic globin expression. Development 99:493-500.
84. Yaginuma, H , Homma, S., Kunzi, L and Oppenheim, R. W. (1991) Pathfinding by growth cones of commissural interneurons in the chick embryo spinal cord: a light and electric micropscopic study. J. Comp. Neurol 304:78-102.
85. Yaginuma, H. and Oppenheim, R. W. (1991) An experimental analysis of in vitro guidance cues used by axons of spinal interneurons in the chick embryo: evidence for chemotropism and related guidance mechanisms. J. Neuroscience 11 2598-2613.
86. Yamada, T., Placzek, M., Tanaka, H., Dodd, J. and Jessell, T. M. (1991) Control of cell pattern in the developing nervous system Polarizing activity of the floor plate and notochord Cell 64:635-647.

---

We claim:

1. An isolated vertebrate nucleic acid molecule encoding F-spondin.

2. The isolated vertebrate nucleic acid molecule of claim 1, wherein the nucleic acid is DNA.

3. The isolated vertebrate nucleic acid molecule of claim 2, wherein the DNA is cDNA.

4. The isolated vertebrate nucleic acid molecule of claim 1, wherein the nucleic acid is RNA.

5. The isolated vertebrate nucleic acid molecule of claim 1, wherein the nucleic acid molecule is from humans.

6. The isolated vertebrate nucleic acid molecule of claim 1, wherein the nucleic acid molecule is from rats (Seq. ID No. 9).

7. The isolated vertebrate nucleic acid molecule of claim 1, wherein the nucleic acid molecule is from chickens (Seq. ID No. 11).

8. The isolated vertebrate nucleic acid molecule of claim 1, wherein the nucleic acid molecule is from Xenopus (Seq. ID No. 13).

9. A nucleic acid probe comprising a nucleic acid molecule of at least 15 nucelotides capable of specifically hybridizing with a sequence included within the seueqnce of a nucleic acid molecule encoding a F-spondin.

10. The nucleic acid probe of claim 9 wherein the nucleic acid is DNA.

11. The nucleic acid probe of claim 9 wherein the nucleic acid is RNA.

12. The isolated nucleic acid molecule of claim 1 operatively linked to a promoter of RNA transcription.

13. A vector which comprises the isolated nucleic acid molecule of claim 1.

14. The vector of claim 13, wherein the isolated nucleic acid molecule is linked to a plasmid.

15. A host vector system for the production of a polypeptide having the biological activity of F-spondin which comprises the vector of claim 13.

16. The host vector system of claim 15, wherein the suitable host is a bacterial cell, insect cell, or animal cell.

* * * * *